(12) United States Patent
Taveras et al.

(10) Patent No.: US 6,903,131 B2
(45) Date of Patent: Jun. 7, 2005

(54) 3,4-DI-SUBSTITUTED MALEIMIDE COMPOUNDS AS CXC CHEMOKINE RECEPTOR ANTAGONISTS

(75) Inventors: Arthur G. Taveras, Denville, NJ (US); Michael Dwyer, Scotch Plains, NJ (US); Johan A. Ferreira, Bethlehem, PA (US); Viyyoor M. Girijavallabhan, Parsippany, NJ (US); Jianping Chao, Summit, NJ (US); John J. Baldwin, Gwynedd Valley, PA (US); J. Robert Merritt, Ewing, NJ (US); Ge Li, Shanghai (CN)

(73) Assignees: Schering Corporation, Kenilworth, NJ (US); Pharmacopeia Drug Discovery, Inc., Cranbury, NJ (US)

( * ) Notice: Subject to any disclaimer, the term of this patent is extended or adjusted under 35 U.S.C. 154(b) by 0 days.

(21) Appl. No.: 10/269,775

(22) Filed: Oct. 11, 2002

(65) Prior Publication Data

US 2004/0034229 A1 Feb. 19, 2004

Related U.S. Application Data

(60) Provisional application No. 60/329,005, filed on Oct. 12, 2001.

(51) Int. Cl.$^7$ .................. A61K 31/4015; C07D 409/12
(52) U.S. Cl. ................. 514/425; 548/517; 548/527; 548/406; 548/204; 514/422
(58) Field of Search ................. 548/517, 204, 548/527, 406; 514/422, 425

(56) References Cited

U.S. PATENT DOCUMENTS

| | | | |
|---|---|---|---|
| 4,170,588 A | 10/1979 | Hegenberg et al. | |
| 4,639,523 A | 1/1987 | Nohara et al. | |
| 5,206,252 A | 4/1993 | Butera et al. | |
| 5,354,763 A | 10/1994 | Butera et al. | |
| 5,397,790 A | 3/1995 | Butera et al. | |
| 5,401,753 A | 3/1995 | Butera et al. | |
| 5,403,853 A | 4/1995 | Butera et al. | |
| 5,466,712 A | 11/1995 | Butera et al. | |
| 5,506,252 A | 4/1996 | Butera et al. | |
| 5,532,245 A | 7/1996 | Butera et al. | |
| 5,840,764 A | 11/1998 | Quagliato et al. | |
| 6,300,325 B1 | 10/2001 | Widdowson et al. | |
| 6,376,555 B1 | 4/2002 | Butera et al. | |
| 6,420,396 B1 | 7/2002 | Albers et al. | |
| 2001/0018447 A1 | 8/2001 | Widdwoson et al. | |
| 2003/0204085 A1 | 10/2003 | Taveras et al. | |
| 2004/0034229 A1 | 2/2004 | Taveras et al. | |
| 2004/0063709 A1 | 4/2004 | Taveras et al. | |

FOREIGN PATENT DOCUMENTS

| | | |
|---|---|---|
| DE | 33 09 655 A1 | 9/1984 |
| EP | 0 099 121 A2 | 4/1984 |
| EP | 0 275 997 A | 7/1988 |
| EP | 0 376 079 A | 7/1990 |
| EP | 0 796 243 B1 | 1/1999 |
| GB | 1186096 | 4/1970 |
| WO | WO 94/29277 | 12/1994 |
| WO | WO 95/14005 | 5/1995 |
| WO | WO 96/14300 | 5/1996 |
| WO | WO 96/15103 | 5/1996 |
| WO | WO 98/33763 | 8/1998 |
| WO | WO 00/20378 | 4/2000 |
| WO | WO 00/21927 A | 4/2000 |
| WO | WO 00/21927 | 4/2000 |
| WO | WO 00/35855 | 6/2000 |
| WO | WO 00/35864 | 6/2000 |
| WO | WO 00/73260 A1 | 12/2000 |
| WO | WO 01/29000 A2 | 4/2001 |
| WO | WO 01/64208 A1 | 9/2001 |
| WO | WO 01/64691 A1 | 9/2001 |
| WO | WO 01/68569 A2 | 9/2001 |
| WO | WO 01/92202 A1 | 12/2001 |
| WO | WO 02/057230 A1 | 7/2002 |
| WO | WO 02/067919 | 9/2002 |
| WO | WO 02/076926 A1 | 10/2002 |
| WO | WO 02/076926 A | 10/2002 |
| WO | WO 02/083624 A1 | 10/2002 |
| WO | WO 03/057676 A1 | 7/2003 |
| WO | WO 03/080053 A1 | 10/2003 |

OTHER PUBLICATIONS

Esp@cecent Document, "1,2,5–Thiadiazole–1–oxides and 1,1–dioxides, process for their preparation and their use as medicaments" (for DE3309655 which is attached to said esp document).

Chemical Abstract 66:18527 for Maahs, Guenther, et al., "Syntheses and derivatives of squaric acid," *Angewandte Chemie* 78(20):927–31 (1966) (which is attached to said abstract).

Chemical Abstract 87:134383 for Augustin Manfred, et al., "Disubstitution in 2,3–dichloromaleimides" *Zeitschrift Fuer Chemie* 17(6):215–216 (1977) (which is attached to said abstract).

(Continued)

*Primary Examiner*—Golam M M Shameem
(74) *Attorney, Agent, or Firm*—Henry C. Jeanette

(57) ABSTRACT

Disclosed are compounds of the formula (I)

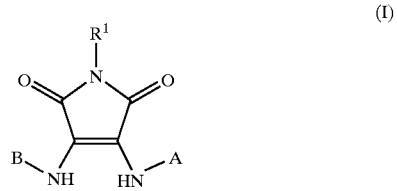

or a pharmaceutically acceptable salt or solvate thereof. The compounds are useful for the treatment of chemokine-mediated diseases such as acute and chronic inflammatory disorders and cancer.

21 Claims, No Drawings

OTHER PUBLICATIONS

Chemical Abstract No. 87:151727 for Ehrhardt, Heinz, et al., "Amides and thioamides of squaric acid: syntheses and reactions," *Chemishce Berichte* 110(7):2506–23 (1977) (which is attached to said abstract).
Chemical Abstract 104:129517 for Gruenefeld, Johann, et al., "Reactions of squaric acid with carbodiimides," *Archiv der Pharmazie* 318(12):1062–70 (1985) (which is attached to said abstract).
Chemical Abstract No. 122:160745 for Tillack, Annegret, et al., "Assymmetric catalysis. IV. Hydrosilylation of acetophenone with pyrroline–2,5–dione modified [Rh(COD)C1]2 catalyst," *Journal of Organometallic Chemistry* 482(1–2):85–91 (1994) (which is attached to said abstract).
Chemical Abstract No. 125:300482 for Chen, Yizhao, et al., "Reaction of dibutyl oxosquarate with aromatic primary amines," *Sichuan Daxue Xuebao, Ziran Kexueban* 33(2):182–186 (1996) (which is attached to said abstract).
Chemical Abstract No. 130:222994 for Chen, Yi–Zhao, et al., "Synthesis of asymmetric aryl–substituted amides of squaric acid and asymmetric isosquarylium amides," *Hecheng Huaxue* 6(4):383–392 (1998) (which is attached to said abstract).
Butera, John A., et al., "Design and SAR of Novel Potassium Channel Openers Targeted for Urge Urinary Incontinence. 1. N–Cyanoguanidine Bioisosteres Possessing in Vivo Bladder Selectivity," *J. Med. Chem.* 43:1187–1202 (2000).
Davis, Peter D., et al., "Inhibitors of protein kinase C. 1. 2,3–Bisarylmaleimides," *J. Med. Chem.* 35:177–184 (1992).
Hanaineh–Abdelnour, Leila, et al., "Some synthetic applications of 2,3–Dichloro–N–phenylmaleimide: A Novel Synthesis of 2–Phenylpyrrolo[3,4–b]quinoxaline–1,3–diones. I," *Tetrahedron* 55:11859–11870 (1999).
Neuse, Eberhard W., et al., "Poly(squaryl amides)" *Polymer* 15:339–45 (1974).
Patent Abstracts of Japan, vol. 018, No. 361 (c–1222), Jul. 7, 1994 and JP 06 092915A, Apr. 5, 1994 abstract.
Zhou, Hai–Bing, et al., "Design, synthesis and structure of new chiral squaric acid monoaminoalcohols and diaminoalcohols and their use as catalysts in asymmetric reduction of ketones and diketones," *Tetrahedron* 57:9325–9333 (2001).

U.S. Appl. No. 10/390,078, filed Mar. 17, 2003.
U.S. Appl. No. 10/630,258, filed Jul. 30, 2003.
U.S. Appl. No. 10/680,393, filed Oct. 7, 2003.
PCT International Search Report dated Feb. 17, 2003 for corresponding PCT Application No. PCT/US02/32628.
Chemical Abstract 102:24633 "1,2,5–Thiadiazole–1–oxide and 1,1–dioxides and their use as pharmaceuticals" (for DE3309655 which is attached to said abstract).
Hoffman, Jacob M., et al., "Conformational Requirements of Histamine $H_2$–Receptor Inhibitors: A Structure–Activity Study of Phenylene Analogues Related to Cimetidine and Tiotidine," *Journal of Medicinal Chemistry* 26(2):140–44 (1983).
Karady, Sandor, et al., "1,2,5–Thiadiazole–1–Oxides.I.Synthesis and Reactions of Alkoxy and Alkylthio Analogs," *Heterocycles* 16(9)1561–64 (1981).
Martinez, Ana, et al., "Synthesis of Nonsymmetrically 3,4–Disubstituted 1,2,5–Thiadiazole Dioxides," *Journal of Heterocyclic Chemistry* 35(2):297–300 (1998).
Schostarez, Heinrich J., et al., "Cyanoguanidine Bioisosteres in Potassium Channel Openers: Evaluation of 3,4–Disubstituted–1,2,5–Thiadiazole–1–Oxides," *Bioorganic & Medicinal Chemistry Letters* 6(18):2187–92 (1996).
Wen, Richard Y., et al., "The Chemistry of 1,2,5–Thiadizoles. II. 3,4–Disubstituted Derivatives of 1,2,5–Thiadiazole, 1,1–Dioxide," *J. Org. Chem.* 40(19):2743–8 (1975).
Augustin, et al. "Disubstitution in 2,3–dichloromaleimides" *Zeitschrift Fuer Chemie* 17(6):215–216(1977).
Davis, et al. "Inhibitors of protein kinase C 1. 2,3–Bisarylmaleimides" *J. Med. Chem.* 35:177–184(1992).
Tillack, et al. "Asymmetric catalysis. IV. Hydrosiylation of acetophenone with pyrroline–2,5–dione modified [Rh(COD)C1]$_2$–Catalyst" 482:85–91(1994).
Hanaineh–Abdelnour, et al. "Some synthetic applications of 2,3–Dichloro–N–phenylmaleimide" A novel synthesis of 2–Phenylpyrrolo[3,4,–b]quinoxaline–1,3–diones. I *Tetrahedron* 55:11859–11870(1999).
PCT International Search Report dated Feb. 17, 2003 for corresponding PCT Application No. PCT/US02/32628.
Chemical Abstract No. 87:134383 for Reference AC.
Chemical Abstract No. 122:160745 for Reference AE.

3,4-DI-SUBSTITUTED MALEIMIDE COMPOUNDS AS CXC CHEMOKINE RECEPTOR ANTAGONISTS

REFERENCE TO RELATED APPLICATION

This application claims the benefit of U.S. Provisional Application Ser. No. 60/329,005 filed Oct. 12, 2001, the disclosure of which is incorporated herein by reference thereto.

FIELD OF THE INVENTION

The present invention relates to novel substituted maleimide compounds, pharmaceutical compositions containing the compounds, and the use of the compounds in treating CXC chemokine-mediated diseases.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include RANTES, MIP-1α, MIP-2β, monocyte chemotactic protein-1 (MCP-1), MCP-2, MCP-3 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Lett. 307, 97 (1992); Miller et al., Crit. Rev. Immunol. 12,17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

ELRCXC chemokines including IL-8, GROα, GROβ, GROγ, NAP-2, and ENA-78 (Strieter et al. 1995 JBC 270 p. 27348-57) have also been implicated in the induction of tumor angiogenesis (new blood vessel growth). All of these chemokines are believed to exert their actions by binding to the 7 transmembrane G-protein coupled receptor CXCR2 (also known as IL-8RB), while IL-8 also binds CXCR1 (also known as IL-8RA). Thus, their angiogenic activity is due to their binding to and activation of CXCR2, and possible CXCR1 for IL-8, expressed on the surface of vascular endothelial cells (ECs) in surrounding vessels.

Many different types of tumors have been shown to produce ELRCXC chemokines and their production has been correlated with a more aggressive phenotype (Inoue et al. 2000 Clin Cancer Res 6 p. 2104–2119) and poor prognosis (Yoneda et. al. 1998 J Nat Cancer Inst 90 p. 447–454). Chemokines are potent chemotactic factors and the ELRCXC chemokines have been shown to induce EC chemotaxis. Thus, these chemokines probably induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg et al. 1996 J Clin Invest 97 p. 2792–2802), ENA-78 (Arenberg et al. 1998 J Clin Invest 102 p. 465–72), and GROα (Haghnegahdar et al. J. Leukoc Biology 2000 67 p. 53–62).

Many tumor cells have also been shown to express CXCR2 and thus tumor cells may also stimulate their own growth when they secrete ELRCXC chemokines. Thus, along with decreasing angiogenesis, inhibitors of CXCR2 may directly inhibit the growth of tumor cells.

Hence, the CXC-chemokine receptors represent promising targets for the development of novel anti-inflammatory and anti-tumor agents.

There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding.

SUMMARY OF THE INVENTION

The present invention provides novel compounds represented by the formula (I):

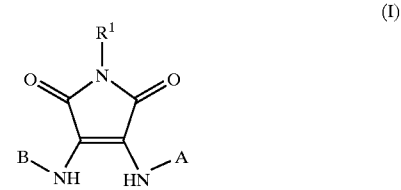

(I)

or a pharmaceutically acceptable salt or solvate thereof, wherein $R^1$, A and B are defined below.

This invention also provides a method of treating an α-chemokine mediated disease in a mammal which comprises administering to a patient in need thereof of a therapeutically effective amount of at least one (usually 1) compound of formula (I) or a pharmaceutically acceptable salt or solvate thereof.

This invention also provides a method treating a chemokine-mediated disease wherein the chemokine binds to a CXCR2 and/or CXCR1 receptor in a mammal, which comprises administering to a patient in need thereof a therapeutically effective amount of at least one (usually one) compound of formula I This invention also provides a method of treating a chemokine-mediated disease wherein the chemokine binds to a CXC receptor in a mammal, which comprises administering to a patient in need thereof a therapeutically effective amount of at least one (usually one) compound of formula I.

This invention also provides a method of treating cancer in a patient in need of such treatment comprising administering to said patient an effective amount of at least one (usually 1) compound of formula I.

This invention also provides a method of treating cancer in a patient in need of such treatment comprising administering to said patient an effective amount of at least one (usually 1) compound of formula I, and administering at least one known anti-cancer agent and/or radiation therapy.

This invention also provides a method of treating cancer in a patient in need of such treatment comprising administering to said patient an effective amount of at least one (usually 1) compound of formula I, and administering at least one known anti-cancer agent and/or radiation therapy, wherein said anti-cancer agent is selected from the group consisting of alkylating agents, antimetabolites, natural products and their derivatives, hormones, anti-hormones, anti-angiogenic agents and steroids (including synthetic analogs), and synthetics.

This invention also provides a method of treating cancer, comprising administering to a patient in need thereof, concurrently or sequentially, a therapeutically effective amount of (a) at least one (usually 1) compound of formula (I), and (b) at least one one anticancer agent selected from the group consisting of: microtubule affecting agents, antineoplastic agents, anti-angiogenesis agents, VEGF receptor kinase inhibitors, antibodies against the VEGF receptor, interferon, and radiation.

This invention also provides a method of treating cancer in a patient in need of such treatment comprising administering to said patient at least one (usually 1) compound of formula I in combination with at least one (usually 1) antineoplastic agent selected from the group consisting of: gemcitabine, paclitaxel (Taxol®), 5-Fluorourcil (5-FU), cyclophosphamide (Cytoxan®), temozolomide, and Vincristine.

This invention also provides a method of treating cancer, comprising administering, concurrently or sequentially, an effective amount of (a) at least one (usually 1) compound of formula (I), and (b) a microtubule affecting agent (e.g., paclitaxel).

This invention also provides a method treating cancer in a patient in need of such treatment comprising administering to said patient a therapeutically effective amount of: (a) at least one (usually 1) compound of formula I concurrently or sequentially with (b) at least one (usually 1) agent selected from the group consisting of: (1) antineoplastic agents, (2) microtubule affecting agents, and (3) anti-angiogenesis agents.

This invention also provides a method of inhibiting angiogenesis in a patient in need of such treatment comprising administering to said patient an effective amount of at least one (usually 1) compound of formula I.

This invention also provides a method of inhibiting angiogenesis in a patient in need of such treatment comprising administering to said patient an effective amount of at least one (usually 1) compound of formula I, wherein the tumor type is melanoma, gastric carcinoma or non-small cell lung carcinoma.

This invention also provides a method of inhibiting angiogenesis in a patient in need of such treatment comprising administering to said patient an effective amount of at least one (usually 1) compound of formula I, and administering at least one known anti-cancer agent and/or radiation therapy.

This invention also provides a method of inhibiting angiogenesis in a patient in need of such treatment comprising administering to said patient an effective amount of at least one (usually 1) compound of formula I, and administering at least one known anti-cancer agent and/or radiation therapy, wherein said anti-cancer agent is selected from the group consisting of alkylating agents, antimetabolites, natural products and their derivatives, hormones, anti-hormones, anti-angiogenic agents and steroids (including synthetic analogs), and synthetics.

This invention also provides a method of inhibiting angiogenesis in a patient in need of such treatment comprising administering to said patient an effective amount of at least one (usually 1) compound of formula I, and administering at least one known anti-cancer agent and/or radiation therapy, wherein said anti-cancer agent is selected from the group consisting of alkylating agents, antimetabolites, natural products and their derivatives, hormones, anti-hormones, anti-angiogenic agents and steroids (including synthetic analogs), and synthetics, wherein said anti-angiogenic agent is selected form the group consisting of Marimastat, AG3340, Col-3, Neovastat, BMS-275291, Thalidomide, Squalamine, Endostatin, SU-5416, SU-6668, Interferon-alpha, Anti-VEGF antibody, EMD121974, CAI, Interleukin-12, IM862, Platelet Factor-4, Vitaxin, Angiostatin, Suramin, TNP-470, PTK-787, ZD-6474, ZD-101, Bay 129566, CGS27023A, VEGF receptor kinase inhibitors, taxotere and Taxol.

This invention also provides a method of inhibiting angiogenesis in a patient in need of such treatment comprising administering to said patient an effective amount of at least one (usually 1) compound of formula I, and administering at least one known anti-angiogenesis compound.

This invention also provides a method of inhibiting angiogenesis in a patient in need of such treatment comprising administering to said patient an effective amount of at least one (usually 1) compound of formula I, and administering at least one known anti-angiogenesis compound, wherein said known anti-angiogenesis compound is selected from the group consisting of Marimastat, AG3340, Col-3, Neovastat, BMS-275291, Thalidomide, Squalamine, Endostatin, SU-5416, SU-6668, Interferon-alpha, Anti-VEGF antibody, EMD121974, CAI, Interleukin-12, IM862, Platelet Factor-4, Vitaxin, Angiostatin, Suramin, TNP-470, PTK-787, ZD-6474, ZD-101, Bay 129566, CGS27023A, VEGF receptor kinase inhibitors, taxotere and Taxol.

This invention also provides a method of treating a disease selected from the group consisting of gingivitis, respiratory viruses, herpes viruses, hepatitis viruses, HIV, kaposi's sarcoma associated virus and atherosclerosis in a patient in need of such treatment comprising administering to said patient a therapeutically effective amount of at least one (usually one) compound of formula I.

This invention also provides a method of treating angiogenic ocular disease (e.g., ocular inflammation (e.g., Uveitis), retinopathy of prematurity, diabetic retinopathy, macular degeneration with the wet type preferred and corneal neovascularization) in a patient in need of such treatment comprising administering to said patient an effective amount of at least one (usually 1) compound of formula I.

This invention also provides a method of treating a disease selected from the group consisting of: psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral and cardiac ischemia, osteoarthritis, multiple sclerosis, restinosis, angiogenesis, osteoporosis, gingivitis, respiratory viruses, herpes viruses, hepatitis viruses, HIV (i.e., AIDS), Kaposi's sarcoma associated virus, meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred and corneal neovascularization, polymyositis, vasculitis, acne, gastric and duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, cough, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy, periodontitis, transplant reperfusion injury and early transplantation in a patient in need of such treatment comprising administering to said patient an effective amount of at least one compound (usually 1) of formula I.

This invention also provides a method of treating a chemokine (i.e., a CXC chemokine) mediated disease in a patient in need of such treatment comprising administering to said patient at least one (usually 1) compound of formula I in combination with at least one (usually 1) other medicament (e.g., a drug, agent or therapeutic) useful for the treatment of chemokine mediated diseases.

This invention also provides a method of treating a chemokine mediated disease in a patient in need of such treatment comprising comprising administering to said patient at least one (usually 1) compound of formula I in combination with at least one (usually 1) other medicament (e.g., a drug, agent or therapeutic) selected from the group consisting of:

a) disease modifying antirheumatic drugs;

b) nonsteroidal anitinflammatory drugs;

c) COX-2 selective inhibitors;

d) COX-1 inhibitors;

e) immunosuppressives;

f) steroids;

g) biological response modifiers; and h) other anti-inflammatory agents or therapeutics useful for the treatment of chemokine mediated diseases.

This invention also provides a method of treating a pulmonary disease (e.g., COPD asthma or cystic fibrosis) in a patient in need of such treatment comprising administering to said patient a therapeutically effective amount of at least one compound (usually 1) of formula I; in combination with at least one (usually 1) compound selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

This invention also provides a method of treating multiple sclerosis in a patient in need of such treatment comprising administering to said patient, a therapeutically effective amount of at least one (usually 1) compound of formula I in combination with at least one compound selected from the group consisting of glatiramer acetate, glucocorticoids, methotrexate, azothioprine, mitoxantrone, chemokine inhibitors, and CB2-selective inhibitors.

This invention also provides a method of treating multiple sclerosis in a patient in need of such treatment comprising administering to said patient a therapeutically effective amount of at least one (usually 1) compound of formula I, in combination with at least one compound selected from the group consisting of: methotrexate, cyclosporin, leflunimide, sulfasalazine, β-methasone, β-interferon, glatiramer acetate, prednisone, etonercept, and infliximab.

This invention also provides a method of treating rheumatoid arthritis in a patient in need of such treatment comprising administering to said patient a therapeutically effective amount of at least one (usually 1) compound of formula I in combination with at least one compound selected from the group consisting of COX-2 inhibitors, COX inhibitors, immunosuppressives (e.g., methotrexate, cyclosporin, leflunimide and sulfasalazine), steroids (e.g., betamethasone, cortisone and dexamethasone), PDE IV inhibitors, anti-TNF-α compounds, MMP inhibitors, glucocorticoids, chemokine inhibitors, CB2-selective inhibitors, and other classes of compounds indicated for the treatment of rheumatoid arthritis.

This invention also provides a method of treating stroke and cardiac reperfusion injury in a patient in need of such treatment comprising administering to said patient a therapeutically effective amount of at least one compound (usually 1) of formula I in combination with at least one compound selected from the group consisting of thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of rheumatoid arthritis.

This invention also provides a method of treating stroke and cardiac reperfusion injury in a patient in need of such treatment comprising administering to said patient a therapeutically effective amount of at least one (usually 1) compound of formula I in combination with at least one compound selected from the group consisting of tenecteplase, TPA, alteplase, abciximab, eftiifbatide, and heparin.

This invention also provides a method of treating psoriasis in a patient in need of such treatment comprising administering to said patient a thereapeutically effective amount of at least one (usually 1) compound of formula I in combination with at least one compound selected from the group consisting of immunosuppressives (e.g., methotrexate, cyclosporin, leflunimide and sulfasalazine), steroids (e.g., β-methasone) and anti-TNF-α compounds (e.g., etonercept and infliximab).

This invention also provides a pharmaceutical composition comprising at least one (usually 1) compound of formula I and a pharmaceutically acceptable carrier.

This invention also provides a pharmaceutical composition comprising at least one (usually 1) compound of formula I, and at least one (usually 1) other agent, medicament, antibody and/or inhibitor disclosed above, and a pharmaceutically acceptable carrier.

DETAILED DESCRIPTION OF THE PREFERRED EMBODIMENTS

Unless indicated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

When any variable (e.g., aryl, $R^2$) occurs more than one time in any constituent, its definition on each occurrence is independent of its definition at every other occurrence. Also, combinations of substituents and/or variables are permissible only if such combinations result in stable compounds.

"An effective amount" means a therapeutically acceptable amount (i.e., that amount which provides the desired therapeutic effective).

"At least one" means one or more (e.g., 1–3, 1–2, or 1).

"Composition" is intended to encompass a product comprising the specified ingredients in the specified amounts, as well as any product which results, directly or indirectly, from combination of the specified ingredients in the specified amounts.

"In combination with" as used to describe the administration of a compound of formula I with other medicaments in the methods of treatment of this invention, means that the compounds of formula I and the other medicaments are administered sequentially or concurrently in separate dosage forms, or are administered concurrently in the same dosage form.

"Mammal" includes a human being, and preferably means a human being.

"One or more" means at least one (e.g., 1–3, 1–2 or 1).

"Patient" includes both human and other mammals, preferably human.

"Prodrug" represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

"Alkyl" means a straight or branched saturated hydrocarbon chain having 1 to 20 carbon atoms, preferably 1 to 12 carbon atoms, more preferably 1 to 6 carbon atoms.

"Alkoxy" means an alkyl-O-group wherein alkyl is as defined above. Non-limiting examples of alkoxy groups include: methoxy, ethoxy, n-propoxy, iso-propoxy and n-butoxy. The bond to the parent moiety is through the ether oxygen.

"Alkenyl" means a straight or branched aliphatic hydrocarbon group having at least one carbon-carbon double bond, and 2 to 20 carbon atoms, preferably 2 to 12 carbon atoms, and more preferably 2 to 6 carbon atoms. Non-limiting examples of alkenyl groups include: ethenyl, propenyl, n-butenyl, 3-methylbut-2-enyl, n-pentenyl, octenyl and decenyl.

"Alkynyl" means a straight or branched aliphatic hydrocarbon group having at least one carbon-carbon triple bond, and 2 to 15 carbon atoms, preferably 2 to 12 carbon atoms, and more preferably 2 to 4 carbon atoms. Non-limiting examples of alkynyl groups include ethynyl, propynyl, 2-butynyl, 3-methylbutynyl, n-pentynyl, and decynyl.

"Aryl" means an aromatic monocyclic or multicyclic ring system, wherein at least one ring is aromatic, comprising about 6 to about 14 carbon atoms, and preferably about 6 to about 10 carbon atoms. Non-limiting examples of suitable aryl groups include: phenyl, naphthyl, indenyl, tetrahydronaphthyl, indanyl, anthracenyl, and fluorenyl. The aryl group can be unsubstituted or substituted with one, two, or three substituents independently selected from the group consisting of: lower alkyl, halo, cyano, nitro, haloalkyl, hydroxy, alkoxy, carboxy, carboxyalkyl, carboxamide, mercapto, sulfhydryl, amino, alkylamino, dialkylamino, sulfonyl, sulfonamido, aryl and heteroaryl.

"Arylalkyl" means an aryl group, as defined above, bound to an alkyl group, as defined above, wherein the alkyl group is bound to the parent moiety. Non-limiting examples of suitable arylalkyl groups include benzyl, phenethyl and naphthleneylmethyl.

"Cycloalkyl" means saturated carbocyclic rings having 3 to 10 (e.g., 3 to 7) carbon atoms, preferably 5 to 10 carbon atoms, and more preferably 5 to 7 carbon atoms, and having one to three rings. Non-limiting examples of cycloalkyl groups include: cyclopropyl, cyclopentyl, cyclohexyl, cycloheptyl, norbornyl, and adamantyl.

"Cycloalkylalkyl" means a cycloalkyl group bound to the parent moiety through an alkyl group. Non-limiting examples include: cyclopropylmethyl and cyclohexylmethyl.

"Cycloalkenyl" means a non-aromatic mono or multicyclic ring system comprising 3 to 10 carbon atoms, and preferably 5 to 10 carbon atoms, and having at least one carbon-carbon double bond. Preferred cycloalkenyl rings have 5 to 7 carbon atoms. Non-limiting examples of cycloalkyl groups include cyclopentenyl, cyclohexenyl, cycloheptenyl, and norbornenyl.

"Fluoroalkyl" represents a straight or branched saturated hydrocarbon chain (e.g., a carbon chain comprising 1–20 carbon atoms), substituted with one or more fluorine atoms.

"Halo" means fluoro, chloro, bromo, or iodo groups.

"Haloalkyl" means an alkyl group as defined above wherein one or more hydrogen atoms on the alkyl is replaced by a halo group defined above.

"Halogen" means fluorine, chlorine, bromine or iodine.

"Heteroaryl" refers to a 5 to 14, preferably 5 to 10 membered single or benzofused aromatic rings consisting of 1 to 3 heteroatoms independently selected from the group consisting of —O—, —S—, and —N═, provided that the rings do not possess adjacent oxygen and/or sulfur atoms. Preferred heteroaryls contain 5 to 6 ring atoms. A nitrogen atom of a heteroaryl can be optionally oxidized to the corresponding N-oxide. The heteroaryl group can be unsubstituted or substituted with one, two, or three substituents independently selected from lower alkyl, halo, cyano, nitro, haloalkyl, hydroxy, alkoxy, carboxy, carboxyalkyl, carboxamide, sulfhydryl, amino, alkylamino and dialkylamino. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl.

"Heteroarylalkyl" means a heteroaryl group, as defined above, bound to an alkyl group, as defined above, where the bond to the parent moiety is through the alkyl group.

"Heterocyclic acidic functional group" is intended to include groups such as, pyrrole, imidazole, triazole, tetrazole, and the like.

"Heterocyclyl" or "heterocyclic" or "heterocycloalkyl" means a non-aromatic saturated monocyclic or multicyclic ring system (i.e., a saturated carbocyclic ring or ring system) comprising 3 to 10 ring atoms (e.g., 3 to 7 ring atoms), preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls have 5 to 6 ring atoms. The nitrogen or sulfur atom of the heterocyclyl can be optionally oxidized to the corresponding N-oxide, S-oxide or S,S-dioxide. Examples include, but are not limited to: oxirane, oxetanyl, tetrahydropyridinyl, tetrahydropyrimidinyl, hydantoin, valerolactam, pyrrolidinone, piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, and tetrahydrothiopyranyl.

N-oxides can form on a tertiary nitrogen present in an R substituent, or on =N— in a heteroaryl ring substituent and are included in the compounds of formula (I).

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine ($Et_3N$); diethyl ether ($Et_2O$); ethyl chloroformate ($ClCO_2Et$); and 1-(3-dimethylaminopropyl)-3-ethyl carbodiimide hydrochloride (DEC).

The novel compounds of this invention are represented by the formula (I):

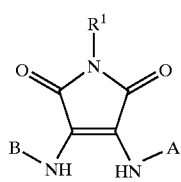

(I)

or a pharmaceutically acceptable salt or solvate thereof:

$R^1$ is selected from H, aryl, heteroaryl, alkyl, arylalkyl, heteroarylalkyl, cycloalkyl, heterocycloalkyl, cycloalkylalkyl, and heterocycloalkylalkyl optionally substituted with one or more substituents selected from the group consisting of:

a) H,
b) halogen,
c) —$CF_3$,
d) —$COR^{13}$,
e) —OH,
f) —$NR^{13}R^{14}$,
g) —$NO_2$,
h) cyano,
i) —$SO_2OR^{13}$,
j) —Si(alkyl),
k) —Si(aryl),
l) —$CO_2R^{13}$,
m) —$CONR^{13}R^{14}$,
n) —$SO_2NR^{13}R^{14}$,
o) —$SO_2R^{13}$,
p) —$OR^{13}$,
q) —$NR^{13}R^{14}$,
r) —$O(C=O)R^{13}$,
s) —$O(C=O)NR^{13}R^{14}$,
t) —$NR^{13}COR^{14}$ and
u) —$NR^{13}CO_2R^{14}$;

A is selected from the group consisting of:

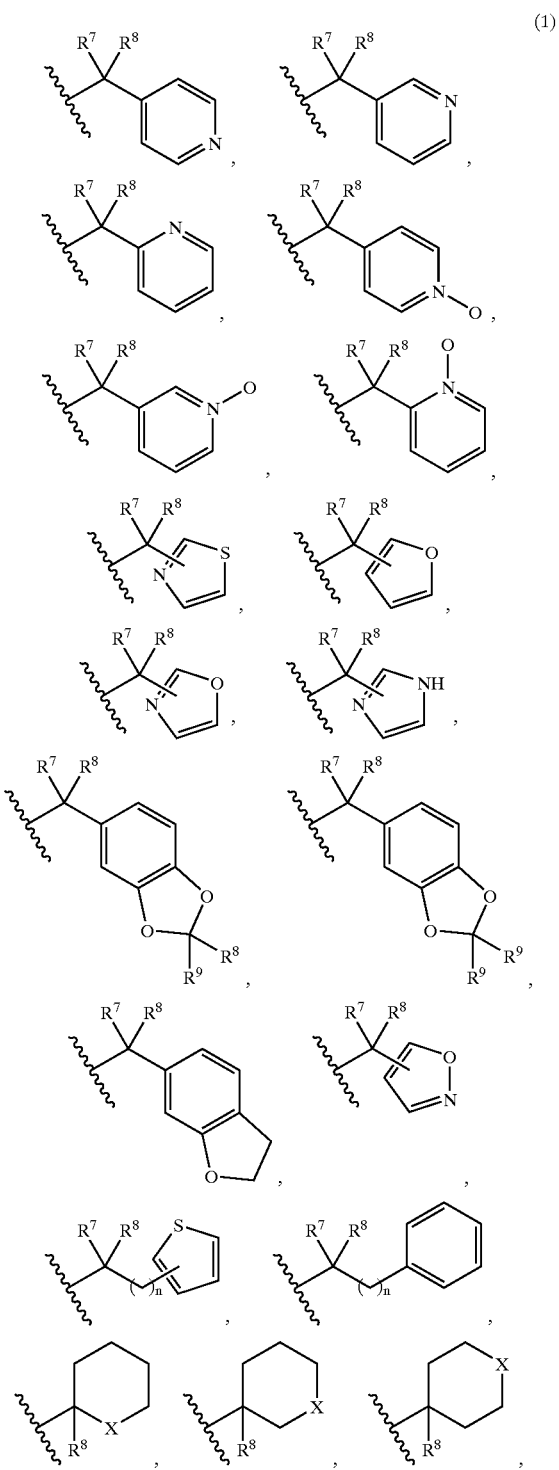

(1)

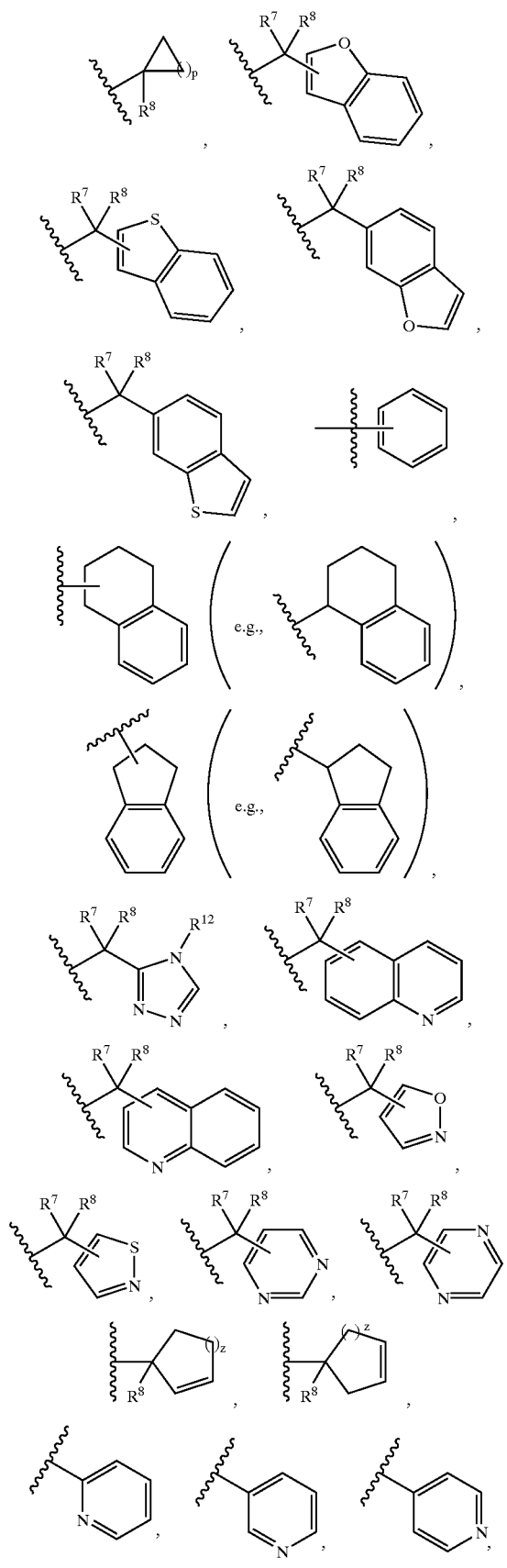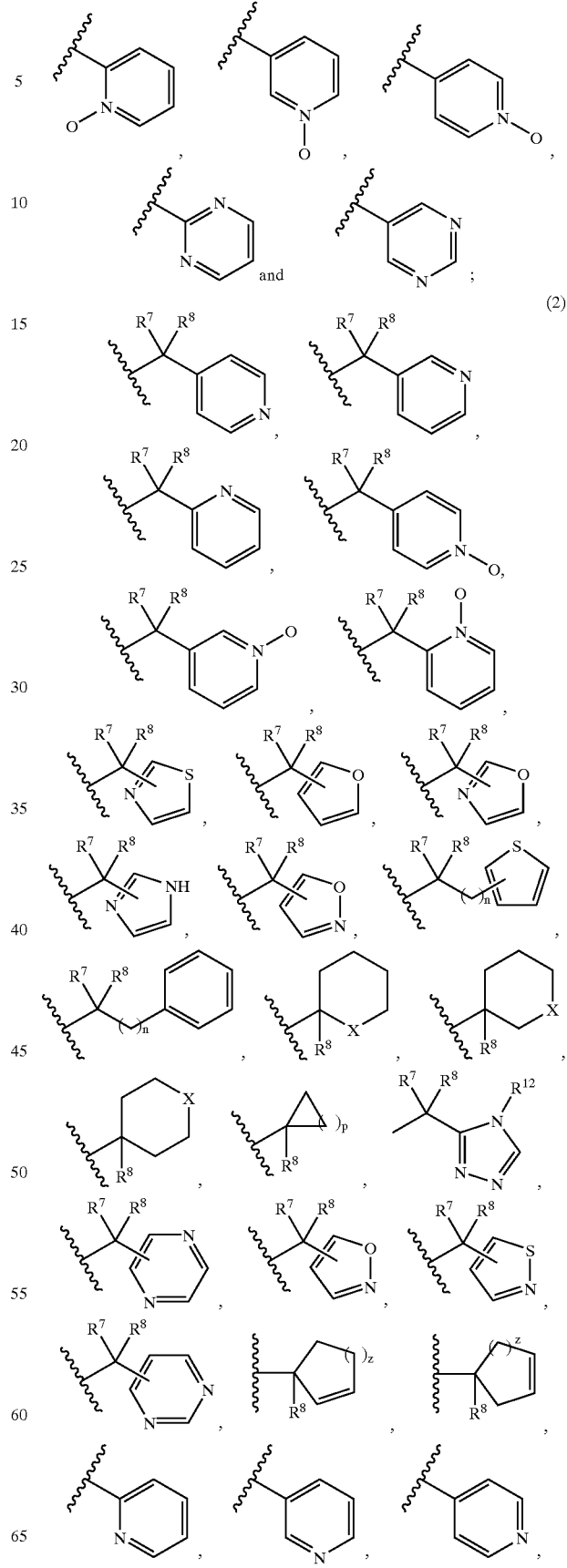

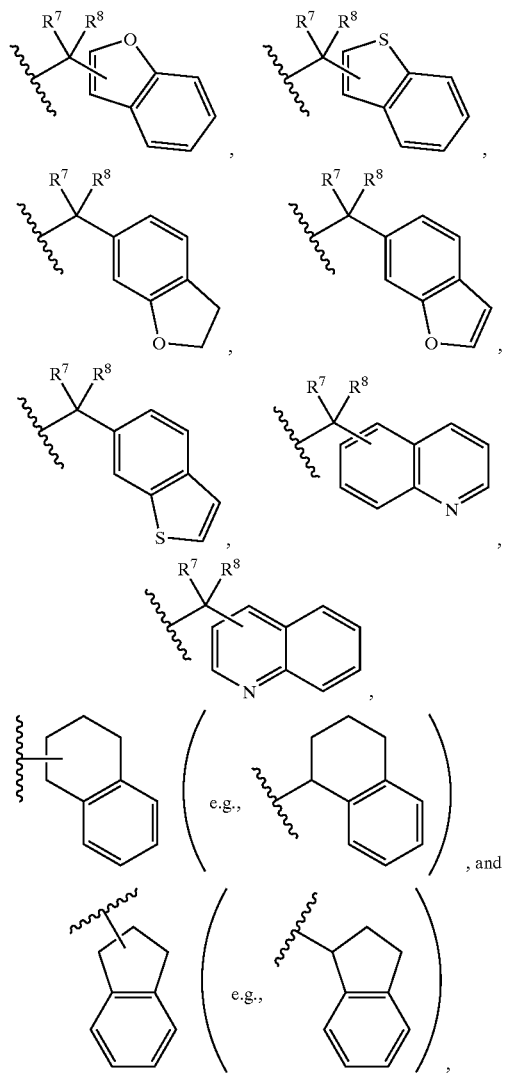

wherein the above rings of said A groups are substituted with 1 to 6 substituents each independently selected from the group consisting of: $R^9$ groups;

wherein one or both of the above rings of said A groups are substituted with 1 to 6 substituents each independently selected from the group consisting of: $R^9$ groups;

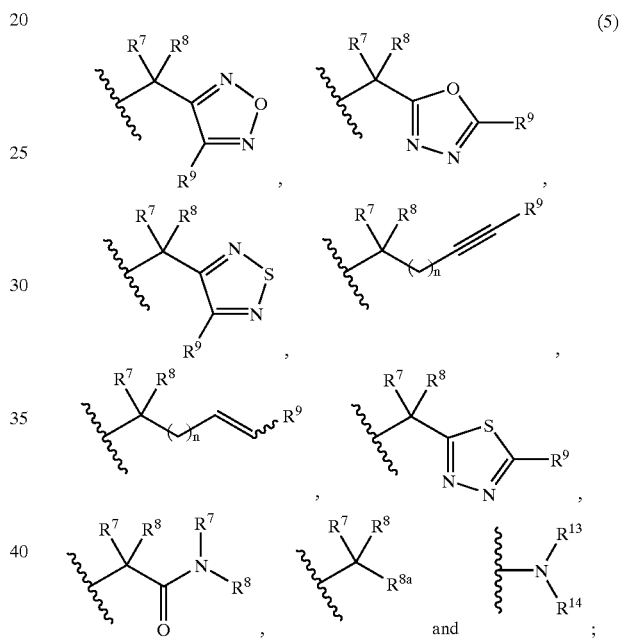

wherein the above phenyl rings of said A groups are substituted with 1 to 3 substituents each independently selected from the group consisting of: $R^9$ groups; and B is selected from the group consisting of

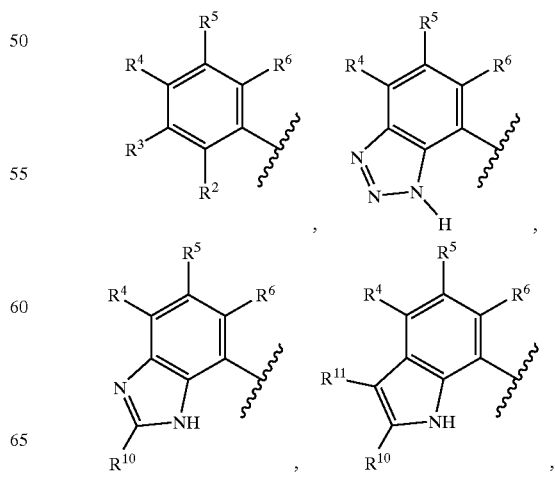

-continued

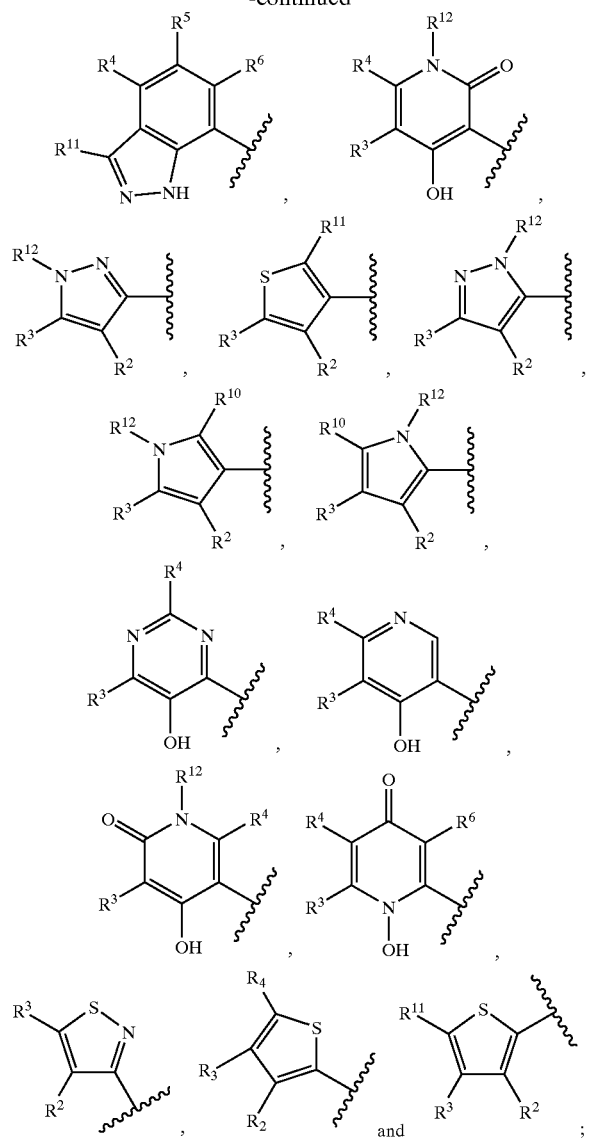

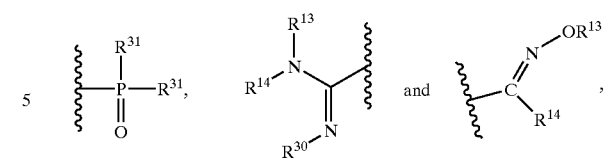

wherein there are 1 to 6 substituents on said substituted aryl group and each substituent is independently selected from the group consisting of: $R^9$ groups; and wherein there are 1 to 6 substituents on said substituted heteroaryl group and each substituent is independently selected from the group consisting of: $R^9$ groups;

each $R^5$ and $R^6$ are the same or different and are independently selected from the group consisting of hydrogen, halogen, alkyl, alkoxy, —$CF_3$, —$OCF_3$, —$NO_2$, —$C(O)R^{13}$, —$C(O)OR^{13}$, —$C(O)NR^{13}R^{14}$, —$SO_{(t)}NR^{13}R^{14}$, —$C(O)NR^{13}OR^{14}$, cyano, unsubstituted or substituted aryl, and unsubstituted or substituted heteroaryl group; wherein there are 1 to 6 substituents on said substituted aryl group and each substituent is independently selected from the group consisting of: $R^9$ groups; and wherein there are 1 to 6 substituents on said substituted heteroaryl group and each substituent is independently selected from the group consisting of: $R^9$ groups;

each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, alkynyl, alkenyl, and cycloalkenyl; and wherein there are one or more (e.g., 1 to 6) substituents on said substituted $R^7$ and $R^8$ groups, wherein each substitutent is independently selected from the group consisting of:

a) halogen,
b) —$CF_3$,
c) —$COR^{13}$,
d) —$OR^{13}$,
e) —$NR^{13}R^{14}$,
f) —$NO_2$,
g) —$CN$,
h) —$SO_2OR^{13}$,
i) —$Si(alkyl)_3$, wherein each alkyl is independently selected,
j) —$Si(aryl)_3$, wherein each alkyl is independently selected,
k) —$(R^{13})_2R^{14}Si$, wherein each $R^{13}$ is independently selected,
l) —$CO_2R^{13}$,
m) —$C(O)NR^{13}R^{14}$,
n) —$SO_2NR^{13}R^{14}$,
o) —$SO_2R^{13}$,
p) —$OC(O)R^{13}$,
q) —$OC(O)NR^{13}R^{14}$,
r) —$NR^{13}C(O)R^{14}$, and
s) —$NR^{13}CO_2R^{14}$;

(fluoroalkyl is one non-limiting example of an alkyl group that is substituted with halogen);

$R^{8a}$ is selected from the group consisting of: hydrogen, alkyl, cycloalkyl and cycloalkylalkyl;

n is 0 to 6;
p is 1 to 5;
X is O, NH, or S;
Z is 1 to 3;

$R^2$ is selected from the group consisting of: hydrogen, OH, —C(O)OH, —SH, —$SO_2NR^{13}R^{14}$, —$NHC(O)R^{13}$, —$NHSO_2NR^{13}R^{14}$, —$NHSO_2R^{13}$, —$NR^{13}R^{14}$, —$C(O)NR^{13}R^{14}$, —$C(O)NHOR^{13}$, —$C(O)NR^{13}OH$, —$S(O_2)OH$, —$OC(O)R^{13}$, an unsubstituted heterocyclic acidic functional group, and a substituted heterocyclic acidic functional group; wherein there are 1 to 6 substituents on said substituted heterocyclic acidic functional group each substituent being independently selected from the group consisting of: $R^9$ groups;

each $R^3$ and $R^4$ is independently selected from the group consisting of: hydrogen, cyano, halogen, alkyl, alkoxy, —OH, —$CF_3$, —$OCF_3$, —$NO_2$, —$C(O)R^{13}$, —$C(O)OR^{13}$, —$C(O)NHR^{17}$, —$C(O)NR^{13}R^{14}$, —$SO_{(t)}NR^{13}R^{14}$, —$SO_{(t)}R^{13}$, —$C(O)NR^{13}OR^{14}$, unsubstituted or substituted aryl, unsubstituted or substituted heteroaryl, each $R^9$ is independently selected from the group consisting of:
a) $-R^{13}$,
b) halogen,
c) $-CF_3$,
d) $-COR^{13}$,
e) $-OR^{13}$,
f) $-NR^{13}R^{14}$,
g) $-NO_2$,
h) $-CN$,
i) $-SO_2R^{13}$,
j) $-SO_2NR^{13}R^{14}$,
k) $-NR^{13}COR^{14}$,
l) $-CONR^{13}R^{14}$,
m) $-NR^{13}CO_2R^{14}$,
n) $-CO_2R^{13}$,
o)

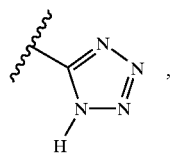

p) alkyl substituted with one or more (e.g., one) $-OH$ groups (e.g., $-(CH_2)_qOH$, wherein q is 1–6, usually 1 to 2, and preferably 1),
q) alkyl substituted with one or more (e.g., one) $-NR^{13}R^{14}$ group (e.g., $-(CH_2)_qNR^{13}R^{14}$, wherein q is 1–6, usually 1 to 2, and preferably 1), and
r) $-N(R^{13})SO_2R^{14}$ (e.g., $R^{13}$ is H and $R^{14}$ is alkyl, such as methyl);

each $R^{10}$ and $R^{11}$ is independently selected from the group consisting of $R^{13}$, (e.g., hydrogen and alkyl (e.g., $C_1$ to $C_6$ alkyl, such as methyl)), halogen, $-CF_3$, $-OCF_3$, $-NR^{13}R^{14}$, $-NR^{13}C(O)NR^{13}R^{14}$, $-OH$, $-C(O)OR^{13}$, $-SH$, $-SO_{(t)}NR^{13}R^{14}$, $-SO_2R^{13}$, $-NHC(O)R^{13}$, $-NHSO_2NR^{13}R^{14}$, $-NHSO_2R^{13}$, $-C(O)NR^{13}R^{14}$, $-C(O)NR^{13}OR^{14}$, $-OC(O)R^{13}$ and cyano;

$R^{12}$ is selected from the group consisting of: hydrogen, $-C(O)OR^{13}$, unsubstituted or substituted aryl, unsubstituted or substituted heteroaryl, unsubstituted or substituted arylalkyl, unsubstituted or substituted cycloalkyl, unsubstituted or substituted alkyl, unsubstituted or substituted cycloalkylalkyl, and unsubstituted or substituted heteroarylalkyl group; wherein there are 1 to 6 substituents on the substituted $R^{12}$ groups and each substituent is independently selected from the group consisting of: $R^9$ groups;

each $R^{13}$ and $R^{14}$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, unsubstituted or substituted heterocyclic, unsubstituted or substituted fluoroalkyl, and unsubstituted or substituted heterocycloalkylalkyl (wherein "heterocyloalkyl" means heterocyclic); wherein there are 1 to 6 substituents on said substituted $R^{13}$ and $R^{14}$ groups and each substituent is independently selected from the group consisting of: alkyl, $-CF_3$, $-OH$, alkoxy, aryl, arylalkyl, fluroalkyl, cycloalkyl, cycloalkylalkyl, heteroaryl, heteroarylalkyl, $-N(R^{40})_2$, $-C(O)OR^{15}$, $-C(O)NR^{15}R^{16}$, $-S(O)_tNR^{15}R^{16}$, $-C(O)R^{15}$, $-SO_2R^{15}$ provided that $R^{15}$ is not H, halogen, and $-NHC(O)NR^{15}R^{16}$; or $R^{13}$ and $R^{14}$ taken together with the nitrogen they are attached to in the groups $-C(O)NR^{13}R^{14}$ and $-SO_2NR^{13}R^{14}$ form an unsubstituted or substituted saturated heterocyclic ring (preferably a 3 to 7 membered heterocyclic ring), said ring optionally containing one additional heteroatom selected from the group consisting of: O, S and $NR^{18}$; wherein there are 1 to 3 substituents on the substituted cyclized $R^{13}$ and $R^{14}$ groups (i.e., there is 1 to 3 substituents on the ring formed when the $R^{13}$ and $R^{14}$ groups are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, $-C(O)OR^{15}$, $-C(O)NR^{15}R^{16}$, $-SO_tNR^{15}R^{16}$, $-C(O)R^{15}$, $-SO_2R^{15}$ provided that $R^{15}$ is not H, $-NHC(O)NR^{15}R^{16}$, $-NHC(O)OR^{15}$, halogen, and a heterocycloalkenyl group (i.e., a heterocyclic group that has at least one, and preferably one, double bond in a ring, e.g.,

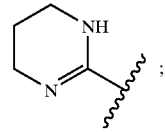

each $R^{15}$ and $R^{16}$ is independently selected from the group consisting of: H, alkyl, aryl, arylalkyl, cycloalkyl and heteroaryl;

$R^{17}$ is selected from the group consisting of: $-SO_2$alkyl, $-SO_2$aryl, $-SO_2$cycloalkyl, and $-SO_2$heteroaryl;

$R^{18}$ is selected from the group consisting of: H, alkyl, aryl, heteroaryl, $-C(O)R^{19}$, $-SO_2R^{19}$ and $-C(O)NR^{19}R^{20}$;

each $R^{19}$ and $R^{20}$ is independently selected from the group consisting of: alkyl, aryl and heteroaryl;

$R^{30}$ is selected from the group consisting of: alkyl, cycloalkyl, $-CN$, $-NO_2$, or $-SO_2R^{15}$ provided that $R^{15}$ is not H;

each $R^{31}$ is independently selected from the group consisting of: unsubstituted alkyl, unsubstituted or substituted aryl, unsubstituted or substituted heteroaryl and unsubstituted or substituted cycloalkyl; wherein there are 1 to 6 substituents on said substituted $R^{31}$ groups and each substituent is independently selected from the group consisting of: alkyl, halogen and $-CF_3$;

each $R^{40}$ is independently selected from the group consisting of: H, alkyl and cycloalkyl; and t is 0, 1 or 2.

One embodiment of this invention is directed to the prodrugs of formula I and to the prodrugs of the pharmaceutically acceptable salts and solvates of formula I In one embodiment of the this invention, when $R^3$ in formula I is $-SO_{(t)}NR^{13}R^{14}$ (e.g., $-SO_2NR^{13}R^{14}$), $R^{13}$ and $R^{14}$ are independently selected from the group consisting of: H and alkyl (e.g., methyl, ethyl, isopropyl and t-butyl). Examples include, but are not limited to (1) $-SO_2NH_2$ and (2) $-SO_2NR^{13}R^{14}$ wherein $R^{13}$ and $R^{14}$ are the same or different alkyl group (e.g., methyl, ethyl, isopropyl and t-butyl), e.g., the same alkyl group, such as, for example $-SO_2N(CH_3)_2$.

In another embodiment of this invention, when $R^3$ in formula I is $-C(O)NR^{13}R^{14}$, $R^{13}$ and $R^{14}$ are independently selected from the group consisting of: H and alkyl (e.g., methyl, ethyl, isopropyl and t-butyl). Examples include, but are not limited to —C(O)NR$^{13}$R$^{14}$ wherein each R$^{13}$ and R$^{14}$ are the same or different alkyl group, e.g., the same alkyl group, such as, for example —C(O)N(CH$_3$)$_2$.

In another embodiment of this invention substituent A in formula I is selected from the group consisting of:

(1) unsubstituted or substituted:

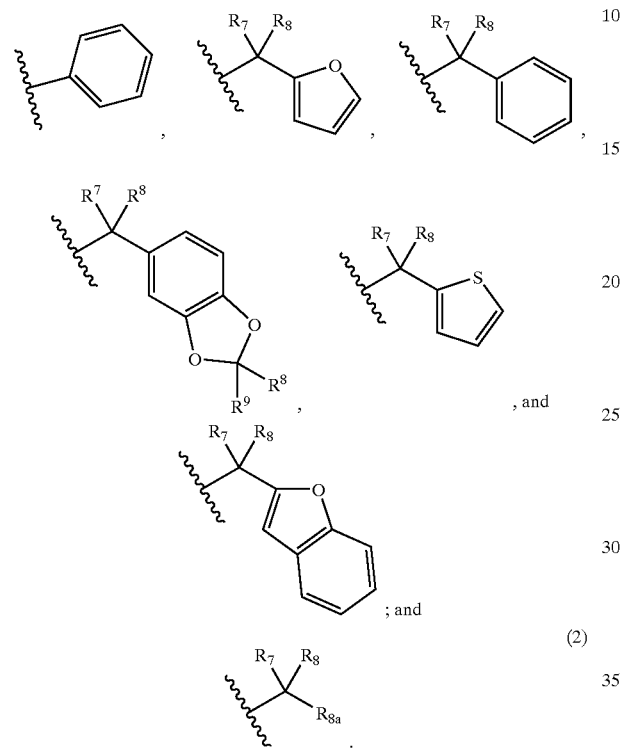

(2)

In another embodiment of this invention substituent A in formula I is selected from the group consisting of:

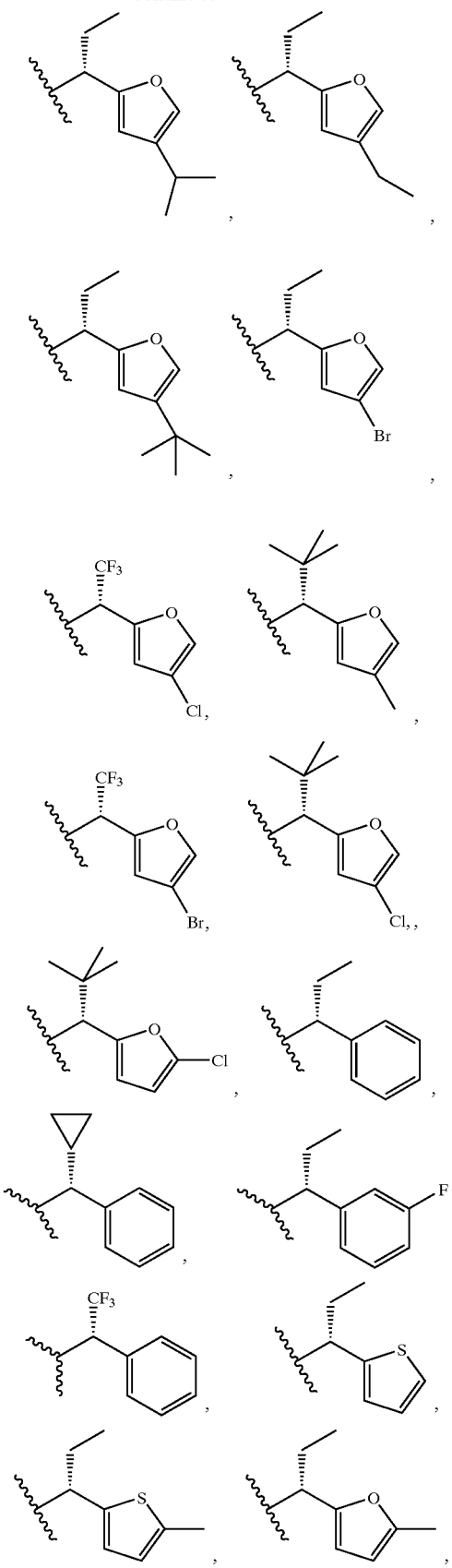

-continued

-continued
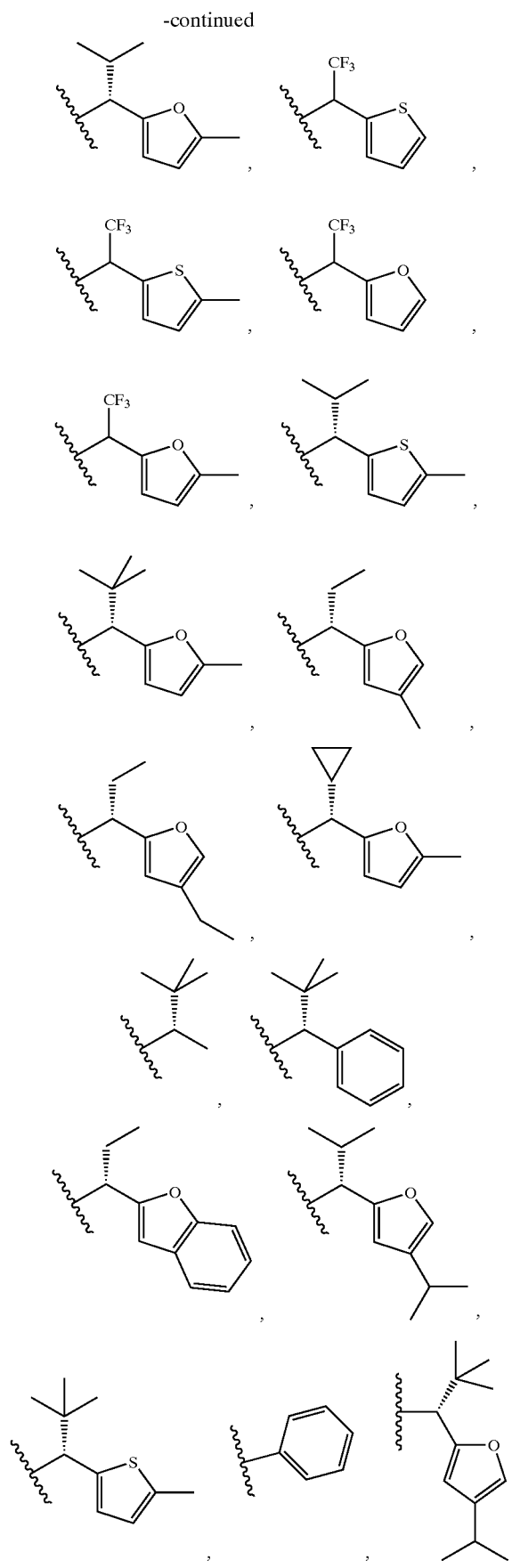
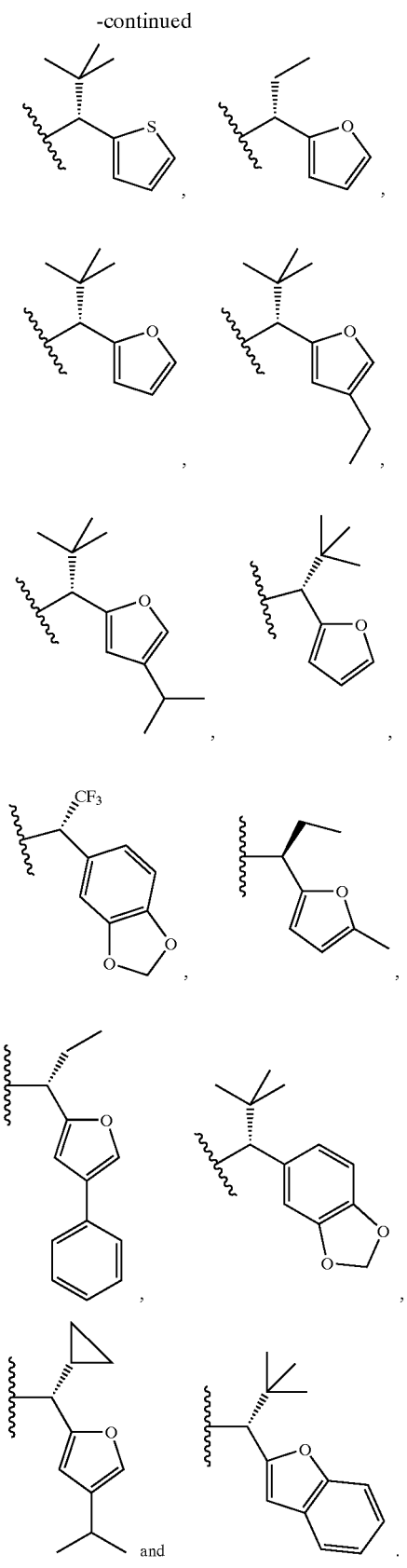
In another embodiment of this invention substituent A in formula I is selected from the group consisting of:

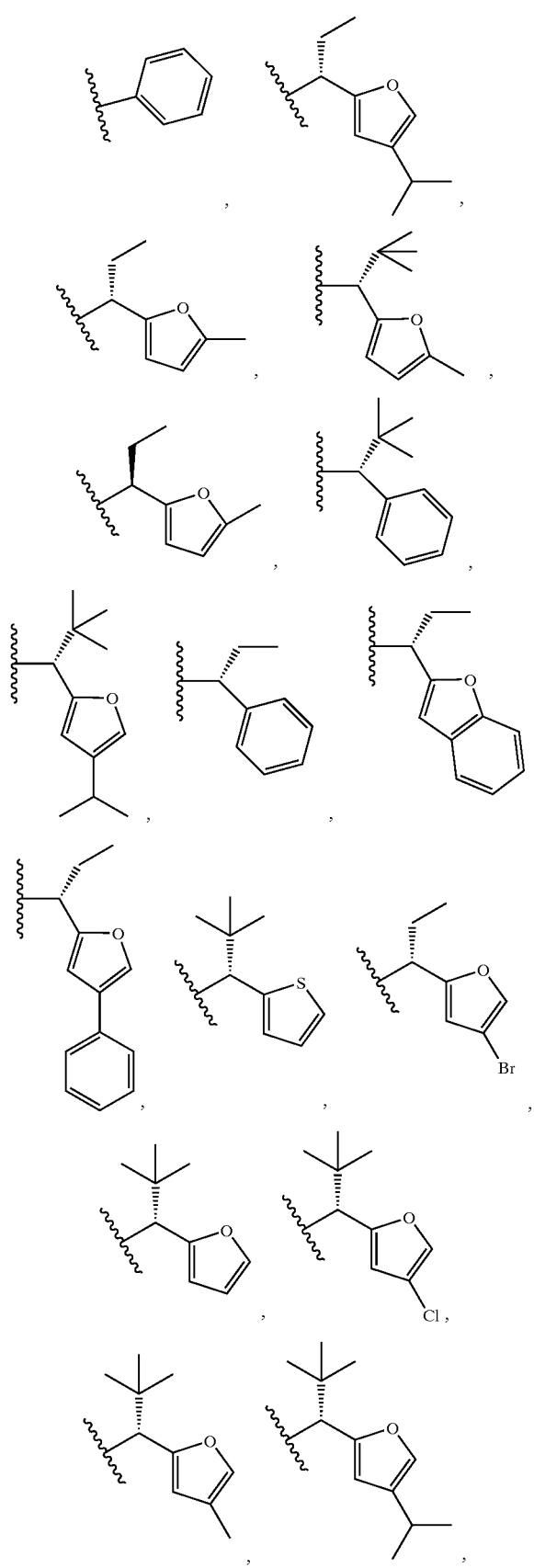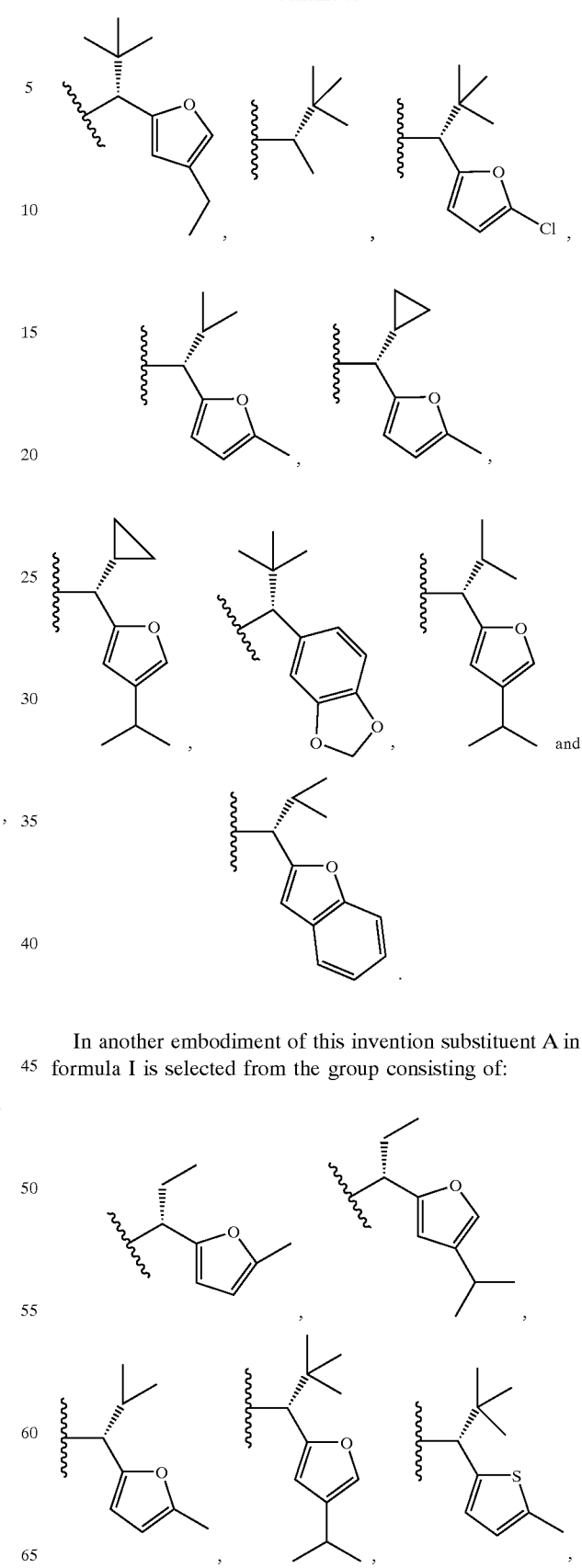
In another embodiment of this invention substituent A in formula I is selected from the group consisting of:

-continued

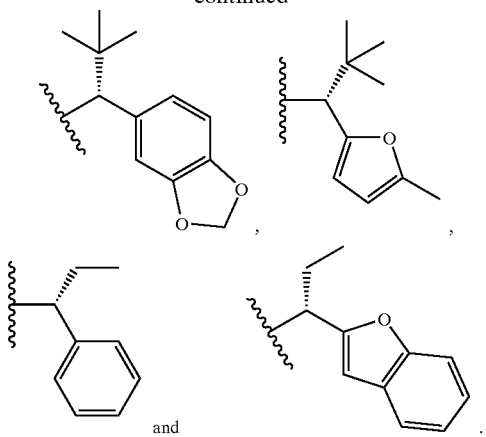

and

In another embodiment of this invention substituent B in formula I is selected from the group consisting of:

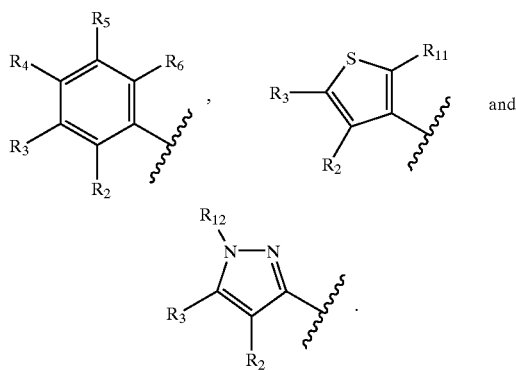

In another embodiment of this invention substituent B in formula I is:

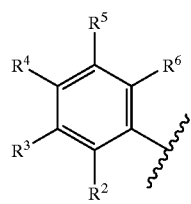

and all other substitutents are as defined for of formula I.

In another embodiment of this invention substituent B in formula I is:

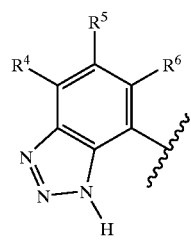

and all other substitutents are as defined for of formula I.

In another embodiment of this invention substituent B in formula I is:

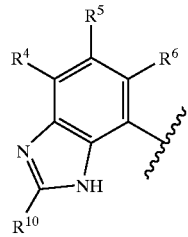

and all other substitutents are as defined for of formula I.

In another embodiment of this invention substituent B in formula I is:

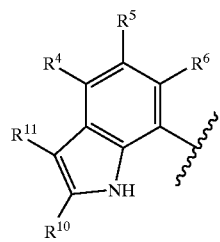

and all other substitutents are as defined for of formula I.

In another embodiment of this invention substituent B in formula I is:

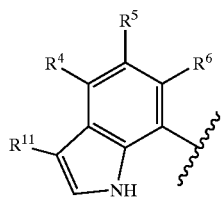

and all other substitutents are as defined for of formula I.

In another embodiment of this invention substituent B in formula I is:

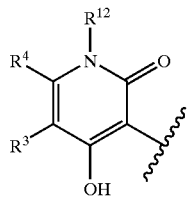

and all other substitutents are as defined for of formula I.

In another embodiment of this invention substituent B in formula I is:

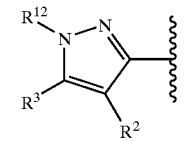

and all other substitutents are as defined for of formula I.

In another embodiment of this invention substituent B in formula I is:

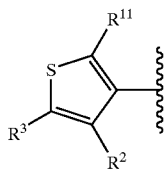

and all other substitutents are as defined for of formula I.

In another embodiment of this invention substituent B in formula I is:

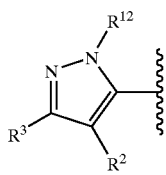

and all other substitutents are as defined for of formula I.

In another embodiment of this invention substituent B in formula I is:


and all other substitutents are as defined for of formula I.

In another embodiment of this invention substituent B in formula I is:

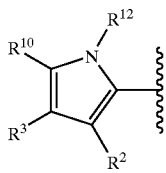

and all other substitutents are as defined for of formula I.

In another embodiment of this invention substituent B in formula I is:

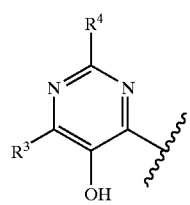

and all other substitutents are as defined for of formula I.

In another embodiment of this invention substituent B in formula I is:

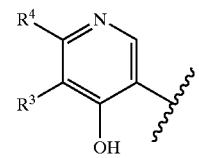

and all other substitutents are as defined for of formula I.

In another embodiment of this invention substituent B in formula I is:

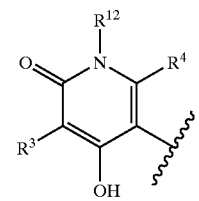

and all other substitutents are as defined for of formula I.

In another embodiment of this invention substituent B in formula I is:

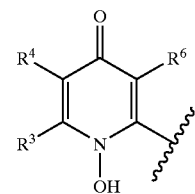

and all other substitutents are as defined for of formula I.

In another embodiment of this invention substituent B in formula I is:

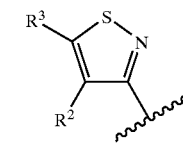

and all other substitutents are as defined for of formula I.

In another embodiment of this invention substituent B in formula I is:

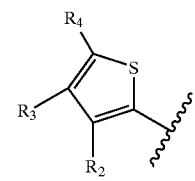

and all other substitutents are as defined for of formula I.

In another embodiment of this invention substituent B in formula I is:

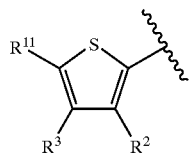

and all other substitutents are as defined for of formula I.

In another embodiment of this invention substituent B in formula I is selected from the group consisting of:

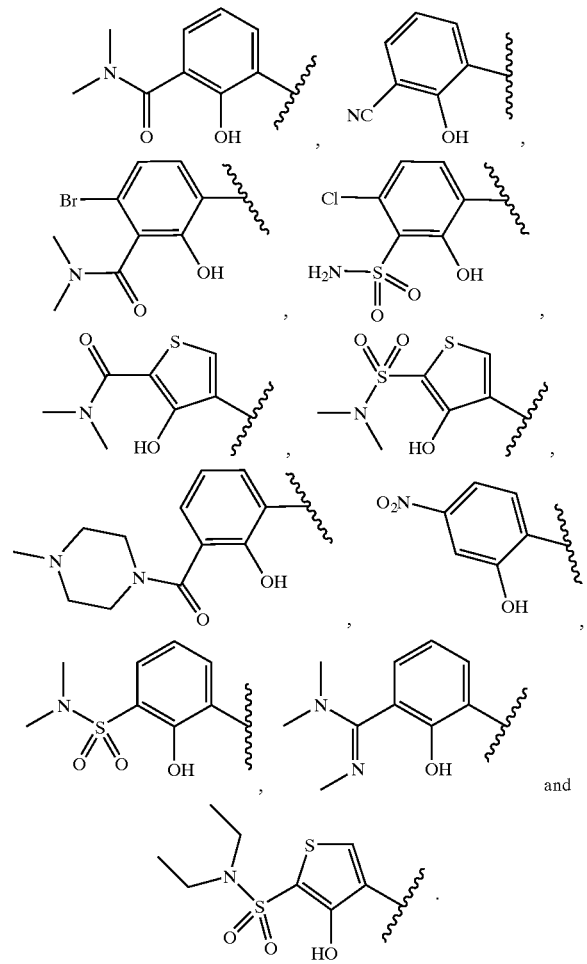

In another embodiment of this invention substituent B in formula I is selected from the group consisting of:

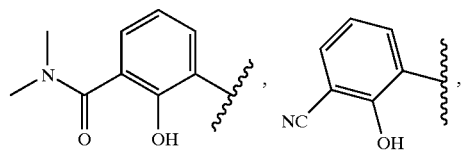

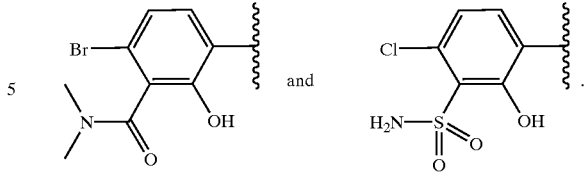

In another embodiment of this invention B is:

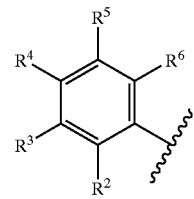

and R³ for this B group is selected from the group consisting of: —C(O)NR¹³R¹⁴,

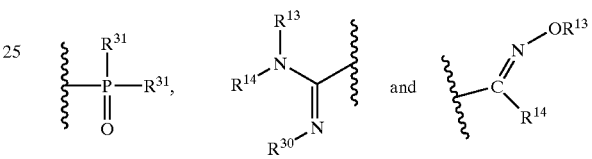

and all other substituents are as defined for formula I.

In another embodiment of this invention substituent B in formula I is:

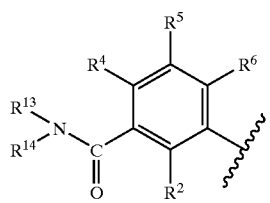

and all other substituents are as defined for formula I.

In another embodiment of this invention substituent B is:

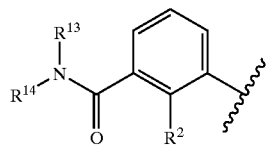

wherein R² is —OH, and all other substituents are as defined for formula I.

In another embodiment of this invention substituent B in formula I is:

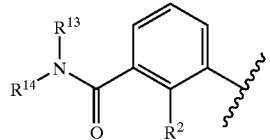

wherein R² is —OH, and R¹³ and R¹⁴ are independently selected from the group consisting of H and alkyl (e.g., methyl, ethyl, isopropyl and t-butyl).

In another embodiment of this invention substituent B in formula I is:

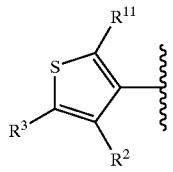

wherein $R^{11}$ is H, and all other substituents are as defined for formula I.

In another embodiment of this invention substituent B in formula I is:

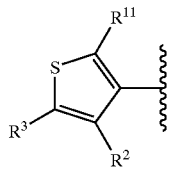

wherein $R^2$ is —OH, and all other substituents are as defined for formula I.

In another embodiment of this invention substituent B in formula I is:

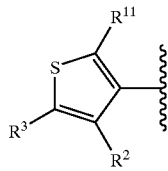

wherein $R^3$ is —C(O)NR$^{13}$R$^{14}$, and all other substituents are as defined for formula I.

In another embodiment of this invention substituent B in formula I is:

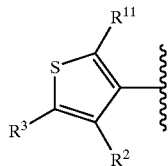

wherein $R^3$ is —S(O)$_t$NR$^{13}$R$^{14}$, and all other substituents are as defined for formula I.

In another embodiment of this invention substituent B in formula I is:

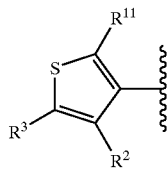

wherein $R^2$ is —OH, and $R^3$ is —C(O)NR$^{13}$R$^{14}$, and all other substituents are as defined for formula I.

In another embodiment of this invention substituent B in formula I is:

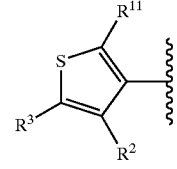

wherein $R^2$ is —OH, and $R^3$ is —S(O)$_t$NR$^{13}$R$^{14}$, and all other substituents are as defined for formula I.

In another embodiment of this invention substituent B in formula I is:

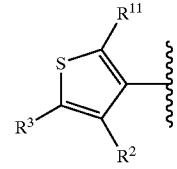

wherein $R^2$ is —OH, $R^3$ is —C(O)NR$^{13}$R$^{14}$, and $R^{11}$ is H, and all other substituents are as defined for formula I.

In another embodiment of this invention substituent B in formula I is:

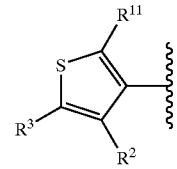

wherein $R^2$ is —OH, $R^3$ is —S(O)$_t$NR$^{13}$R$^{14}$, and $R^{11}$ is H, and all other substituents are as defined for formula I.

In another embodiment of this invention substituent B in formula I is selected from the group consisting of:

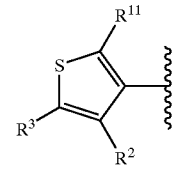

wherein $R^2$ is —OH, $R^3$ is —C(O)NR$^{13}$R$^{14}$, $R^{11}$ is H, and $R^{13}$ and $R^{14}$ are independently selected from the group consisting of: H, alkyl (e.g., methyl, ethyl, isopropyl and t-butyl), unsubstituted heteroaryl and substituted heteroaryl.

In another embodiment of this invention substituent B in formula I is:

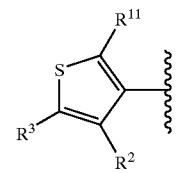

wherein $R^2$ is —OH, $R^3$ is —S(O)$_t$NR$^{13}$R$^{14}$, $R^{11}$ is H, and $R^{13}$ and $R^{14}$ are independently selected from the group consisting of H and alkyl (e.g., methyl, ethyl, isopropyl and t-butyl).

In another embodiment of this invention substituent B in formula I is:

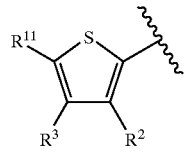

wherein $R^{11}$ is H, and all other substituents are as defined for formula I.

In another embodiment of this invention substituent B in formula I is:

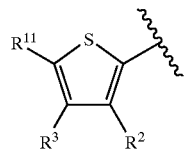

wherein $R^2$ is —OH, and all other substituents are as defined for formula I.

In another embodiment of this invention substituent B in formula I is:

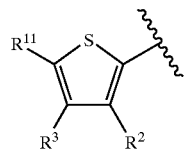

wherein $R^3$ is —C(O)NR$^{13}$R$^{14}$, and all other substituents are as defined for formula I.

In another embodiment of this invention substituent B in formula I is:

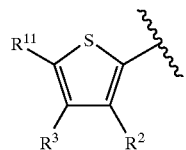

wherein $R^3$ is —S(O)$_t$NR$^{13}$R$^{14}$, and all other substituents are as defined for formula I.

In another embodiment of this invention substituent B in formula I is:

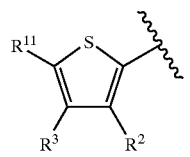

wherein $R^2$ is —OH, and $R^3$ is —C(O)NR$^{13}$R$^{14}$, and all other substituents are as defined for formula I.

In another embodiment of this invention substituent B in formula I is:

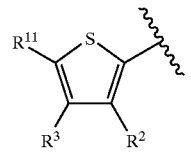

wherein $R^2$ is —OH, and $R^3$ is —S(O)$_t$NR$^{13}$R$^{14}$, and all other substituents are as defined for formula I.

In another embodiment of this invention substituent B in formula I is:

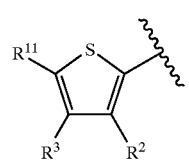

wherein $R^2$ is —OH, $R^3$ is —C(O)NR$^{13}$R$^{14}$, and $R^{11}$ is H, and all other substituents are as defined for formula I.

In another embodiment of this invention substituent B in formula I is:

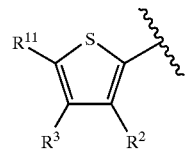

wherein $R^2$ is —OH, $R^3$ is —S(O)$_t$NR$^{13}$R$^{14}$, and $R^{11}$ is H, and all other substituents are as defined for formula I.

In another embodiment of this invention substituent B in formula I is:

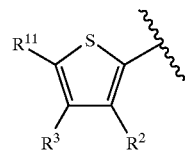

wherein $R^2$ is —OH, $R^3$ is —C(O)NR$^{13}$R$^{14}$, $R^{11}$ is H, and $R^{13}$ and $R^{14}$ are independently selected from the group consisting of: H, alkyl (e.g., methyl, ethyl, isopropyl and t-butyl), unsubstituted heteroaryl and substituted heteroaryl.

In another embodiment of this invention substituent B in formula I is:

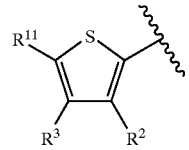

wherein $R^2$ is —OH, $R^3$ is —S(O)$_t$NR$^{13}$R$^{14}$, $R^{11}$ is H, and $R^{13}$ and $R^{14}$ are independently selected from the group consisting of H and alkyl (e.g., methyl, ethyl, isopropyl and t-butyl).

In another embodiment of this invention substituent B is selected from the group consisting of:

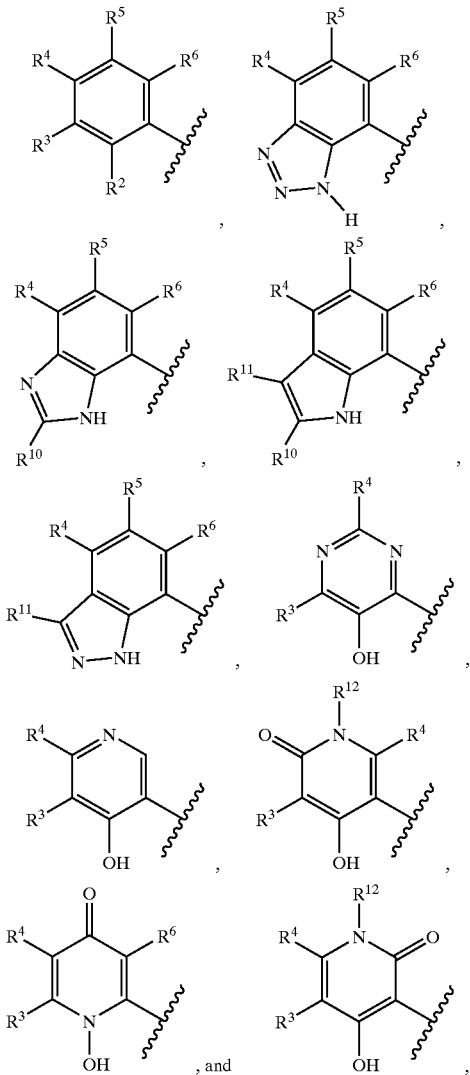

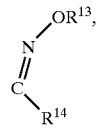, and wherein,

R² is hydrogen, OH, C(O)OH, SH, SO₂NR¹³R¹⁴, NHC(O)R¹³, NHSO₂NR¹³R¹⁴, NHSO₂R¹³, NR¹³R¹⁴, C(O)NR¹³R¹⁴, C(O)NHOR¹³, C(O)NR¹³OH, OC(O)R¹³ or an optionally substituted cyclic or heterocyclic acidic functional group, with the proviso that if R² is SO₂NR¹³R¹⁴, at least one of R¹³ and R¹⁴ must be hydrogen;

R³ and R⁴ are independently hydrogen, halogen, alkyl, alkoxy, OH, CF₃, OCF₃, NO₂, C(O)R¹³, C(O)OR¹³, C(O)NR¹³R¹⁴, SO₍ₜ₎NR¹³R¹⁴, SO₍ₜ₎R¹³, C(O)NR¹³OR¹⁴, $$\underset{R^{14}}{\overset{OR^{13}}{\underset{\|}{\text{N}}}}$$

cyano, optionally substituted aryl or optionally substituted heteroaryl, wherein the substituents on the optionally substituted groups may be selected from one or more R⁹ groups.

R⁵ and R⁶ independently represent hydrogen, halogen, alkyl, alkoxy, CF₃, OCF₃, NO₂, C(O)R¹³, C(O)OR¹³, C(O)NR¹³R¹⁴, SO₍ₜ₎NR¹³R¹⁴, C(O)NR¹³OR¹⁴, cyano, or an optionally substituted aryl or optionally substituted heteroaryl group, wherein the substituents on the optionally substituted groups may be selected from one or more R⁹ groups.

R¹⁰, R¹¹ and R¹² independently represent hydrogen, halogen, CF₃, OCF₃, NR¹³R¹⁴, NR¹³C(O)NR¹³R¹⁴, OH, C(O)OR¹³, SH, SO₍ₜ₎NR¹³R¹⁴, SO₂R¹³, NHC(O)R¹³, NHSO₂NR¹³R¹⁴, NHSO₂R¹³, C(O)NR¹³R¹⁴, C(O)NR¹³OR¹⁴, OC(O)R¹³, COR¹³, OR¹³, or cyano; and optionally substituted or unsubstituted: aryl, alkyl, arylalkyl, heteroaryl, aryloxy, heteroarylalkyl, heterocyclocalkyl, cycloalkyl, cycloalkylalkyl, hydroxyalkyl, alkoxy and aminoalkyl;

R¹³ and R¹⁴ are the same or different and are independently selected from the group consisting of H; and optionally substituted or unsubstituted: alkyl, aryl, heteroaryl, arylalkyl, heteroarylalkyl, cycloalkyl, cycloalkylalkyl, and fluoroalkyl; or R¹³ and R¹⁴ when taken together form an optionally substituted 3 to 7 membered heterocyclic ring containing one to two heteroatoms selected from O, S and N, and wherein, the substituents on the optionally substituted groups are selected from the group consisting of H, alkyl, aryl, arylalkyl, fluoroalkyl, cycloalkyl, cycloalkylalkyl, heteroaryl, heteroarylalkyl, amino, carbonyl and halogen.

In another embodiment of this invention:

(1) substituent A in formula I is selected from the group consisting of:

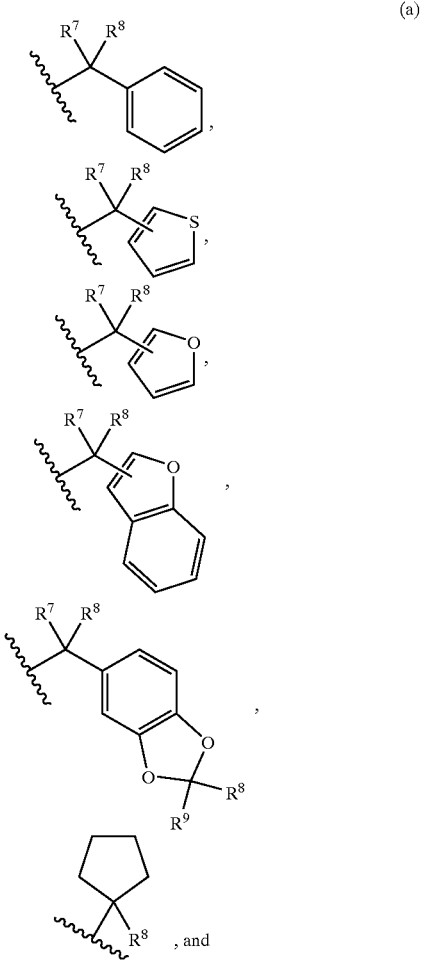

, and

-continued

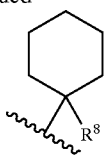

wherein the above rings are unsubstituted, or the above rings are substituted with 1 to 3 substituents independently selected from the group consisting of: H, F, Cl, Br, alkyl, cycloalkyl, and —$CF_3$; $R^7$ is selected from the group consisting of: H, —$CF_3$, —$CF_2CH_3$, methyl, ethyl, isopropyl, cyclopropyl and t-butyl; and $R^8$ is H; and (b)

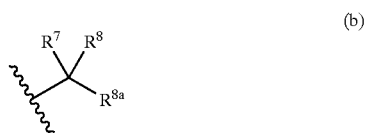

wherein $R^7$ is selected from the group consisting of: H, —$CF_3$, —$CF_2CH_3$, methyl, ethyl, isopropyl, cyclopropyl and t-butyl; and $R^8$ is H; and $R^{8a}$ is as defined for formula I; and (2) substituent B in formula I is selected from the group consisting of:

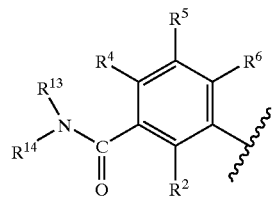 and 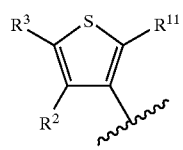

wherein:

$R^2$ is selected from the group consisting of: H, OH, —NHC(O)$R^{13}$ and —NHSO$_2R^{13}$;

$R^3$ is selected from the group consisting of: —C(O)NR$^{13}R^{14}$, —SO$_2$NR$^{13}R^{14}$, —NO$_2$, cyano, —SO$_2R^{13}$; and —C(O)OR$^{13}$;

$R^4$ is selected from the group consisting of: H, —NO$_2$, cyano, —CH$_3$ or —CF$_3$;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H, methyl, ethyl and isopropyl; or $R^{13}$ and $R^{14}$ when taken together with the nitrogen they are attached to in the groups —NR$^{13}R^{14}$, —C(O)NR$^{13}R^{14}$, —SO$_2$NR$^{13}R^{14}$, —OC(O)NR$^{13}R^{14}$, —CONR$^{13}R^{14}$, —NR$^{13}$C(O)NR$^{13}R^{14}$, —SO$_t$NR$^{13}R^{14}$, —NHSO$_2$NR$^{13}R^{14}$ form an unsubstituted or substituted saturated heterocyclic ring (preferably a 3 to 7 membered ring) optionally having one additional heteroatom selected from O, S or NR$^{18}$ wherein $R^{18}$ is selected from H, alkyl, aryl, heteroaryl, —C(O)R$^{19}$, —SO$_2R^{19}$ and —C(O)NR$^{19}R^{20}$, wherein each $R^{19}$ and $R^{20}$ is independently selected from alkyl, aryl and heteroaryl, wherein there are 1 to 3 substituents on the substituted cyclized $R^{13}$ and $R^{14}$ groups and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}R^{16}$, —SO$_t$NR$^{15}R^{16}$, —C(O)R$^{15}$, —SO$_2R^{15}$ provided that $R^{15}$ is not H, —NHC(O)NR$^{15}R^{16}$ and halogen; and wherein each $R^{15}$ and $R^{16}$ is independently selected from the group consisting of: H, alkyl, aryl, arylalkyl, cycloalkyl and heteroaryl.

In another embodiment of this invention:

(1) substituent A in formula I is selected from the group consisting of:

(a)

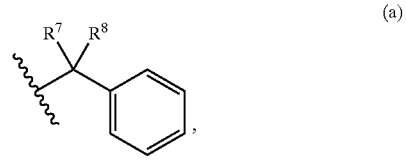

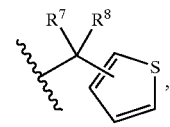

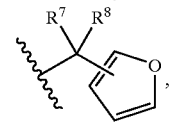

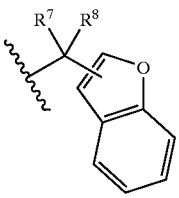

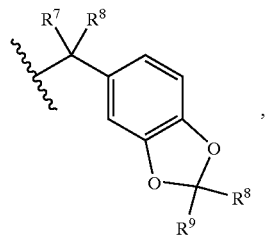

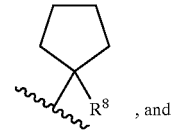, and

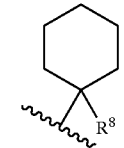

wherein the above rings are unsubstituted, or the above rings are substituted with 1 to 3 substituents independently selected from the group consisting of: F, Cl, Br, alkyl, cycloalkyl, and —$CF_3$; $R^7$ is selected from the group consisting of: H, —$CF_3$, —$CF_2CH_3$, methyl, ethyl, isopropyl, cyclopropyl and t-butyl; and $R^8$ is H; and

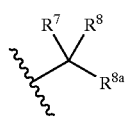
(b)

wherein $R^7$ is selected from the group consisting of: H, —$CF_3$, —$CF_2CH_3$, methyl, ethyl, isopropyl, cyclopropyl and t-butyl; and $R^8$ is H; and $R^{8a}$ is as defined for formula I; and (2) substituent B in formula I is selected from the group consisting of:

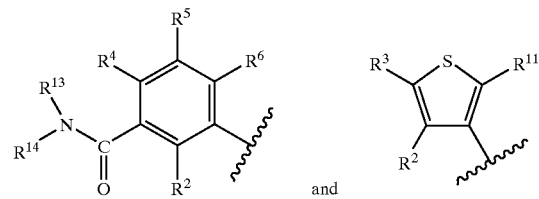

wherein:
$R^2$ is selected from the group consisting of: H, OH, —$NHC(O)R^{13}$ and —$NHSO_2R^{13}$;
$R^3$ is selected from the group consisting of: —$C(O)NR^{13}R^{14}$—$SO_2NR^{13}R^{14}$, —$NO_2$, cyano, and —$SO_2R^{13}$;
$R^4$ is selected from the group consisting of: H, —$NO_2$, cyano, —$CH_3$ or —$CF_3$;
$R^5$ is selected from the group consisting of: H, —$CF_3$, —$NO_2$, halogen and cyano; and
$R^6$ is selected from the group consisting of: H, alkyl and —$CF_3$;
$R^{11}$ is selected from the group consisting of: H, halogen and alkyl; and
each $R^{13}$ and $R^{14}$ is independently selected from the group consisting of: H, methyl and ethyl.

In another embodiment of this invention:
(1) substituent A in formula I is selected from the group consisting of:

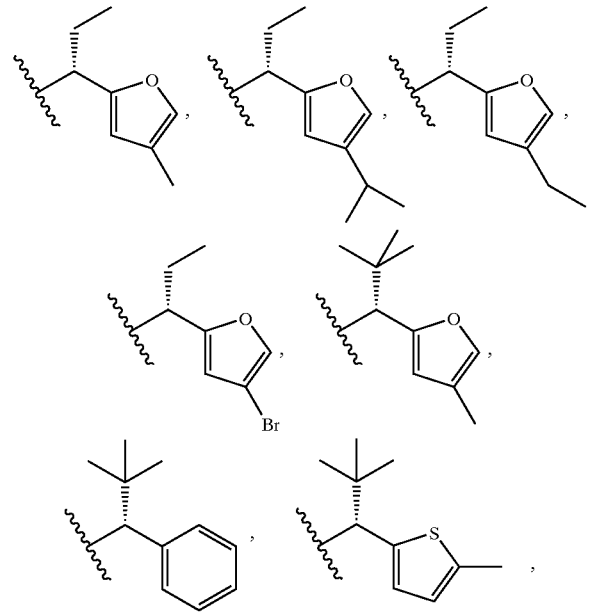

(2) substituent B in formula I is selected from the group consisting of:

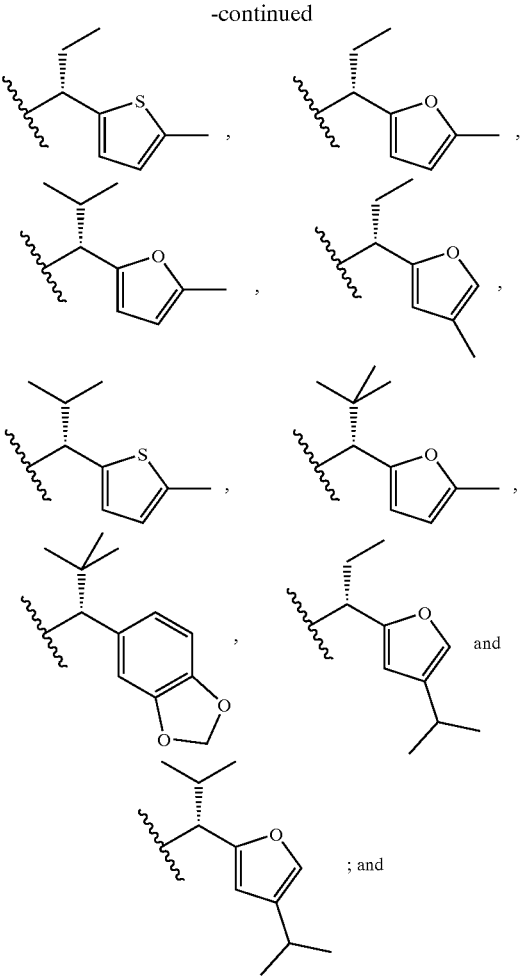

; and (2) substituent B in formula I is selected from the group consisting of:

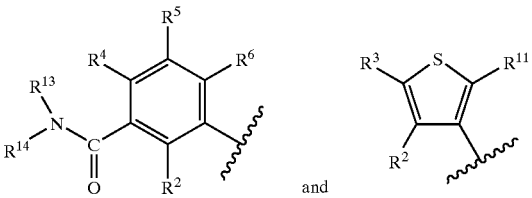

wherein:
$R^2$ is —OH;
$R^3$ is selected from the group consisting of: —$SO_2NR^{13}R^{14}$ and —$CONR^{13}R^{14}$;
$R^4$ is selected form the group consisting of: H, —$CH_3$ and —$CF_3$;
$R^5$ is selected from the group consisting of: H and cyano;
$R^6$ is selected from the group consisting of: H, —$CH_3$ and —$CF_3$;
$R^{11}$ is H; and
$R^{13}$ and $R^{14}$ are independently selected from the group consisting of H and methyl.

In another embodiment of this invention:

(1) substituent A is selected from the group consisting of:

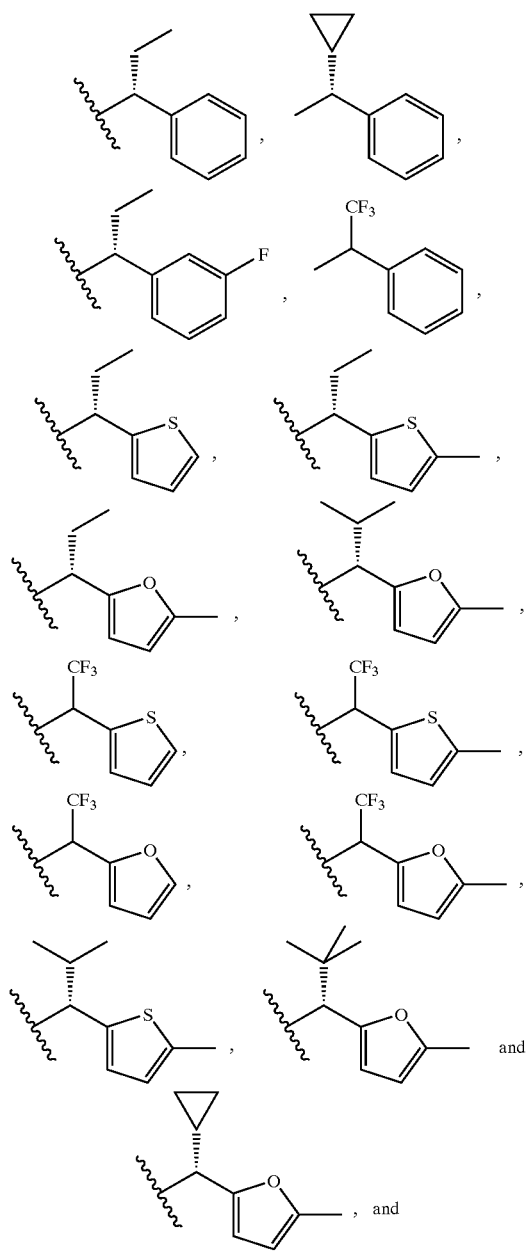

, and

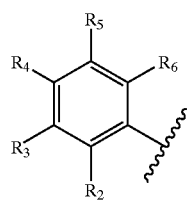

(2) substituent B is:

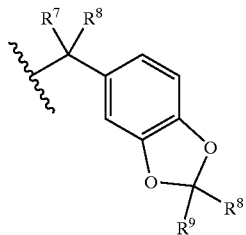

wherein,
R² is —OH;
R³ is CONR¹³R¹⁴;
R⁴ is selected from the group consisting of H, CF₃ and CH₃;
R⁵ is H and cyano;
R⁶ is selected from the group consisting of H, CH₃ and CF₃;
R¹³ and R¹⁴ are methyl.

In another embodiment of this invention, B is as described in any one of the above embodiments, and A is:

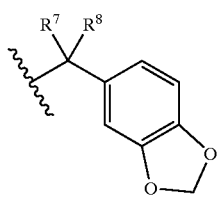

and all other substituents are as defined for formula I.

In another embodiment of this invention, B is as described in any one of the above embodiments, and A is:

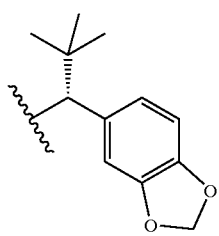

wherein R⁷ is H, and R⁸ is alkyl (e.g., methyl, ethyl, isopropyl, cyclopropyl and t-butyl), and all other substituents are as defined for formula I.

In another embodiment of this invention, B is as described in any one of the above embodiments, and A is:

and all other substituents are as defined for formula I.

In another embodiment of this invention, R¹ in formula I is selected from the group consisting of: H, alkyl, aryl and cycloalkyl.

In another embodiment of this invention, R¹ in formula I is selected from the group consisting of: H, methyl, phenyl and cyclohexyl.

In another embodiment of this invention, R¹ in formula I is selected from the group consisting of: H, methyl, aryl and cyclohexyl.

In another embodiment of this invention, R¹⁵ in formula I is selected from the group consisting of: H, alkyl, aryl and cycloalkyl.

In another embodiment of this invention, R¹⁵ in formula I is selected from the group consisting of: H, methyl, phenyl and cyclohexyl.

In another embodiment of this invention, R¹⁵ in formula I is selected from the group consisting of: H, methyl, aryl and cyclohexyl.

Other embodiments of this invention are directed to the pharmaceutically acceptable salts of the compounds of formula I.

Other embodiments of this invention are directed to the sodium salts of the compounds of formula I.

Other embodiments of this invention are directed to the calcium salts of the compounds of formula I.
Preferred compounds of the invention are listed below:
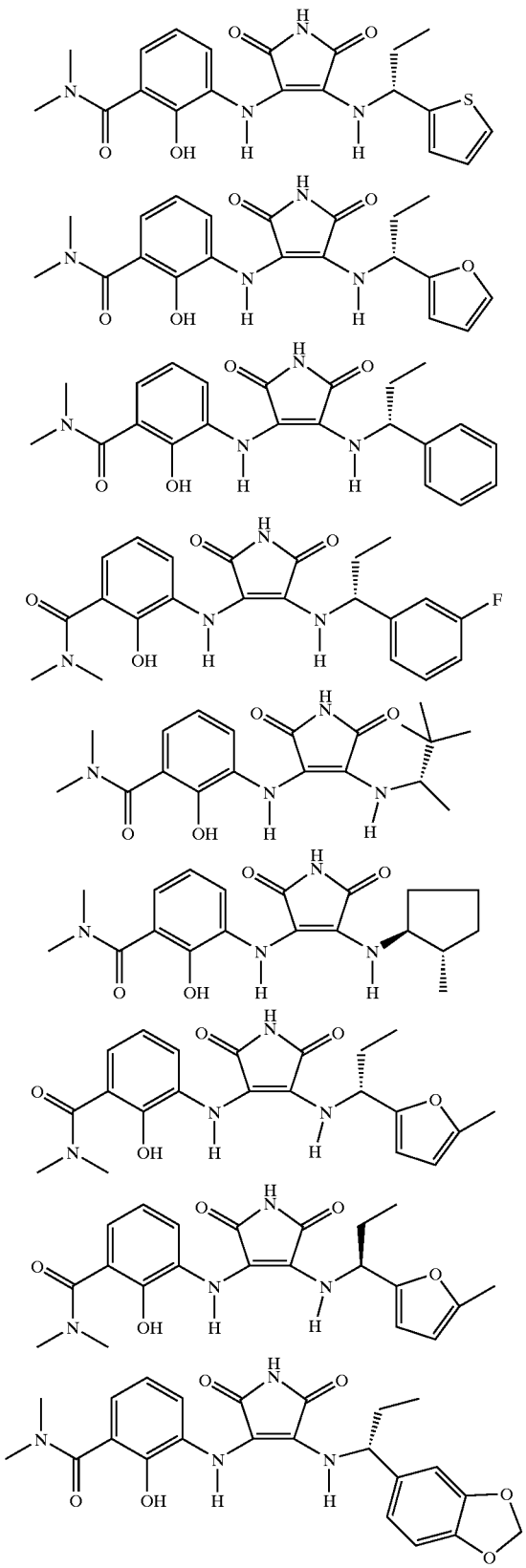
-continued
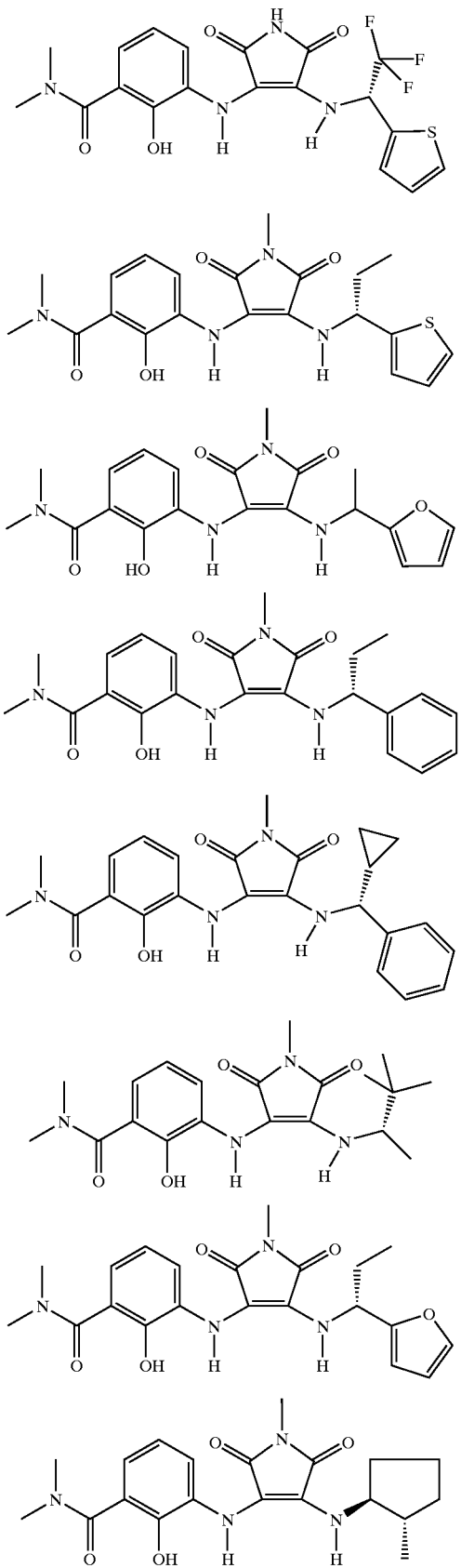

-continued
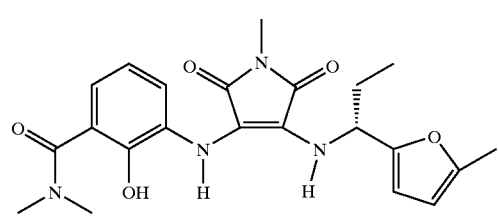
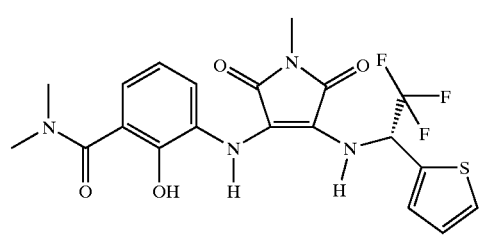
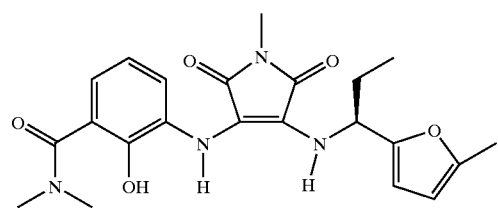
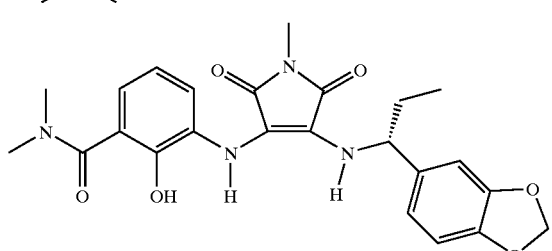
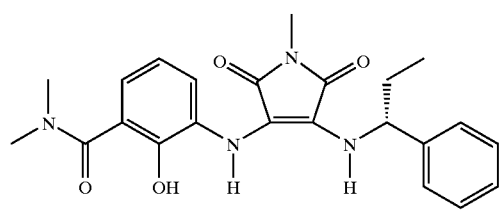
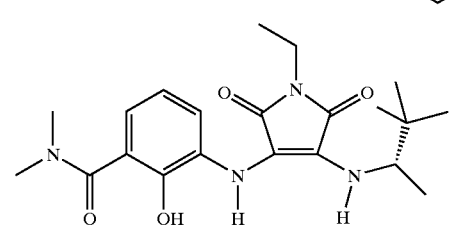
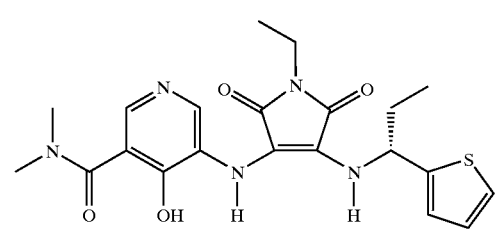
-continued
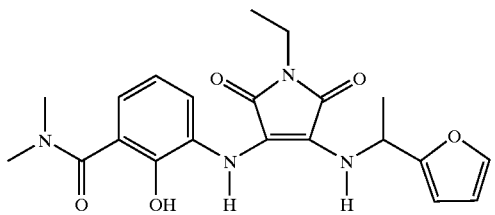
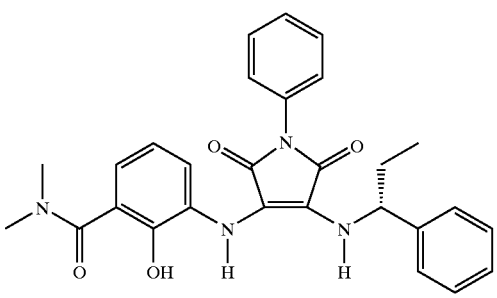
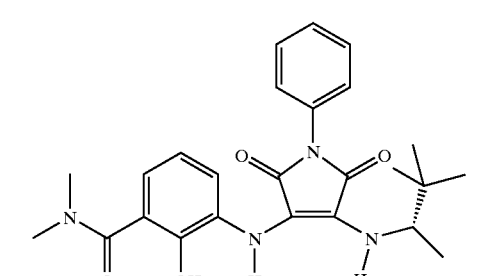
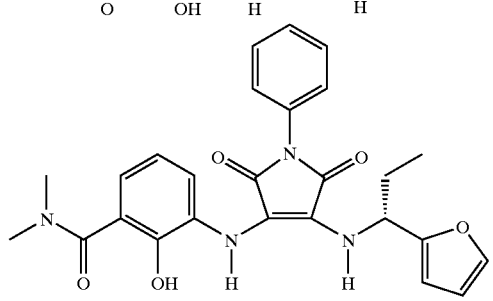
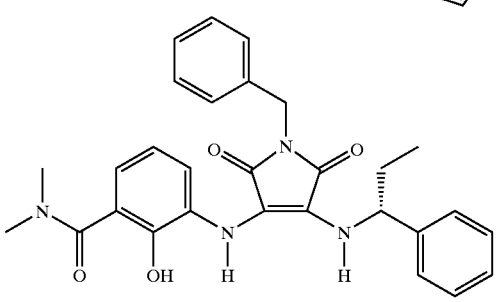
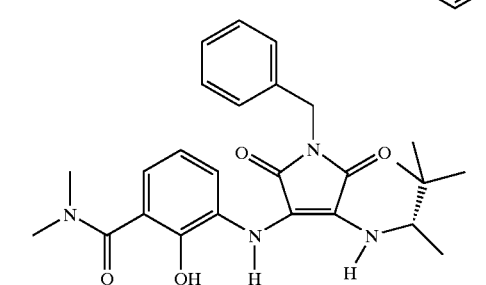

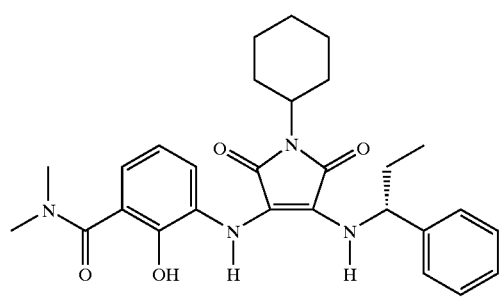
More preferred compounds of the invention are listed below:
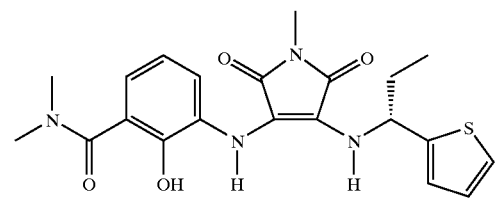
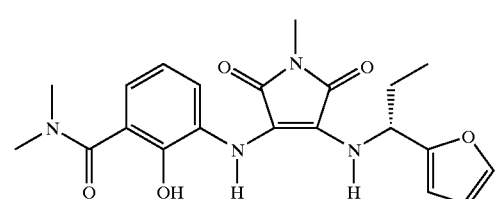
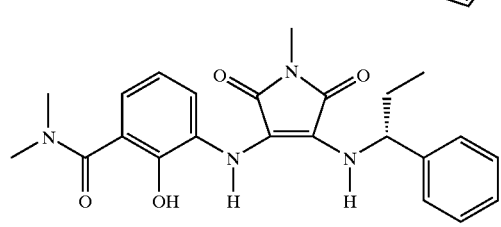
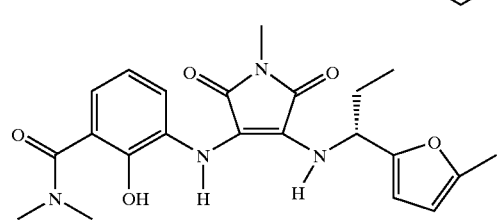
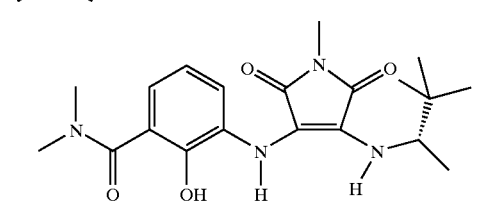
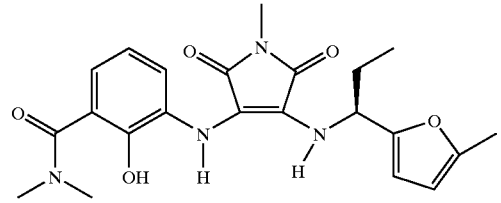
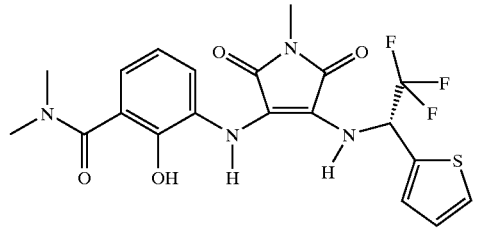
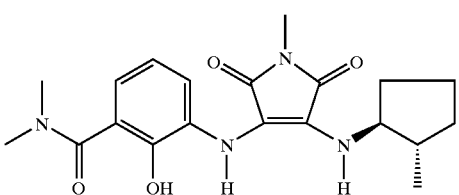
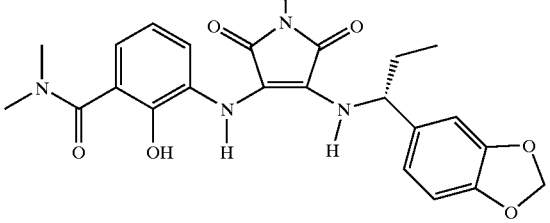
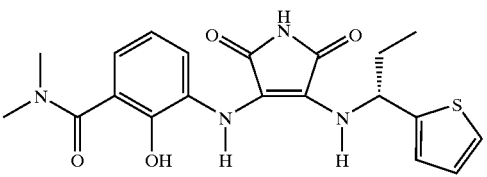
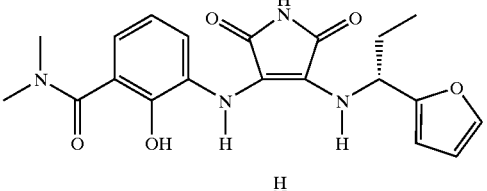
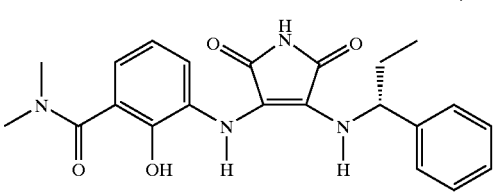
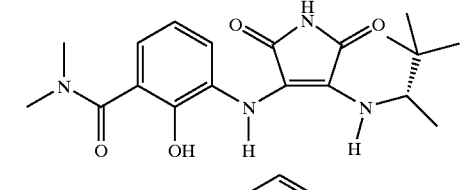
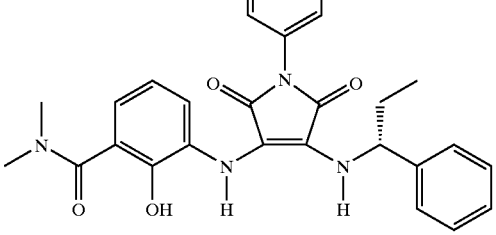

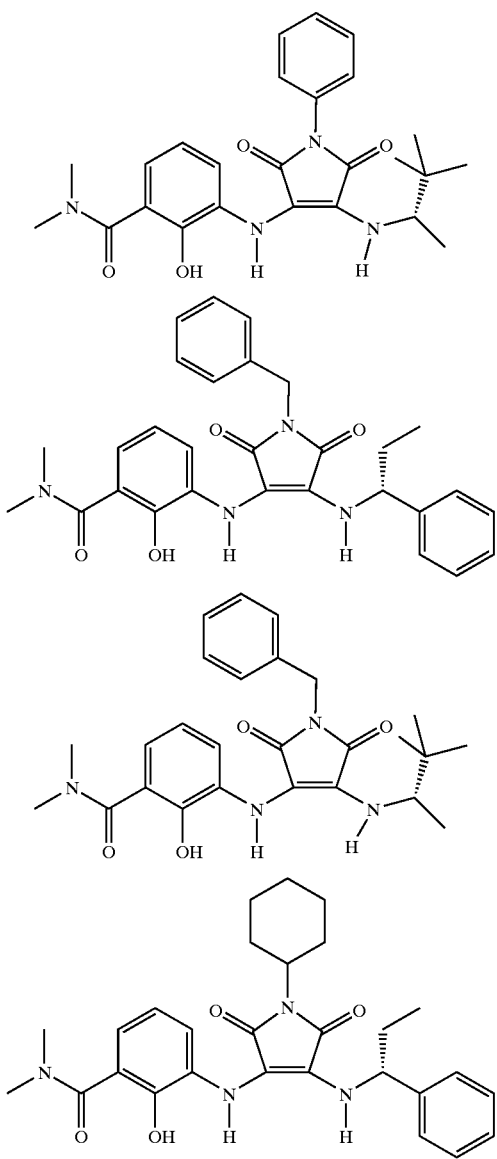

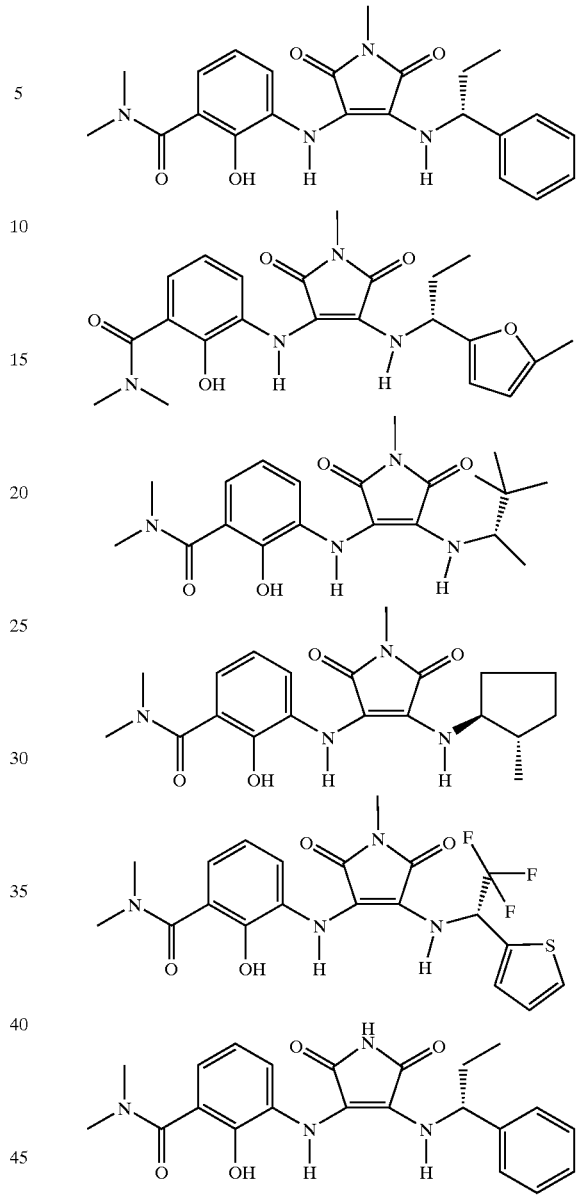

A most preferred group of compounds of the invention is listed below:

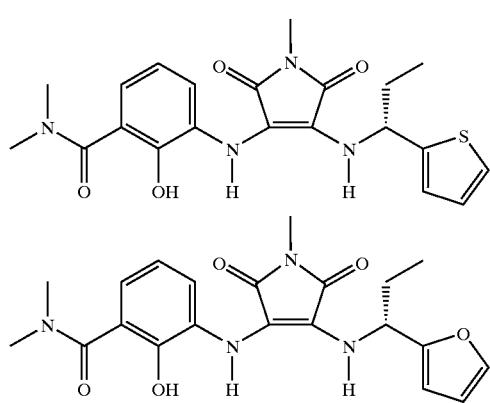

For compounds of the invention having at least one asymmetrical carbon atom, all isomers, including diastereomers, enantiomers and rotational isomers are contemplated as being part of this invention. The invention includes d and l isomers in both pure form and in admixture, including racemic mixtures. Isomers can be prepared using conventional techniques, or by separating isomers of a compound of formula (I).

Compounds of formula (I) can exist in unsolvated and solvated forms, including hydrated forms. In general, the solvated forms, with pharmaceutically acceptable solvents such as water, ethanol and the like, are equivalent to the unsolvated forms for purposes of this invention.

A compound of formula (I) may form pharmaceutically acceptable salts with organic and inorganic acids or bases. Examples of suitable bases for salt formation include but are not limited to sodium hydroxide, lithium hydroxide, potassium hydroxide, and calcium hydroxide. Salts of phenols can be made by heating acidic compounds with any of the above mentioned bases according to procedures well known to those skilled in the art. Examples of suitable acids for salt formation are hydrochloric, sulfuric, phosphoric, acetic, citric, malonic, salicylic, malic, fumaric, succinic, ascorbic, maleic, methanesulfonic and other mineral and carboxylic acids well known to those skilled in the art. The salts are prepared by contacting the free base forms with a sufficient amount of the desired acid to produce a salt in the conventional manner. The free base forms may be regenerated by treating the salt with a suitable dilute aqueous base solution, such as dilute aqueous sodium hydroxide, lithium hydroxide, potassium hydroxide, calcium hydroxide, potassium carbonate, ammonia or sodium bicarbonate. The neutral forms differ from their respective salt forms somewhat in certain physical properties, such as solubility in polar solvents, but the salts are otherwise equivalent to their respective neutral forms for purposes of the invention.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal composition can take the form of creams, lotions, aerosols and/or emulsions and can be included in a transdermal patch of the matrix or reservoir type as are conventional in the art for this purpose.

The compounds of the invention may also be delivered by direct application to the tumor site following surgery, e.g., in a sponge preparation.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

Examples of chemokine mediated disease include: psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral and cardiac ischemia, osteoarthritis, multiple sclerosis, restinosis, angiogenesis, osteoporosis, gingivitis, respiratory viruses, herpes viruses, hepatitis viruses, HIV, Kaposi's sarcoma associated virus, meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred and corneal neovascularization, polymyositis, vasculitis, acne, gastric and duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, cough, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy, periodontitis, transplant reperfusion injury and early transplantation.

Another aspect of the invention is a method treating cancer, comprising administering to a patient in need thereof, concurrently or sequentially, a therapeutically effective amount of (a) a compound of formula (I) and (b) a chemotherapeutic agent (i.e. an antineoplastic agent, microtubule affecting agent or anti-angiogenesis agent).

In an embodiment of the invention, a compound of formula (I) is combined with one of the following antineoplastic agents: gemcitabine, paclitaxel (Taxol®), 5-Fluorouracil (5-FU), cyclophosphamide (Cytoxan®), temozolomide, taxotere or Vincristine.

Classes of compounds that can be used as the chemotherapeutic agent (antineoplastic agent) include: alkylating agents, antimetabolites, natural products and their derivatives, hormones, anti-hormones, anti-angiogenic agents and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxyco-formycin, Mitomycin-C, L-Asparaginase, Interferons (especially IFN-α), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Anti-angiogenic agents include Marimastat, AG3340, Col-3, Neovastat, BMS-275291, Thalidomide, Squalamine, Endostatin, SU-5416, SU-6668, Interferon-alpha, Anti-VEGF antibody, EMD121974, CAI, Interleukin-12, IM862, Platelet Factor-4, Vitaxin, Angiostatin, Suramin, TNP-470, PTK-787, ZD-6474, ZD-101, Bay 129566, CGS27023A, taxotere and Taxol.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) *Science*, 274:2009) estramustine, nocodazole, MAP4, and the like. Examples of such agents are also described in the scientific and patent literature, see, e.g., Bulinski (1997) *J. Cell Sci.* 110:3055–3064; Panda (1997) *Proc. Natl. Acad. Sci. USA* 94:10560–10564; Muhlradt (1997) *Cancer Res.* 57:3344–3346; Nicolaou (1997) *Nature* 387:268–272; Vasquez (1997) *Mol. Biol. Cell.* 8:973–985; Panda (1996) *J. Biol. Chem.* 271:29807–29812.

Particularly preferred agents are compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos: 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) *Oncology*, 6:17–23, Horwitz (1992) *Trends Pharmacol. Sci.* 13: 134–146, Rowinsky (1990) *J. Natl. Canc. Inst.* 82: 1247–1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) *Cancer Chemother. Pharmacol.* 41 :37–47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

In a preferred embodiment, compounds with possible tubulin polymerization activity are screened in vitro. In a preferred embodiment, the compounds are screened against cultured WR21 cells (derived from line 69–2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) *Lab. Anim. Sci.*, 45(2):145–150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) *J. Molec. Biol.*, 89: 737–758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA); the disclosure of which is incorporated herein by reference thereto.

The amount and frequency of administration of the compounds of formula (I) and the chemotherapeutic agents and/or radiation therapy will be regulated according to the judgment of the attending clinician (physician) considering such factors as age, condition and size of the patient as well as severity of the disease being treated. A dosage regimen of the compound of formula (I) can be oral administration of from 10 mg to 2000 mg/day, preferably 10 to 1000 mg/day, more preferably 50 to 600 mg/day, in two to four (preferably two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

In the methods of this invention, a compound of formula (I) is administered concurrently or sequentially with a chemotherapeutic agent and/or radiation. Thus, it is not necessary that, for example, the chemotherapeutic agent and the compound of formula (I), or the radiation and the compound of formula (I), should be administered simultaneously or essentially simultaneously. The advantage of a simultaneous or essentially simultaneous administration is well within the determination of the skilled clinician.

Also, in general, the compound of formula (I) and the chemotherapeutic agent do not have to be administered in the same pharmaceutical composition, and may, because of different physical and chemical characteristics, have to be administered by different routes. For example, the compound of formula (I) may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of a compound of formula (I), and chemotherapeutic agent and/or radiation will depend upon the diagnosis of the attending physicians and their judgement of the condition of the patient and the appropriate treatment protocol.

The compound of formula (I), and chemotherapeutic agent and/or radiation may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound of formula (I).

If the compound of formula (I) and the chemotherapeutic agent and/or radiation are not administered simultaneously or essentially simultaneously, then the initial order of administration of the compound of formula (I) and the chemotherapeutic agent and/or radiation, may not be important. Thus, the compound of formula (I) may be administered first followed by the administration of the chemotherapeutic agent and/or radiation; or the chemotherapeutic agent and/or radiation may be administered first followed by the administration of the compound of formula (I). This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of a compound of formula (I) followed, where determined advantageous, by the administration of the chemotherapeutic agent and/or radiation, and so on until the treatment protocol is complete.

Thus, in accordance with experience and knowledge, the practicing physician can modify each protocol for the administration of a component (therapeutic agent—ie., the compound of formula (I), chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Biological Examples

The compounds of the present invention are useful in the treatment of CXC-chemokine mediated conditions and diseases. This utility is manifested in their ability to inhibit IL-8 and GRO-α chemokine which may be demonstrated by the following in vitro assays.

Receptor Binding Assays:

CXCR1 SPA Assay

For each well of a 96 well plate, a reaction mixture of 10 μg hCXCR1-CHO overexpressing membranes (Biosignal) and 200 μg/well WGA-SPA beads (Amersham) in 100 μl is prepared in CXCR1 assay buffer (25 mM HEPES, pH 7.8, 2 mM $CaCl_2$, 1 mM $MgCl_2$, 125 mM NaCl, 0.1% BSA) (Sigma). A 0.4 nM stock of ligand, [125I]-IL-8 (NEN) is prepared in the CXCR1 assay buffer. 20× stock solutions of test compounds are prepared in DMSO (Sigma). A 6×-stock solution of IL-8 (R&D) is prepared in CXCR2 assay buffer. The above solutions are added to a 96-well assay plate (Perkin Elmer) as follows: 10 μl test compound or DMSO, 40 μl CXCR1 assay buffer or IL-8 stock, 100 μl of reaction mixture, 50 µl of ligand stock (Final [Ligand]=0.1 nM). The assay plates are shaken for 5 minutes on plate shaker, then incubated for 8 hours before cpm/well are determined in Microbeta Trilux counter (Perkin Elmer). % Inhibition of Total binding-NSB (250 nM IL-8) is determined for IC50 values.

Alternative CXCR1 SPA Assay

Protocol Using CXCR1-Expressing Membranes From Biosignal Packard

For each 50 µl reaction, a working stock of 0.25 µg/µl hCXCR1-CHO over-expressing membranes with a specific activity of 0.05 pmol/mg (Biosignal Packard) and 25 µg/µl WGA-SPA beads (Perkin Elmer Life Sciences) is prepared in CXCR1 assay buffer (25 mM HEPES, pH 7.8, 0.1 mM $CaCl_2$, 1 mM $MgCl_2$, 100 mM NaCl) (Sigma). This mixture is incubated on ice for 30 minutes and then centrifuged at 2500 rpm for 5 minutes. The beads and membranes are resuspended in CXCR1 assay buffer to the same concentrations as in the original mixture. A 0.125 nM stock of ligand, [$^{125}$I]-IL-8 (Perkin Elmer Life Sciences), is prepared in the CXCR1 assay buffer. Test compounds are first serially diluted by half-logs in DMSO (Sigma) and then diluted 20-fold in CXCR1 assay buffer. The above solutions are added to a Corning NBS (non-binding surface) 96-well assay plate as follows: 20 µl test compound or 5% DMSO (final [DMSO]=2%), 20 µl of membranes and SPA bead mixture (Final [membrane]=5 µg/reaction; Final [SPA bead]=500 µg/reaction), 10 µl of ligand stock (Final [$^{125}$I-IL-8]=0.025 nM). The assay plates are incubated for 4 hours before cpm/well are determined in a Microbeta Trilux counter (Perkin Elmer Life Sciences). $IC_{50}$ values are quantified using nonlinear regression analysis in GraphPad Prism.

Alternative CXCR1 SPA Assay

Protocol Using CXCR1-Expressing Membranes From Euroscreen

For each 50 µl reaction, a working stock of 0.025 µg/µl hCXCR1-CHO over-expressing membranes with a specific activity of 3.47 pmol/mg (Euroscreen) and 5 µg/µl WGA-SPA beads (Perkin Elmer Life Sciences) is prepared in CXCR1 assay buffer (25 mM HEPES, pH 7.8, 2.0 mM $CaCl_2$, 1 mM $MgCl_2$, 125 mM NaCl) (Sigma). This mixture is incubated on ice for 5 minutes. A 0.125 nM stock of ligand, [$^{125}$I]-IL-8 (Perkin Elmer Life Sciences), is prepared in the CXCR1 assay buffer. Test compounds are first serially diluted by half-logs in DMSO (Sigma) and then diluted 13.3-fold in CXCR1 assay buffer. The above solutions is added to a Corning NBS (non-binding surface) 96-well assay plate as follows: 20 µl test compound or 7.5% DMSO (final [DMSO]=3%), 20 µl of membranes and SPA bead mixture (Final [membrane]=0.5 µg/reaction; Final [SPA bead]=100 µg/reaction), 10 µl of ligand stock (Final [$^{125}$I-IL-8]=0.025 nM). The assay plates are incubated for 4 hours before cpm/well are determined in a Microbeta Trilux counter (Perkin Elmer Life Sciences). $IC_{50}$ values are quantified using nonlinear regression analysis in GraphPad Prism.

CXCR2 SPA Assay

For each well of a 96 well plate, a reaction mixture of 4 µg hCXCR2-CHO overexpressing membranes (Biosignal) and 200 µg/well WGA-SPA beads (Amersham) in 100 µl is prepared in CXCR2 assay buffer (25 mM HEPES, pH 7.4, 2 mM $CaCl_2$, 1 mM $MgCl_2$). A 0.4 nM stock of ligand, [125I]-IL-8 (NEN), is prepared in the CXCR2 assay buffer. 20× stock solutions of test compounds are prepared in DMSO (Sigma). A 6× stock solution of GRO-α (R&D) is prepared in CXCR2 assay buffer. The above solutions are added to a 96-well assay plate (Perkin Elmer or Corning) as follows: 10 µl test compound or DMSO, 40 ul CXCR2 assay buffer or GRO-α stock, 100 µl of reaction mixture, 50 µl of ligand stock (Final [Ligand]=0.1 nM). When 40× stock solutions of test compounds in DMSO are prepared, then the above protocol is used except instead 5 µl test compound or DMSO and 45 µl CXCR2 assay buffer are used. The assay plates are shaken for 5 minutes on a plate shaker, then incubated for 2–8 hours before cpm/well are determined in Microbeta Trilux counter (Perkin Elmer). % Inhibition of total binding minus non-specific binding (250 nM Gro-α or 50 µM antagonist) is determined and IC50 values calculated.

Alternative CXCR2 SPA Assay

Protocol Using the CXCR2 50 µl Assay

For each 50 µl reaction, a working stock of 0.031 µg/µl hCXCR2-CHO over-expressing membranes with a specific activity of 0.4 pmol/mg (Biosignal Packard) and 2.5 µg/µl WGA-SPA beads (Perkin Elmer Life Sciences) is prepared in CXCR2 assay buffer (25 mM HEPES, pH 7.4, 2.0 mM $CaCl_2$, 1 mM $MgCl_2$) (Sigma). This mixture is incubated on ice for 5 minutes. A 0.50 nM stock of ligand, [$^{125}$I]-IL-8 (Perkin Elmer Life Sciences), is prepared in the CXCR2 assay buffer. Test compounds are first serially diluted by half-logs in DMSO (Sigma) and then diluted 13.3-fold in CXCR2 assay buffer. The above solutions are added to a Corning NBS (non-binding surface) 96-well assay plate as follows: 20 µl test compound or 7.5% DMSO (final [DMSO]=3%), 20 µl of membranes and SPA bead mixture (final [membrane]=0.625 µg/reaction; final [SPA bead]=50 µg/reaction), 10 µl of ligand stock (final [$^{125}$I-IL-8]=0.10 nM). The assay plates are incubated for 2 hours before cpm/well are determined in a Microbeta Trilux counter (Perkin Elmer Life Sciences). $IC_{50}$ values are quantified using nonlinear regression analysis in GraphPad Prism.

Alternative CXCR2 SPA Assay

Protocol Using the CXCR2 200 µl Assay

For each 200 µl reaction, a working stock of 0.02 µg/µl hCXCR2—CHO over-expressing membranes with a specific activity of 0.6 pmol/mg (Biosignal Packard) and 2 µg/µl WGA-SPA beads (Perkin Elmer Life Sciences) is prepared in CXCR2 assay buffer (25 mM HEPES, pH 7.4, 2.0 mM $CaCl_2$, 1 mM $MgCl_2$) (Sigma). This mixture is incubated on ice for 5 minutes. A 0.40 nM stock of ligand, [$^{125}$I]-IL-8 (Perkin Elmer Life Sciences), is prepared in the CXCR2 assay buffer. Test compounds are first serially diluted by half-logs in DMSO (Sigma) and then diluted 20-fold in CXCR2 assay buffer. The above solutions are added to a Corning NBS (non-binding surface) 96-well assay plate as follows: 50 µl test compound or 10% DMSO (final [DMSO]=2.5%), 100 µl of membranes and SPA bead mixture (final [membrane]=2 µg/reaction; final [SPA bead]=200 µg/reaction), 50 µl of ligand stock (final [$^{125}$I-IL-8]=0.10 nM). The assay plates are incubated for 2 hours before cpm/well were determined in a Microbeta Trilux counter (Perkin Elmer Life Sciences). $IC_{50}$ values are quantified using nonlinear regression analysis in GraphPad Prism.

Calcium Fluorescence Assay (FLIPR)

HEK 293 cells stably transfected with hCXCR2 and Gα1/q are plated at 10,000 cells per well in a Poly-D-Lysine Black/Clear plate (Becton Dickinson) and incubated 48 hours at 5% $CO_2$, 37° C. The cultures are then incubated with 4 mM fluo-4, AM (Molecular Probes) in Dye Loading Buffer (1% FBS, HBSS w. Ca & Mg, 20 mM HEPES (Cellgro), Probenicid (Sigma)) for 1 hour. The cultures are washed with wash buffer (HBSS w Ca, & Mg, 20 mM HEPES, Probenicid (2.5 mM)) three times, then 100 µl/well wash buffer is added.

During incubation, compounds are prepared as 4× stocks in 0.4% DMSO (Sigma) and wash buffer and added to their respective wells in the first addition plate. IL-8 or GRO-α (R&D Systems) concentrations are prepared 4× in wash buffer +0.1% BSA and added to their respective wells in second addition plate.

Culture plate and both addition plates are then placed in the FLIPR imaging system to determine change in calcium fluorescence upon addition of compound and then ligand. Briefly, 50 μl of compound solutions or DMSO solution is added to respective wells and change in calcium fluorescence measured by the FLIPR for 1 minute. After a 3 minute incubation within the instrument, 50 μl of ligand is then added and the change in calcium fluorescence measured by the FLIPR instrument for I minute. The area under each stimulation curve is determined and values used to determine % Stimulation by compound (agonist) and % Inhibition of Total Calcium response to ligand (0.3 nM IL-8 or GRO-α) for IC50 values of the test compounds.

Chemotaxis Assays for 293-CXCR2

A chemotaxis assay is setup using Fluorblok inserts (Falcon) for 293-CXCR2 cells (HEK-293 cells overexpressing human CXCR2). The standard protocol used at present is as follows:

1. Inserts are coated with collagenIV (2 ug/ml) for 2 hrs at 37° C.
2. The collagen is removed and inserts are allowed to air dry overnight.
3. Cells are labeled with 10 uM calcein AM (Molecular Probes) for 2 hrs. Labeling is done in complete media with 2% FBS.
4. Dilutions of compound are made in minimal media (0.1% BSA) and placed inside the insert which is positioned inside the well of a 24 well plate. Within the well is IL-8 at a concentration of 0.25 nM in minimal media. Cells are washed and resuspended in minimal media and placed inside the insert at a concentration of 50,000 cells per insert.
5. Plate is incubated for 2 hrs and inserts are removed and placed in a new 24 well. Fluorescence is detected at excitation=485 nM and emission=530 nM.

Cytotoxicity Assays

A cytotoxicity assay for CXCR2 compounds is conducted on 293-CXCR2 cells. Concentrations of compounds are tested for toxicity at high concentrations to determine if they may be used for further evaluation in binding and cell based assays. The protocol is as follows:

1. 293-CXCR2 cells are plated overnight at a concentration of 5000 cells per well in complete media.
2. Dilutions of compound are made in minimal media w/0.1% BSA. Complete media is poured off and the dilutions of compound are added. Plates are incubated for 4, 24 and 48 hrs. Cells are labeled with 10 uM calcein AM for 15 minutes to determine cell viability. Detection method is the same as above.

Soft Agar Assay 10,000 SKMEL-5 cells/well are placed in a mixture of 1.2% agar and complete media with various dilutions of compound. Final concentration of agar is 0.6%. After 21 days viable cell colonies are stained with a solution of MTT (1 mg/ml in PBS). Plates are then scanned to determine colony number and size. $IC_{50}$ is determined by comparing total area vs. compound concentration.

Compounds of this invention may exhibit a range of CXCR2 receptor binding activities from about 1 nM to about 10,000 nM.

Compounds of formula (I) may be produced by processes known to those skilled in the art in the following reaction schemes and in the preparations and examples below.

Scheme 1

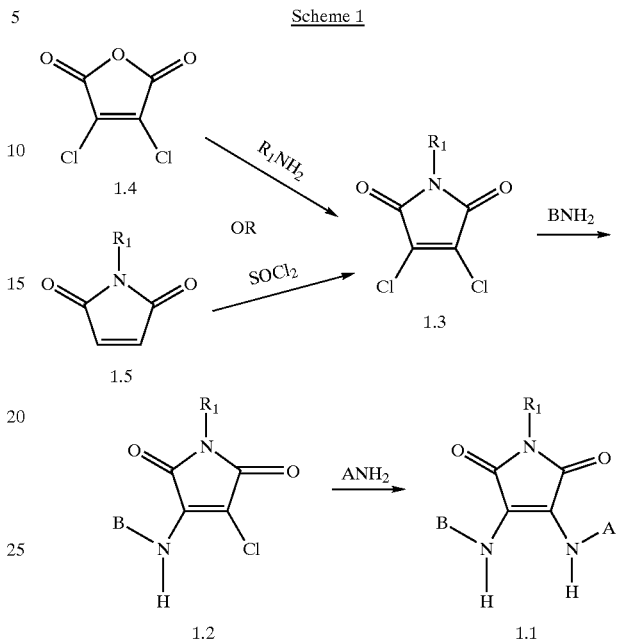

If one were to follow the procedure set forth in Bioorg. Med. Chem. 1999, 7, 1067–1074 starting with compound 1.4 or the procedure set forth in Acta Crystallogr. Sect. C: Cryst. Struct. Commun. 2000, 56,190–192 starting with compound 1.5, one would obtain the compound 1.3; compound 1.3 could react with an amine $BNH_2$ to afford compound 1.2 and then compound 1.2 could react with another amine $ANH_2$ to afford the compound 1.1.

The following examples illustrate the preparation of some of the compounds of the invention and are not to be construed as limiting the invention disclosed herein. Alternate mechanistic pathways and analogous structures will be apparent to those skilled in the art.

Preparative Example 1

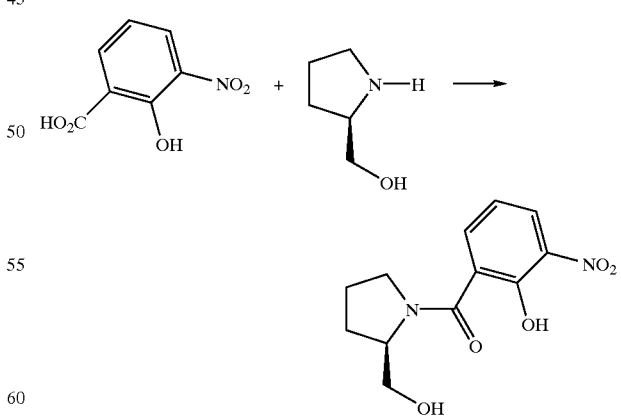

3-Nitrosalicylic acid (500 mg, 2.7 mmol), DCC (563 mg) and ethyl acetate (10 mL) were combined and stirred for 10 min. (R)-(−)-2-pyrrolidinemethanol (0.27 mL) was added and the resulting suspension was stirred at room temperature overnight. The solid was filtered and the filtrate washed with 1N NaOH. The aqueous phase was acidified and extracted with EtOAc. The resulting organic phase was dried over anhydrous MgSO$_4$, filtered and concentrated in vacuo. Purification of the residue by preparative plate chromatography (silica gel, 5% MeOH/CH$_2$Cl$_2$ saturated with AcOH) gave the above compound (338 mg, 46%, MH$^+$=267).

Preparative Example 2

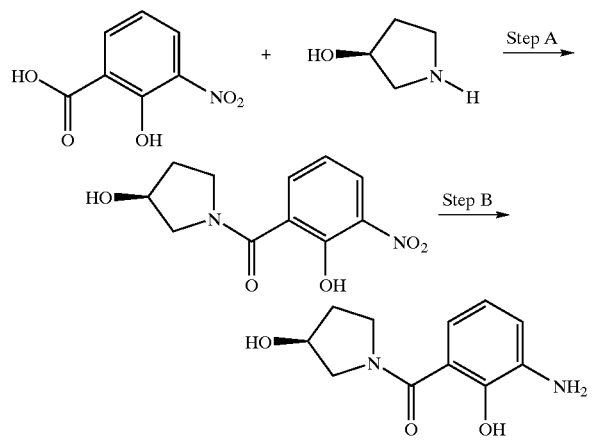

Step A

3-Nitrosalicylic acid (9.2 g), bromotripyrrolidinophosphonium hexafluorophosphate (PyBroP, 23 g) and N,N-diisopropylethylamine (DIEA, 26 mL) in anhydrous CH$_2$Cl$_2$ (125 mL) were combined and stirred at 25° C. for 30 min. (R)-(+)-3-pyrrolidinol (8.7 g) in CH$_2$Cl$_2$ (25 mL) was added over 25 min and the resulting suspension was stirred at room temperature overnight. The mixture was extracted with 1M NaOH (aq) and the organic phase was discarded. The aqueous phase was acidified with 1M HCl (aq), extracted with EtOAc, dried over anhydrous Na$_2$SO$_4$, filtered and concentrated in vacuo to afford the crude product (7 g) which was used without further purification.

Step B

The crude product from Step A above was stirred with 10% Pd/C (0.7 g) in MeOH (100 mL) under a hydrogen gas atmosphere overnight. The reaction mixture was filtered through celite, the filtrate concentrated in vacuo, and the resulting residue purified by column chromatography (silica gel, 10% MeOH/CH$_2$Cl$_2$ saturated with NH$_4$OH) to give the product (2.5 g, 41%, MH$^+$=223).

Preparative Example 3–12

Following the procedures set forth in Preparative Examples 1–2 but using the carboxylic acid, amine, and appropriate coupling agent [DCC (Prep. Ex. 1) or PyBrop (Prep. Ex. 2)] listed in the Table below, the amide product was obtained and used without further purification.

| Prep Ex. | Carboxylic acid | Amine | Amide Product | 1. Coupling Agent  2. Yield  3. MH$^+$ |
|---|---|---|---|---|
| 3 | | | | 1. PyBrop  2. 87%, 86%  3. 181 |
| 4 | | | | 1. PyBroP  2. 49%  3. 209 |
| 6 | | NH$_3$ | | 1. PyBroP  2. 95%  3. 153 |
| 7 | | —NH$_2$ | | 1. PyBroP  2. 83%  3. 167 |
| 8 | | | | 1. PyBroP  2. 76%  3. 223 |

-continued

| Prep Ex. | Carboxylic acid | Amine | Amide Product | 1. Coupling Agent 2. Yield 3. MH+ |
|---|---|---|---|---|
| 11 | HO2C-C6H3(OH)(NO2) | pyrrolidine | pyrrolidine amide with OH, NH2 | 1. PyBroP 2. 59%, 69% 3. 207 |
| 12 | HO2C-C6H3(OH)(NO2) | (R)-3-hydroxymethylpyrrolidine | corresponding amide | 1. PyBroP 2. 49%, 86% 3. 237 |

Preparative Example 15

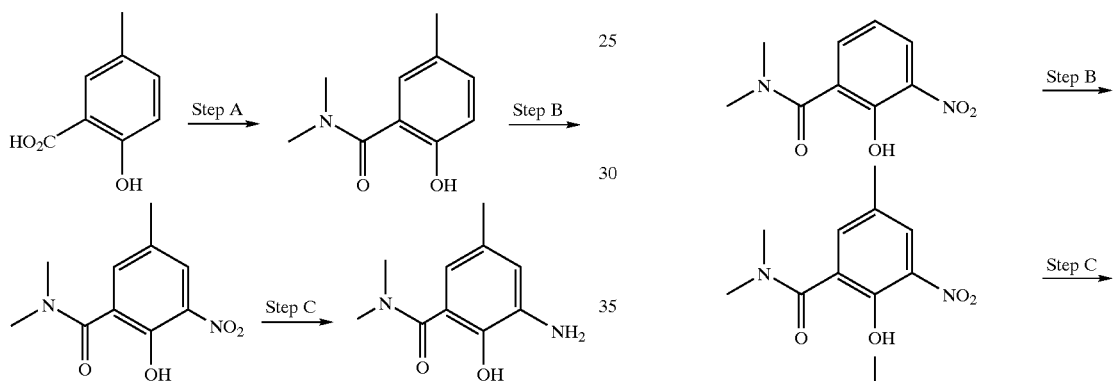

Step A

Following a similar procedure as in Preparative Example 1 except substituting dimethylamine (2M in THF, 33 mL) for (R)-(−)-2-pyrrolidinemethanol and 5-methylsalicylic acid (5 g) for 3-nitrosalicylic acid, the above compound was prepared (6.5 g).

Step B

Nitric acid (0.8 mL) in H$_2$SO$_4$ was added to a cooled (−20° C.) suspension of the title compound from Step A above (3 g) in H$_2$SO$_4$ (25 mL). The mixture was treated with 50% NaOH (aq) dropwise, extracted with CH$_2$Cl$_2$, dried over anhydrous MgSO$_4$, filtered and concentrated in vacuo to give the above compound as a crude solid (2.1 g, 44%, MH$^+$=225).

Step C

The product was prepared following a similar procedure as described in Preparative Example 2, Step B (0.7 g, 99%, MH$^+$=195).

Preparative Example 25

Step A

Following a similar procedure as in Preparative Example 2 Step A, except substituting dimethylamine for (R)-(−)-2-pyrrolidinemethanol, the product of step A was prepared.

Step B

The product from step A above (8 g) was combined with iodine (9.7 g), silver sulfate (11.9 g), EtOH (200 mL) and water (20 mL) and stirred overnight. Filtration, concentration of the filtrate, re-dissolution in $CH_2Cl_2$ and washing with 1M HCl (aq) gave an organic solution which was dried over anhydrous $MgSO_4$, filtered and concentrated in vacuo to afford the product of step B (7.3 g, 57%, $MH^+$=337).

Step C

The product from Step B above (3.1 g) was combined with DMF (50 mL) and MeI (0.6 mL). NaH (60% in mineral oil, 0.4 g) was added portionwise and the mixture was stirred overnight. Concentration in vacuo afforded a residue which was diluted with $CH_2Cl_2$, washed with 1M NaOH (aq), dried over anhydrous $MgSO_4$, filtered and concentrated in vacuo. Purification through a silica gel column (EtOAc/Hex, 1:1) gave the product of step C (1.3 g, 41%, $MH^+$=351).

Step D

The product from Step C above (200 mg), $Zn(CN)_2$ (132 mg), $Pd(PPh_3)_4$ (130 mg) and DMF (5 mL) were heated at 80° C. for 48 hrs, then cooled to room temperature and diluted with EtOAc and 2M $NH_4OH$. After shaking well, the organic extract was dried over anhydrous $MgSO_4$, filtered, concentrated in vacuo and purified by preparative plate chromatography (Silica, EtOAc/Hex, 1:1) to give the product of step D (62 mg, 44%, $MH^+$=250).

Step E $BBr_3$ (1.3 mL, 1M in $CH_2Cl_2$) was added to a $CH_2Cl_2$ solution (5 mL) of the product from Step D above (160 mg) and stirred for 30 min. The mixture was diluted with water, extracted with $CH_2Cl_2$, dried over anhydrous $MgSO_4$, filtered, and concentrated in vacuo to give the product of step E (158 mg, $MH^+$=236).

Step F

A mixture of the product from step E above (160 mg), platinum oxide (83%, 19 mg), and EtOH (20 mL) was stirred under hydrogen (25–40 psi) for 1.5 hr. Filtration through celite and concentration in vacuo afforded the product of step F (165 mg, $MH^+$=206).

Preparative Example 26

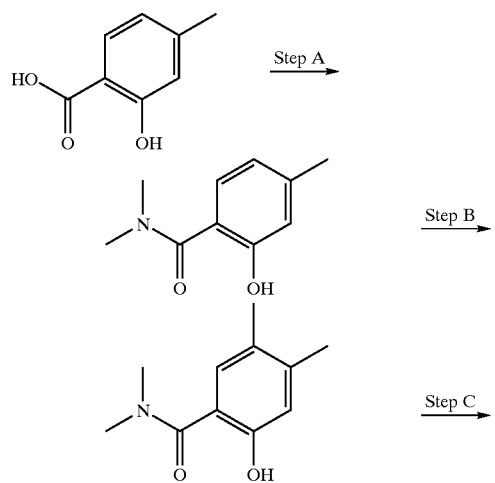

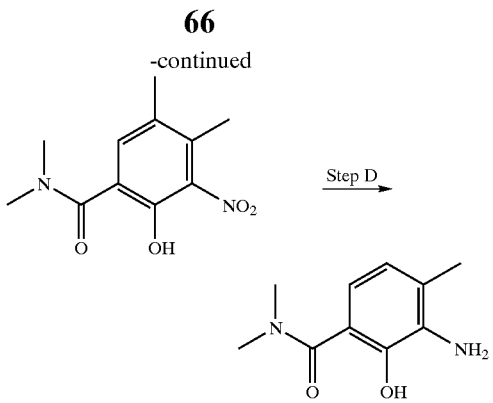

Step A

Following a similar procedure as in Preparative Example 1 except substituting dimethylamine (2M in THF, 50 mL) for (R)-(−)-2-pyrrolidinemethanol and 4-methylsalicylic acid (15 g) for 3-nitrosalicylic acid, the product of step A was prepared (6.3 g, 35%).

Step B

The product from step A above (1.5 g) was combined with iodine (2.1 g), $NaHCO_3$ (1.1 g), EtOH (40 mL) and water (10 mL) and stirred overnight. Filtration, concentration of the filtrate, re-dissolution in $CH_2Cl_2$ and washing with 1M HCl (aq) gave an organic solution which was dried over anhydrous $MgSO_4$, filtered and concentrated in vacuo. Purification by flash column chromatography (silica gel, 0.5–0.7% $MeOH/CH_2Cl_2$) gave the product of step B (0.3 g, 57%, $MH^+$=306).

Step C

Nitric acid (3.8 mL) in AcOH (10 mL) was added to the product from Step B above (0.8 g) and the mixture was stirred for 40 min. The mixture was diluted with water and extracted with $CH_2Cl_2$, dried over anhydrous $MgSO_4$, filtered and concentrated in vacuo to give the product of step C as a solid (0.8 g, 92%, $MH^+$=351).

Step D

A mixture of the product from step C above (800 mg), 10% Pd/C (100 mg), and EtOH/MeOH (40 mL) was stirred in a parr shaker under hydrogen (45 psi) for 1.5 hr. Filtration through celite and concentration in vacuo afforded the title product after purification by preparative plate chromatography (Silica, 10% $MeOH/CH_2Cl_2$, saturated with $NH_4OH$) to give the product of step D (92 mg, 22%, $MH^+$=195).

Preparative Example 27

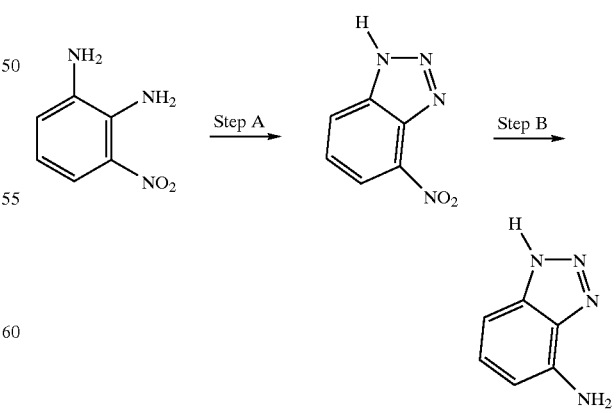

Step A

3-Nitro-1,2-phenylenediamine (10 g), sodium nitrite (5.4 g) and acetic acid (20 mL) were heated at 60° C. overnight, then concentrated-in vacuo, diluted with water and extracted with EtOAc. The product precipitated from the organic phase (5.7 g) as a solid and was used directly in step B.

Step B

The product from Step A above (2.8 g) was stirred with 10% Pd/C (0.3 g) in MeOH (75 mL) under a hydrogen gas atmosphere overnight. The reaction mixture was filtered through celite and the filtrate concentrated in vacuo, to give the product (2.2 g, MH+=135).

Preparative Example 28

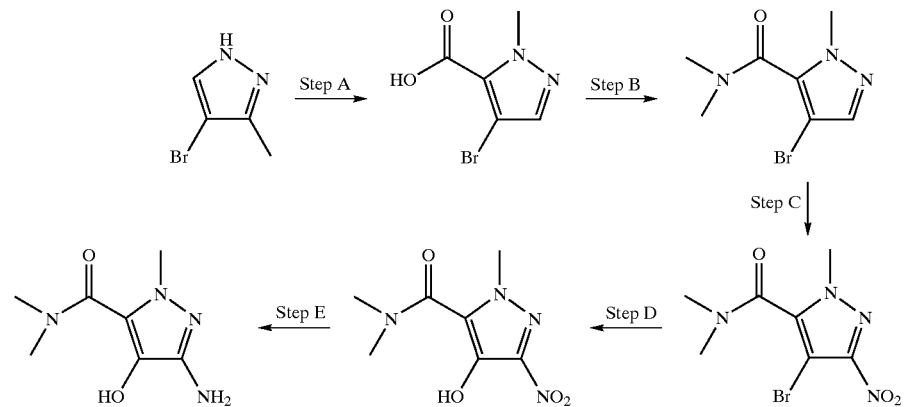

Step A

4-Bromopyrazole-3-carboxylic acid was prepared according to known methods, see: Yu. A. M.; Andreeva, M. A.; Perevalov, V. P.; Stepanov, V. I.; Dubrovskaya, V. A.; and Seraya, V. I. in Zh. Obs. Khim. (Journal of General Chemistry of the USSR) 1982, 52, 2592, and refs cited therein.

Step B

To a solution of 4-bromopyrazole-3-carboxylic acid (2.0 g), available from step A, in 65 mL of anhydrous DMF was added bromotripyrrolidinophosphonium hexafluorophosphate (PyBrop, 4.60 g), dimethyl amine (10 mL, 2.0 M in THF) and diisopropylethyl amine (5.2 mL) at 25° C. The mixture was stirred for 26 h, and concentrated under reduced pressure to an oily residue. This residue was treated with a 1.0 M NaOH aqueous solution, and extracted with ethyl acetate (4×50 mL). The organic extracts were combined, washed with brine, and dried with anhydrous $Na_2SO_4$. Removal of solvents yielded a yellowish oil, which was purified by preparative thin layer chromatography, eluting with $CH_2Cl_2$-MeOH (20:1), to give 1.09 g of the amide (48%, MH$^+$=232.0).

Step C

To a solution of the amide (0.67 g), obtained from step B, in 8 mL of concentrated sulfuric acid at 0° C. was added potassium nitrate (1.16 g) in small portions. The cooling bath was removed and the mixture was heated at 110° C. for 6 h. After cooled to 25° C., the mixture was poured into 80 mL of $H_2O$, and an additional 20 mL of $H_2O$ was used as rinsing. The aqueous mixture was extracted with $CH_2Cl_2$ (100 mL×4). The combined extracts were washed with brine (50 mL), sat. $NaHCO_3$ aqueous solution (50 mL), brine (50 mL), and dried over $Na_2SO_4$. Evaporation of solvent gave a light yellow oil, which solidified on standing. The crude product was purified by flash column chromatography, eluting with $CH_2Cl_2$-MeOH (1:0, 50:1 and 40:1). Removal of solvents afforded 0.521 g (65%) of the product as a solid (MH$^+$=277.1)

Step D

The product (61 mg) obtained from step C was dissolved in 3 mL of THF. To this solution at −78° C. was added dropwise along the inside wall of the flask a 1.6 M solution of n-butyl lithium in hexane. After 45 min, a solution of methyl borate (0.1 mL) in THF (1.0 mL) was added. After 1.5 h, a solution of acetic acid in THF (0.25 mL, 1:10 v/v) was added to the cold mixture. Stirring was continued for 10 min, and a 30 wt % aqueous hydrogen peroxide solution (0.1 mL) was added. An additional portion of hydrogen peroxide aqueous solution (0.05 mL) was added 20 min later. The cooling bath was removed, and the mixture was stirred at 25° C. for 36 h. The yellowish mixture was poured into 30 mL of $H_2O$, and the aqueous mixture was extracted with ethyl acetate (30 mL×4). The extracts were combined, washed with brine (10 mL), 5% $NaHCO_3$ aqueous solution (10 mL) and brine (10 mL). The organic layer was dried with $Na_2SO_4$ and concentrated under reduced pressure to a yellow residue, which was purified by preparative thin layer chromatography eluting with $CH_2Cl_2$-MeOH (20:1) to give the hydroxylated product (5 mg, 10%, MH$^+$=215.3).

Step E

If one were to treat the hydroxylated product of Step D with $H_2$ under the conditions of 10% palladium on carbon in ethanol, one would obtain the hydroxyl-amino compound.

Preparative Example 29

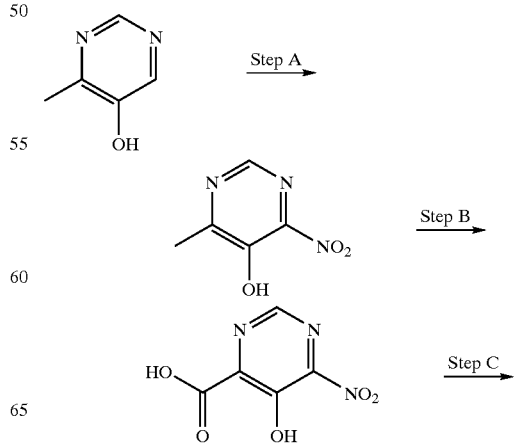

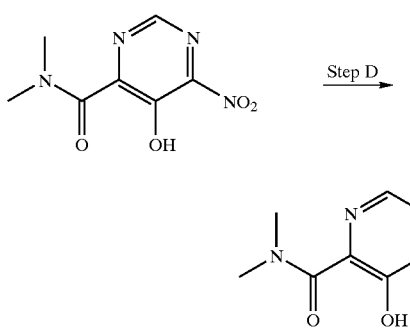

Step A
Following a similar procedure used in Preparative Example 26 Step C except starting with the known compound, 4-methyl-pyrimidin-5-ol, the product of Step A could be prepared.

Step B
Following a similar oxidation procedure used in Preparative Example 28 Step A starting with the product from Step A above, the product of Step B could be prepared.

Step C
Following a similar procedure used in Preparative Example 15 Step A starting with the product from Step B above, the product of Step C could be prepared.

Step D
Following a similar procedure used in Preparative Example 25 Step F starting with the product of Step C above, the product of Step D could be prepared.

Preparative Example 30

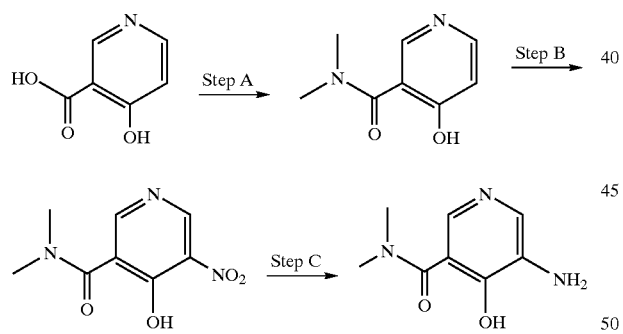

Step A
Following a similar procedure used in Preparative Example 15 Step A starting with the known 4-hydroxynicotinic acid, the product could be prepared.

Step B
Following a similar procedure used in Preparative Example 26 Step C starting with the product from Step A above, the product of Step B could be prepared.

Step C
Following a similar procedure used in Preparative Example 25 Step F starting with product from Step C above, the amine product could be prepared.

Preparative Example 31

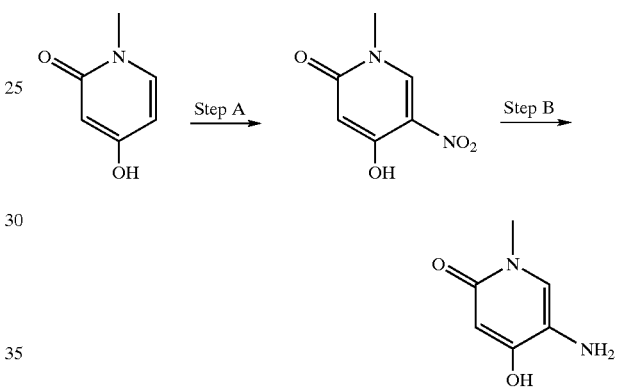

Step A
Following essentially the same procedure used in Preparative Example 26 Step C, the nitro product above could be prepared.

Step B
If one were to stir the nitro product from Step A above, a suitable Pt or Pd catalyst and EtOH under hydrogen atmosphere (1–4 atm), one could obtain the amine product.

Preparative Example 32

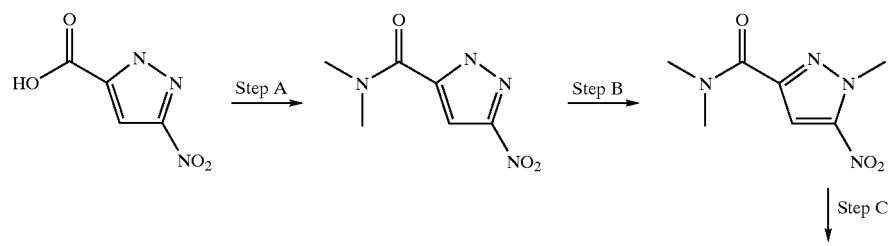

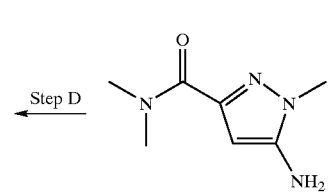
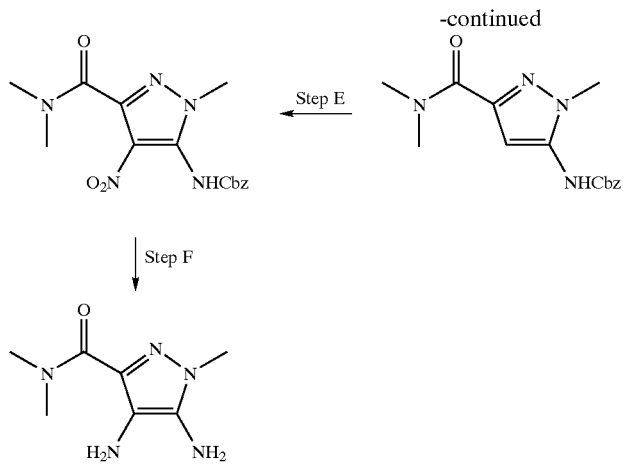

Step A

To a solution of 5-nitro-3-pyrazolecarboxylic acid (5.0 g, 31.83 mmol) in 160 mL of acetonitrile at room temperature was added bromotripyrrolidinophosphonium hexafluorophosphate (PyBrop, 14.9 g, 31.98 mmol) in small portions. A 2.0 M solution of dimethylamine in THF (40.0 mL, 80.0 mmol) was added to the mixture followed by a solution of diisopropylethylamine (14.0 mL, 80.2 mmol). After stirred for 36 h, the mixture was concentrated under reduced pressure to a residue, a mixture of solid and oil. Small volume of $CH_2Cl_2$ was added until all oily material was dissolved and fine colorless solid precipitated out. The solid was collected by filtration as the first crop of the product. The filtrate was concentrated to an oily residue which was treated with a mixture of $CH_2Cl_2$-hexanes (~1:1, v/v), and the colorless precipitation was filtered out as the second crop of the product. The combined solid product was further dried on high vacuum for several hours to afford 5.86 g (100%) of N, N'-dimethyl 5-nitro-3-pyrazolecarboxamide as a solid ($MH^+$=185.0).

Step B

To a solution of N, N'-dimethyl 5-nitro-3-pyrazole amide (5.86 g, 31.83 mmol, available from step A) in 215 mL of anhydrous THF at room temperature was added solid lithium methoxide in small portions. After 45 min, iodomethane was added dropwise. Stirring was continued for 2.5 days. The mixture was filtered through a 1.5-in silica gel pad, rinsing with large excess volume of ethyl acetate. The combined filtrate and rinsing were concentrated to a dark yellow oil, which was purified by flash column chromatography, eluting with hexanes, $CH_2Cl_2$, and $CH_2Cl_2$-MeOH (50:1). Removal of solvents afforded 5.10 g (81%) of N, N'-dimethyl 1-methyl-5-nitro-3-pyrazole amide as a solid ($MH^+$=199.0), contaminated by ~13% of 2-methylated isomer.

Step C

A solution of N, N'-dimethyl 1-methyl-5-nitro-3-pyrazolecarboxamide (5.10 g, 25.29 mmol), obtained from step B, in 250 mL of ethanol was degassed via house vacuum, and then refilled with nitrogen. Solid palladium (10% on activated carbon, wet with <50% water, 2.5 g) was added, the black suspension was degassed via house vacuum and then refilled with hydrogen gas supplied by a gas balloon. The mixture was stirred at room temperature under a hydrogen atmosphere for 4 h, and filtered through a Celite pad, which was rinsed with ethanol. The filtrate and rinsing were combined, concentrated under reduced pressure to give 4.17 g (98%) of the amino-pyrazole product as a solid ($MH^+$=169.0).

Step D

To a stirred solution of amino-pyrazole (1.0 g, 5.95 mmol), prepared in step C, in 40 mL of $CH_2Cl_2$ at room temperature was added benzyl chloroformate (2.7 mL, 17.97 mmol). Solid potassium carbonate (4.1 g, 29.71 mmol) was added in one portion. After 24 h, methanol (5 mL) was added to the mixture, and stirring was continued for additional 2 h. Insoluble material was removed by filtration, and washed with methanol. The combined filtrate and rinsing were concentrated under reduced pressure to a thick syrup, which was separated by preparative TLC ($CH_2Cl_2$-MeOH=30:1). The silica was extracted with MeOH and $CH_2Cl_2$, the extracts were filtered and concentrated under reduced pressure to yield 1.16 g (64%) of the pyrazole benzyl carbamate as a solid ($MH^+$=303.1).

Step E

To a stirred solution of pyrazole benzyl carbamate (1.0 g, 3.31 mmol), obtained from step D, in 100 mL of toluene at room temperature was added "Clayfen" (see note below) (3.5 g) in one portion. The dark purplish suspension was heated to 70° C. and continued at 70–80° C. for 2.5 d. After cooled to room temperature, the mixture was filtered through a thin Celite pad. The solid residue and the filtration pad were rinsed with $CH_2Cl_2$, and filtered. The combined filtrates were concentrated to a yellowish oil, which was purified by preparative TLC ($CH_2Cl_2$-MeOH=20:1). The silica was extracted with $CH_2Cl_2$ and methanol, the extracts were filtered and concentrated under reduced pressure to give 0.822 g (72%) of the nitro-pyrazole benzyl carbamate as a yellowish oil ($MH^+$=348.1). Note: "Clayfen", clay-supported Iron (III) nitrate, was prepared according to literature procedures, see: Cornelis, A.; Laszlo, P. *Synthesis*, 1980, 849. To a stirred acetone solution (30 mL) at room temperature was added solid $Fe(NO_3)_3.9H_2O$ (1.8 g) in small portions. After 5 min, K-10 bentonite clay (2.4 g) was added. Stirring was continued for 30 min, and the resulting suspension was concentrated under reduced pressure (water bath temperature <=30° C.). The freshly prepared material was used right away in the reaction above.

Step F

A solution of nitro-pyrazole benzyl carbamate (410.0 g, 1.18 mmol), available from step E, in 20 mL of ethanol was degassed via house vacuum, and refilled with nitrogen. Solid palladium (10% on activated carbon, wet with <50% $H_2O$, 280.0 mg) was added. The black suspension was degassed via house vacuum, and refilled with hydrogen gas supplied by a gas balloon. The mixture was stirred for 20 h under a hydrogen atmosphere, and filtered through a 1-in Celite pad, rinsing with excess volume of methanol. The filtrate and rinsing were concentrated to a reddish oil, which was purified by preparative TLC ($CH_2Cl_2$-MeOH=15:1). The silica was extracted with methanol, the extracts were filtered, and the filtrate was concentrated under reduced pressure to an oil, which solidified while being dried on high vacuum, yielding 120.0 mg (56%) of diamino-pyrazole product ($MH^+$=184.0).

Preparative Example 33

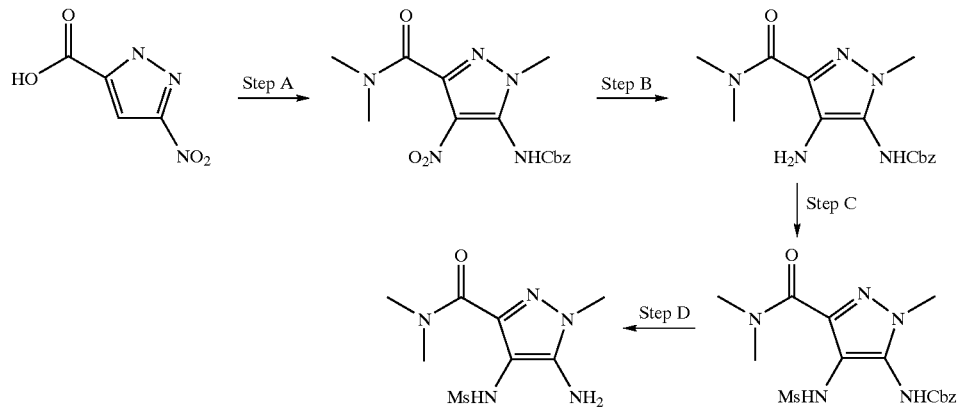

Step A
Nitro-pyrazole benzyl carbamate was prepared from 5-nitro-3 pyrazolecarboxylic acid according to the procedure described in Preparative Example 32.

Step B
To a solution of nitro-pyrazole benzyl carbamate (410.0 mg, 1.18 mmol), obtained from step A, in 17 mL of ethyl acetate at room temperature was added Tin (II) chloride dihydrate (1.33 g, 5.90 mmol) in one portion. The mixture was heated to 80° C. and continued for 2 h. After cooled to room temperature, a saturated $NaHCO_3$ aqueous solution was added dropwise to the mixture until pH approximately 7. An additional volume of ethyl acetate (20 mL) was added, the mixture was stirred overnight, and filtered through a 1-in Celite pad. The two layers of the filtrate were separated. The organic layer was washed with brine once. The aqueous washing was combined with the aqueous layer, and extracted with ethyl acetate once. The combined organic layers were dried with $Na_2SO_4$, filtered and concentrated, further dried on high vacuum, to afford 361.5 mg (97%) of amino-pyrazole benzyl carbamate as a solid ($MH^+$=318.1).

Step C
To a stirred solution of amino-pyrazole benzyl carbamate (180.0 mg, 0.57 mmol), prepared in step B, in 11 mL of $CH_2Cl_2$ at −78° C. was added triethylamine (0.32 mL, 2.30 mmol). A 1.0 M solution of methanesulfonyl chloride in $CH_2Cl_2$ (1.7 mL, 1.7 mmol) was added dropwise along the inside wall of the flask. The mixture was stirred for 2.5 h while the temperature of the cooling bath was increased slowly from −78° C. to −25° C. A saturated $NaHCO_3$ aqueous solution (5 mL) was added to the mixture, and it was further diluted with 25 mL of $CH_2Cl_2$. The cooling bath was removed, stirring was continued for an additional 1.5 h, and the layers were separated. The aqueous layer was extracted with $CH_2Cl_2$ (30 mL), and the combined organic layers were washed with a saturated $NaHCO_3$ aqueous solution (30 mL) and brine (30 mL). The organic layer was dried by $Na_2SO_4$, and concentrated to an oil, which was purified by preparative TLC ($CH_2Cl_2$-MeOH=20:1). The silica was extracted with $CH_2Cl_2$ and methanol, the extracts were filtered and concentrated to a colorless oil, solidified while being dried on high vacuum, yielding 185.7 mg (83%) of the pyrazole methylsulfonamide as a solid ($MH^+$=396.1).

Step D
To a nitrogen flushed solution of pyrazole methylsulfonamide (275.0 mg, 0.70 mmol), from step C, in 10 mL of ethanol was added solid palladium (10% on activated carbon, wet with <50% water, 550.0 mg). The suspension was degassed via house vacuum, then filled with hydrogen gas supplied by a gas balloon. The mixture was stirred for 3.5 h under a hydrogen atmosphere, and filtered through a layer of Celite. The solid residue and the filtration pad were rinsed with ethanol and ethyl acetate, the combined filtrate and rinsing were concentrated under reduced pressure to give 173.0 mg (95%) of amino-pyrazole methylsulfonamide as a solid ($MH^+$=262.0).

Preparative Example 34

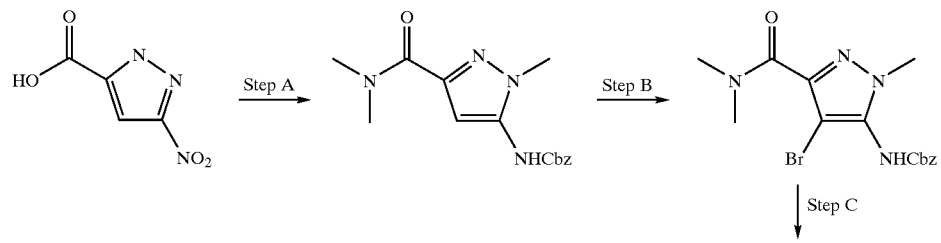

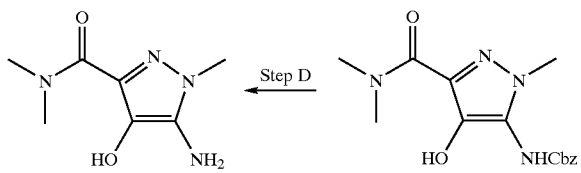

Step A
Pyrazole benzyl carbamate was prepared from 5-nitro-3-pyrazolecarboxylic acid in 4 steps according to the procedure described in Preparative Example 32.

Step B
To a solution of pyrazole benzyl carbamate (115.0 mg, 0.38 mmol), prepared in step A, in 6 mL of $CH_2Cl_2$ at room temperature was added solid potassium carbonate in one portion. A solution of bromine was added dropwise to the stirred mixture. After 6 h, 30 mL of $H_2O$ was added, and the mixture was extracted with $CH_2Cl_2$ (30 mL×3). The combined organic extracts were washed with a 10% $Na_2S_2O_3$ aqueous solution (20 mL), a saturated $NaHCO_3$ aqueous solution (20 mL) and brine (20 mL), and dried with $Na_2SO_4$. Evaporation of solvent gave a slightly yellow oil, which was purified by preparative TLC ($CH_2Cl_2$-MeOH=20:1). The silica was extracted with $CH_2Cl_2$ and methanol, the extracts were filtered and concentrated under reduced pressure to afford an oil, which was further dried on high vacuum, yielding 134.2 mg (93%) of the bromo-pyrazole benzyl carbamate ($MH^+$=381).

Step C
If one were to treat the bromo-pyrazole benzyl carbamate compound from step B with n-butyl lithium followed by methyl borate, it would convert the bromo-pyrazole benzyl carbamate to the corresponding boronic ester. Subsequent one-pot oxidation of the boronic ester with $H_2O_2$ aqueous solution would afford the hydroxy-pyrazole benzyl carbamate.

Step D
Treatment of the hydroxy-pyrazole benzyl carbamate from step C with hydrogen under the conditions of palladium (10% on activated carbon) in ethanol would afford the desired amino-hydroxy pyrazole.

Preparative Example 35

Step A
To a solution of methyl 3-methoxythiophene carboxylate (2.0 g, 11.6 mmol) in 20 mL of THF at room temperature was added dropwise a 1.0 M sodium hydroxide aqueous solution (17.0 mL, 17.0 mmol). After addition, the mixture was heated to 75° C. (oil bath temperature) and continued for 18 h. The mixture was cooled to room temperature, treated with a 1.0 M hydrochloride aqueous solution until pH approximately being 2. The acidified mixture was extracted with 100 mL of $CH_2Cl_2$—$CH_3CN$ (1:1, v/v), 50 mL of $CH_2Cl_2$, and 50 mL of $CH_3CN$. The combined organic extracts were washed with brine (30 mL), dried over $Na_2SO_4$, and concentrated under reduced pressure to a solid, which was further dried on high vacuum, yielding 1.84 g (100%) of 3-methoxythiophene carboxylic acid ($MH^{+=}$ 159.0).

Step B
To a suspension of 3-methoxythiophene carboxylic acid (1.84 g, 11.61 mmol), from step A, in 60 mL of acetonitrile at room temperature was added bromotripyrrolidinophosphonium hexafluorophosphate (PyBrop, 5.40 g, 11.60 mmol), dimethyl amine (2.0 M in THF, 14.5 ml, 29.0 mmol) and diisopropylethyl amine (5.0 mL, 28.63 mmol) successively. After stirred for 1.5 day, the mixture was concentrated under reduced pressure to a yellow oil, which was purified by preparative TLC ($CH_2Cl_2$-MeOH=40:1). The silica was extracted with $CH_2Cl_2$ and methanol, the extracts were filtered and concentrated to an oil, which was further dried on high vacuum, yielding 4.16 g of N,N-dimethyl 3-methoxythiophene amide (contaminated by PyBrop impurity) ($MH^+$=186.0).

Step C
To a vigorously stirred solution of thiophene amide (4.16 g, prepared in step B) in 6 mL of concentrated sulfuric acid at −10° C. was added dropwise fuming nitric acid (0.6 mL, 14.28 mmol). After 1.5 h, the mixture was poured into 80 mL

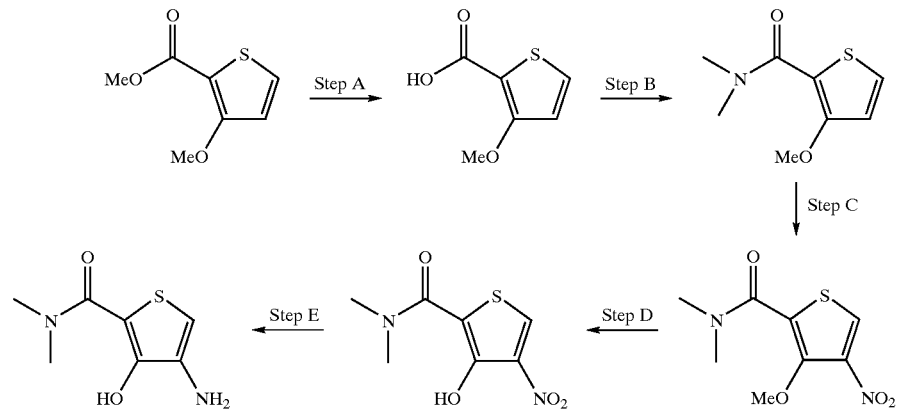

of a mixture of 1.0 M NaOH aqueous solution and ice (1:1, v/v). An additional 40 mL of H₂O was used to facilitate the transfer. The yellow precipitates were collected by filtration, washed with H₂O twice, and dried on high vacuum, to give 1.67 g of the nitro-thiophene product. The aqueous filtrates were extracted with CH₂Cl₂ (50 mL×3). The extracts were washed with a sat. NaHCO₃ aqueous solution (30 mL) and brine (30 mL), and dried with Na₂SO₄. Evaporation of solvent afforded a yellow oil, which was purified by preparative TLC (CH₂Cl₂-MeOH=50:1) to give an additional 0.144 g of the nitro-thiophene as a solid (1.81 g total, 68% over two steps, MH⁺=231.0).

Step D

To a vigorously stirred solution of methoxy-nitro-thiophene (900.0 mg, 3.91 mmol), obtained from step C, in 55 mL of anhydrous CH₂Cl₂ at −78° C. was added dropwise along the inside wall of the flask a 1.0 M solution of boron tribromide in CH₂Cl₂ during a 15 min period. The mixture was stirred for 4 h while the temperature of the cooling bath was increased slowly from −78° C. to −10° C., and poured into 100 mL of a mixture of ice and H₂O (~1:1, v/v). Additional 30 mL of H₂O and 30 mL of CH₂Cl₂ were used to rinse the flask. The combined mixture was stirred at room temperature over night, the two layers were separated, and the aqueous layer was extracted with CH₂Cl₂ (50 mL×3). The organic layers were combined, washed with a sat. NaHCO₃ aqueous solution (50 mL×2) and brine (50 mL×2), dried with Na₂SO₄, and concentrated to a yellow solid. The crude product was purified by flash column chromatography, eluting with hexanes, CH₂Cl₂-hexanes (1:1 and 2:1). Removal of solvents afforded a solid, which was further dried on high vacuum, giving 615.2 mg (73%) of the hydroxy-nitro-thiophene amide (MH⁺=217.0).

Step E

To a nitrogen flushed solution of hydroxy-nitro-thiphene amide (610.0 mg, 2.82 mmol), prepared in step D, in 60 mL of ethanol was added palladium hydroxide (20 wt % on activated carbon, wet with <=50% water, 610.0 mg). The suspension was degassed via house vacuum and refilled with hydrogen gas from a gas balloon. The mixture was first stirred at room temperature under a hydrogen atmosphere for 2 h, then heated to 70–80° C. and continued for 20 h. Solid material was removed by filtration through a 1-in Celite pad, the filtration pad was washed with 100 mL of ethanol, and the combined filtrates were concentrated to a light yellow solid. The crude product was treated with a mixture of CH₂Cl₂-MeOH (~1:1, v/v), off-white solids precipitated out and collected by filtration as the first crop of the product (75.4 mg). The filtrate was concentrated to a solid residue, which was purified by flash column chromatography, eluting with CH₂Cl₂-EtOH (10:1 and 2:1). Removal of solvents afforded 226.8 mg of the amino-hydroxy-thiophene amide as a solid (302.2 mg total, 58%, MH⁺=187.0).

Preparative Example 36

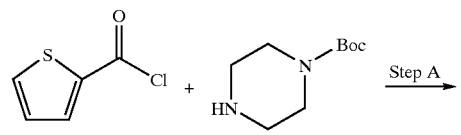

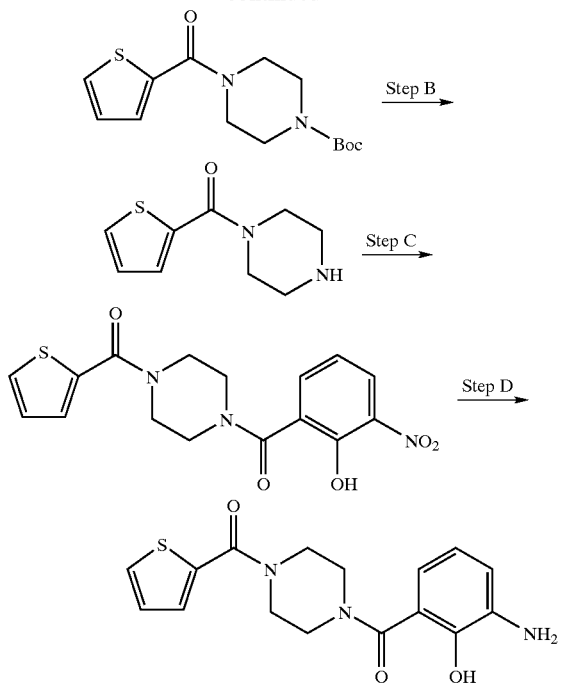

Step A

2-Thiophenecarbonyl chloride (2.0 mL, 18.7 mmol) was dissolved in 100 mL dichloromethane. After addition of diisopropylethylamine (4.1 mL, 23.4 mmol) and Boc-piperazine (3.66 g, 19.7 mmol), the mixture was stirred for 4 h at room temperature. The resulting cloudy mixture was put into water (500 mL) and acidified with 3N HCl to pH~1. Extraction with dichloromethane (2×100 mL) and drying over sodium sulfate resulted in sufficiently pure product that was used in the next step without any further purification.

¹H NMR (300 MHz, d₆-DMSO) 1.60 (s, 9H), 3.29 (dd, 4H), 3.69 (dd, 4H), 7.23 (dd, 1H), 7.49 (d, 1H), 7.79 (d, 1H).

Step B

The crude material from Step A was dissolved in trifluoroacetic acid/dichloromethane (75 mL, 4/1). After stirring for 2 h, the reaction mixture was put into 1N sodium hydroxide (400 mL). Extraction with dichloromethane (2×100 mL) and drying over sodium sulfate resulted in sufficiently pure product that was used in Step C without any further purification.

¹H NMR (300 MHz, d₆-DMSO) 2.81 (dd, 4H), 3.63 (dd, 4H), 7.21 (dd, 1H), 7.46 (d, 1H), 7.82 (d, 1H).

Step C

The crude material (3.50 g, 17.8 mmol) from Step B was dissolved in dichloromethane (100 mL). After addition of diisopropylethylamine (18.7 mL, 107 mmol), 3-nitrosalicylic acid (3.3 g, 18.0 mmol), and PyBrOP (10.4 g, 22.3 mmol), the resulting yellow mixture was stirred over night at room temperature before being put into 1N sodium hydroxide (200 mL). Extraction with dichloromethane (2×200 mL) removed all PyBrOP by-products. The aqueous phase was acidified with 3N HCl and subsequently extracted with dichloromethane (3×100 mL). The combined organic phases of the acidic extraction were dried over sodium sulfate, concentrated, and finally purified by column chromatography (dichloromethane/methanol=10/1) to yield the desired product (2.31 g, 34% over 3 steps).

¹H NMR (300 MHz, d₆-DMSO) 3.30–3.90 (m, 8H), 7.10–8.20 (m, double signals due to E/Z-isomers, 6H), 10.82 (s, 1H).

Step D

The nitro-compound (2.3 g, 6.4 mmol) from Step C was dissolved in methanol (50 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol=10/1) to yield the desired product (1.78 g, 84%).

$^1$H NMR (300 MHz, $d_6$-DMSO) 3.30–3.90 (m, 8H), 7.22 (m, 2H), 7.55 (d, 1H), 7.71 (d, 1H), 7.88 (d, 1H), 8.15 (d, 1H), 10.85 (bs, 1H).

Preparative Example 37

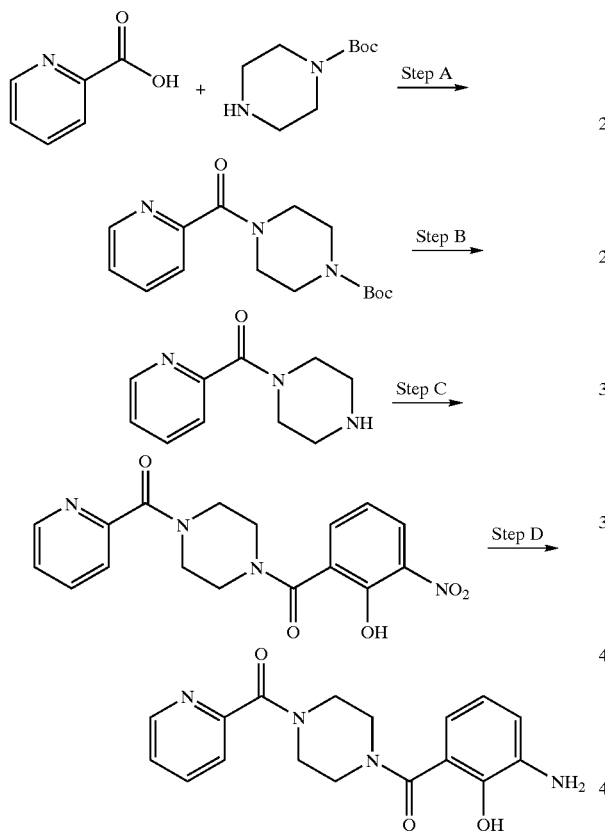

Step A

Picolinic acid (3.0 g, 24.3 mmol) was suspended in $SOCl_2$ (15 mL). After addition of dimethylformamide (5 drops), the reaction mixture was stirred for 4 hours. During this period the color changed from white to green to brown to finally dark wine-red and all solid went into solution. Evaporation of the solvent yielded the corresponding acid chloride as HCl-salt. Without any further purification, the solid was suspended in 120 mL dichloromethane. After addition of diisopropylethylamine (12.7 mL, 73 mmol) and Boc-piparazine (4.8 g, 25.5 mmol), the reaction was stirred over night at room temperature. The resulting cloudy mixture was put into water (500 mL) and extracted with dichloromethane (2×100 mL). Drying over sodium sulfate resulted in sufficiently pure product that was used in Step B without any further purification.

$^1$H NMR (300 MHz, $d_6$-DMSO) 1.63 (s, 9H), 3.21 (dd, 4H), 3.61 (dd, 4H), 7.57 (dd, 1H), 7.63 (d, 1H), 7.98 (dd, 1H), 8.70 (d, 1H).

Step B

The crude material from Step A was dissolved in trifluoroacetic acid/dichloromethane (75 mL, 4/1). After stirring for 2 days, the reaction mixture was put into 1N sodium hydroxide (400 mL). Extraction with dichloromethane (2×100 mL) and drying over sodium sulfate resulted in sufficiently pure product that was used in Step C without any further purification.

$^1$H NMR (300 MHz, $d_6$-DMSO) 2.77 (dd, 2H), 2.83 (dd, 1H), 3.38 (dd, 2H), 3.64 (dd, 1H), 7.58 (dd, 1H), 7.62 (d, 1H), 8.00 (dd, 1H), 8.67 (d, 1H).

Step C

The crude material (1.35 g, 7.06 mmol) from Step B was dissolved in dichloromethane (50 mL). After addition of diisopropylethylamine (3.7 mL, 21.2 mmol), 3-nitrosalicylic acid (1.36 g, 7.41 mmol), and PyBrOP (3.62 g, 7.77 mmol), the resulting yellow mixture was stirred over night at room temperature before being put into 1N sodium hydroxide (300 mL). Extraction with dichloromethane (2×100 mL) removed any PyBrOP products. The aqueous phase was acidified with 3N HCl. Careful adjustment of the pH with saturated sodium carbonate solution to almost neutral crushed the desired compound out of solution. The aqueous phase was subsequently extracted with dichloromethane (3×100 mL). The combined organic layers of the neutral extraction were dried over sodium sulfate, concentrated, and finally purified by column chromatography (dichloromethane/methanol=20/1) to yield the desired product (1.35 g, 16% over 3 steps).

$^1$H NMR (300 MHz, $d_6$-DMSO) 3.30–3.95 (m, 8H), 7.22 (m, 1H), 7.61 (m, 1H), 7.73 (d, 2H), 8.03 (m, 1H), 8.17 (m, 1H), 8.69 (m, 1H), 10.82 (s, 1H).

Step D

The nitro-compound (1.35 g, 3.79 mmol) from Step C was dissolved in methanol (60 mL) and stirred with 10% Pd/C under a hydrogen gas atmosphere over night. The reaction mixture was filtered through Celite and washed thoroughly with methanol. Finally, the filtrate was concentrated in vacuo and purified by column chromatography (dichloromethane/methanol=20/1) to yield the desired product (1.10 g, 89%).

$^1$H NMR (300 MHz, $d_6$-DMSO) 3.50–3.85 (m, 8H), 6.47 (dd 1H), 6.74 (m, 2H), 7.59 (dd, 1H), 7.71 (d, 1H), 8.04 (dd, 1H), 8.68 (d, 1H).

Preparative Example 38

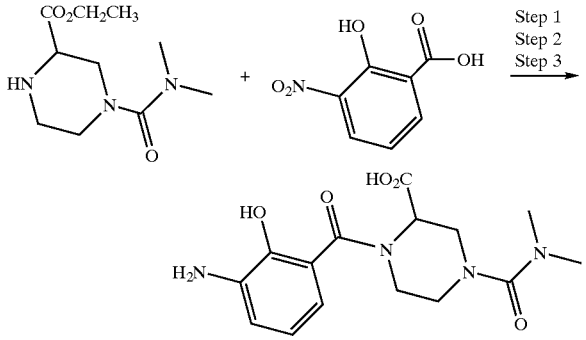

Step 1

3-Nitrosalicylic acid (3.61 g, 0.0197 g), DCC (2.03 g, 0.0099 mol) and ethyl acetate (130 mL) were combined in a round bottom flask and stirred for 15 min. 4-Dimethylcarbamoyl-piperazine-2-carboxylic acid ethyl ester (4.51 g, 0.0197g) was added, and the reaction was stirred for 72 hours. The reaction mixture was concentrated then dissolved in dichloromethane. The organic phase was washed once with 0.1N sodium hydroxide. The aqueous phase was back extracted once with dichloromethane. The aqueous phase was acidified and wash three times with ethyl acetate. The aqueous phase was concentrated and purified by column chromatography (5% methanol/DCM).

MS: calculated: 394.15, found:395.0

$^1$H NMR (300 MHz, CDCl$_3$) 1.32 (t, 3H), 2.86 (m, 7H), 3.15 (m, 1H), 3.51 (m, 4H), 4.24 (m, 3H), 7.15 (m, 1H), 7.66 (m, 1H), 8.20 (m, 1H), 10.86 (bs, 1H).

Step 2

4-Dimethylcarbamoyl-1-(2-hydroxy-3-nitro-benzoyl)-piperazine-2-carboxylic acid ethyl ester (0.80 g, 0.002 mol) and methanol (50 mL) were combined in a round bottom flask. The system was purged with argon. To the solution was added 5% palladium on carbon (~100 mg). The flask was purged with hydrogen and stirred overnight. The reaction was filtered through a pad of celite and washed with methanol. The material was concentrated then purified by column chromatography (6% methanol/DCM). Isolated product (0.74 g, 0.002 mol, 100%).

MS: calculated: 364.17, found:365.1

$^1$H NMR (300 MHz, CDCl$_3$) 1.27 (t, 3H), 2.85 (m, 8H), 3.18 (1H), 3.45 (m, 3H), 4.19 (m, 3H), 3.90 (m, 3H)

Step 3

1-(3-Amino-2-hydroxy-benzoyl)-4-dimethylcarbamoyl-piperazine-2-carboxylic acid ethyl ester (0.74 g, 0.002 mol) was suspended in a solution of dioxane (10 mL) and water (10 mL). Lithium hydroxide (0.26 g, 0.0061 mol) was added and the mixture stirred for two hours. The solution was acidified to pH=6 with 3N HCl then extracted with butanol. The extracts were combined, dried over sodium sulfate and concentrated.

MS: calculated: 336.14, found:337.1

$^1$H NMR (300 MHz, CD$_3$OD) 2.86 (m, 7H), 3.23 (m, 3H), 3.54 (m, 3H), 6.92 (m, 2H), 7.23 (m, 1H).

Preparative Example 39

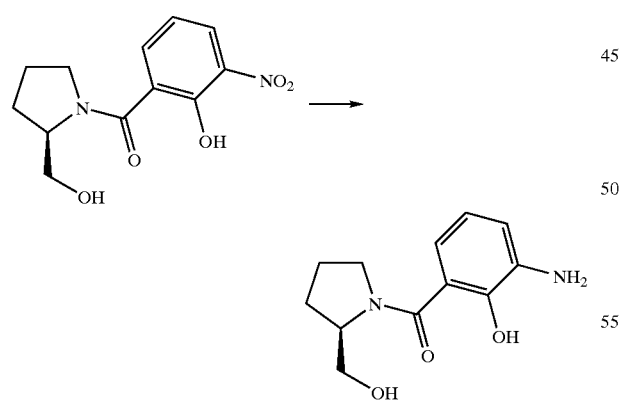

The product from Preparative Example 1 was stirred with 10% Pd/C under a hydrogen gas atmosphere overnight. The reaction mixture was filtered through celite, the filtrate concentrated in vacuo, and the resulting residue purified by column chromatography (silica gel, 4% MeOH/CH$_2$Cl$_2$ saturated with NH$_4$OH) to give the product (129 mg, 43%, MH+=237).

Preparative Example 39.1

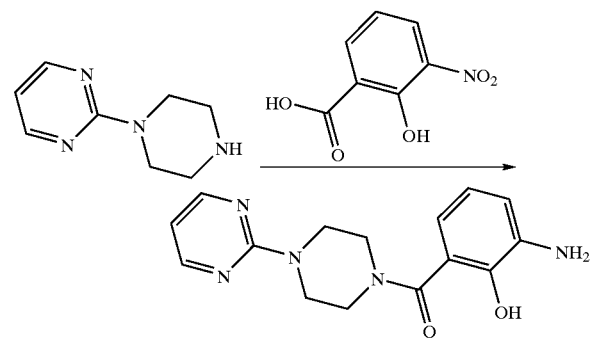

In essentially the same manner as was described in Preparative Example 39, the amine product above was obtained (50% yield, MH$^+$=300.1).

Preparative Example 40

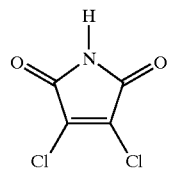

The compound above is prepared according to the literature procedure Am. Chem. J.; 18; 1896; 334.

Preparative Example 41

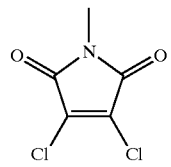

The compound above is commercially available from Maybridge Chemical Co.

Preparative Example 42

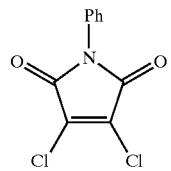

The compound above is commercially available from Salor Chemical Co.

Preparative Example 43

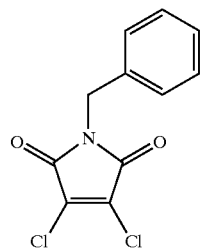

The compound above is commercially available from Maybridge Chemical Co.

Preparative Example 44

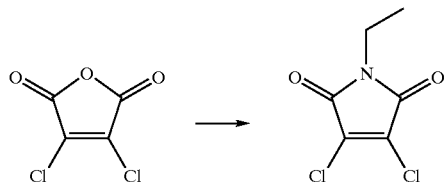

If one were to follow the procedure described in Bioorg. Med. Chem.; 7; 6; 1999; 1067–1074 but using ethyl amine instead of methyl amine, one could obtain the product above.

Preparative Example 45

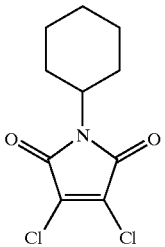

The compound above is prepared according to the literature procedure Chem. Heterocycl. Compd. 1992, 28, 331–335.

Preparative Example 50

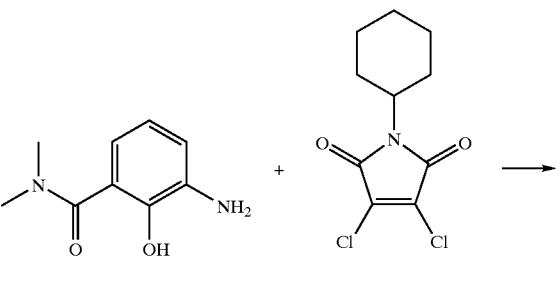

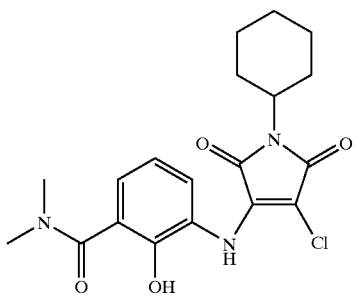

If one were to follow the procedure outlined in the literature: Chem. Heterocycl. Compd. 1992, 28, 331–335, but using the product from Preparative Example 3 instead of pyrrolidine, then one would obtain the poduct above.

Preparative Example 51–112

Following the procedure set forth in Preparative Example 50 but using the amine from the Preparative Example indicated and the appropriate dichloro compound from the Preparative Example indicated, the chloro intermediate products listed in the table below would be obtained.

| Prep Ex. | Prep Ex of Amine | Prep Ex of Dichloro | Product |
|---|---|---|---|
| 51 | 3 | 40 | 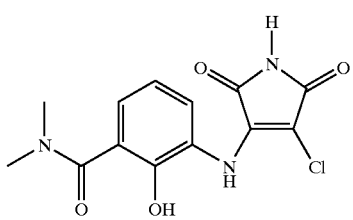 |

-continued

| Prep Ex. | Prep Ex of Amine | Prep Ex of Dichloro | Product |
| --- | --- | --- | --- |
| 52 | 6 | 40 | |
| 53 | 8 | 40 | |
| 54 | 7 | 40 | |
| 55 | 37 | 40 | |
| 56 | 38 | 40 | |
| 57 | 29 | 40 | |

-continued

| Prep Ex. | Prep Ex of Amine | Prep Ex of Dichloro | Product |
|---|---|---|---|
| 58 | 25 | 40 | |
| 59 | 35 | 40 | |
| 61 | 28 | 40 | |
| 63 | 26 | 40 | |
| 64 | 33 | 40 | |
| 65 | 34 | 40 | |

-continued
| Prep Ex. | Prep Ex of Amine | Prep Ex of Dichloro | Product |
|---|---|---|---|
| 66 | 32 | 40 | 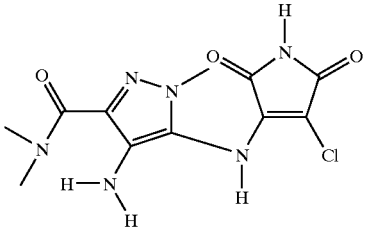 |
| 67 | 3 | 41 | 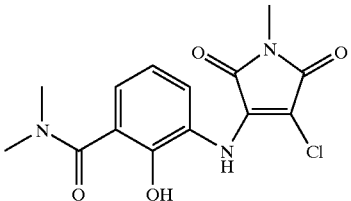 |
| 68 | 6 | 41 | 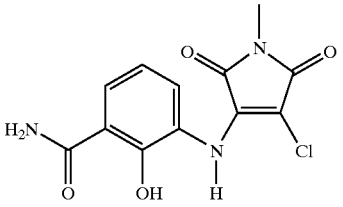 |
| 69 | 4 | 41 | 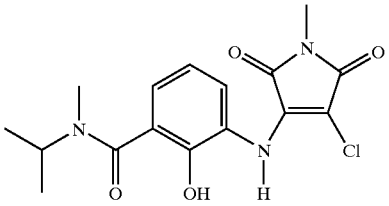 |
| 70 | 11 | 41 | 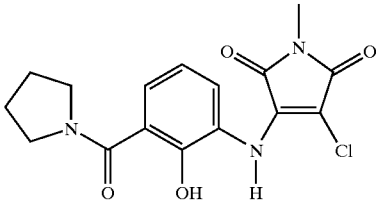 |
| 71 | 8 | 41 | 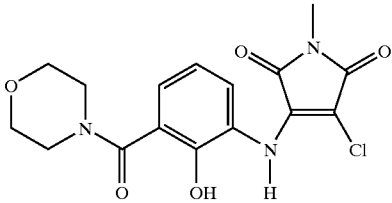 |
| 72 | 12 | 41 | 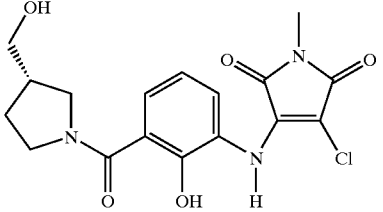 |

-continued

| Prep Ex. | Prep Ex of Amine | Prep Ex of Dichloro | Product |
|---|---|---|---|
| 73 | 7 | 41 | |
| 74 | 39.1 | 41 | |
| 75 | 37 | 41 | |
| 76 | 36 | 41 | |
| 77 | 38 | 41 | |
| 78 | 29 | 41 | |

-continued
| Prep Ex. | Prep Ex of Amine | Prep Ex of Dichloro | Product |
|---|---|---|---|
| 79 | 30 | 41 | 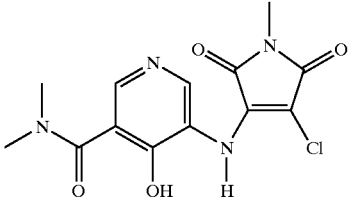 |
| 80 | 31 | 41 | 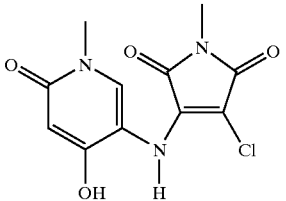 |
| 81 | 25 | 41 | 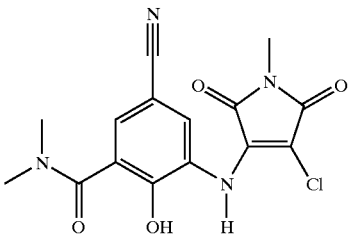 |
| 82 | 27 | 41 | 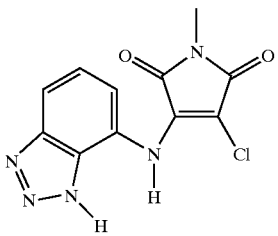 |
| 83 | 35 | 41 | 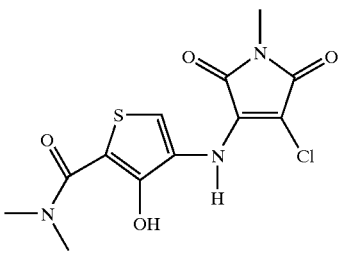 |
| 85 | 28 | 41 | 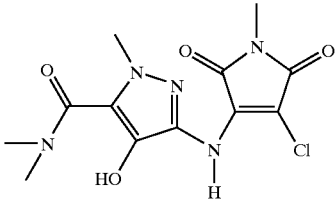 |

-continued
| Prep Ex. | Prep Ex of Amine | Prep Ex of Dichloro | Product |
|---|---|---|---|
| 87 | 26 | 41 | 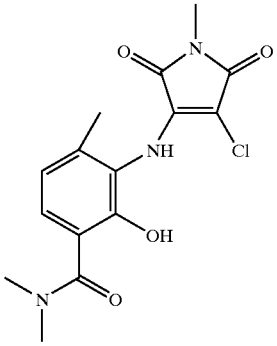 |
| 88 | 33 | 41 | 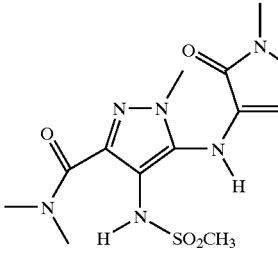 |
| 89 | 34 | 41 | 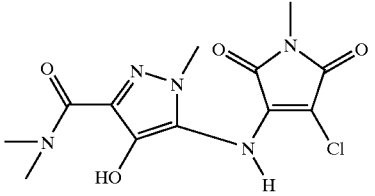 |
| 90 | 32 | 41 | 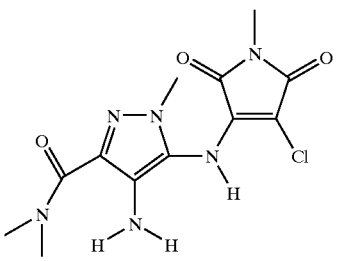 |
| 91 | 3 | 44 | 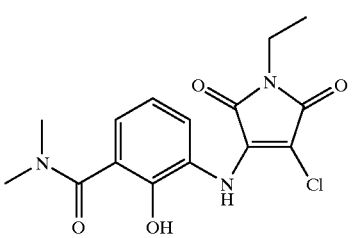 |
| 92 | 8 | 44 | 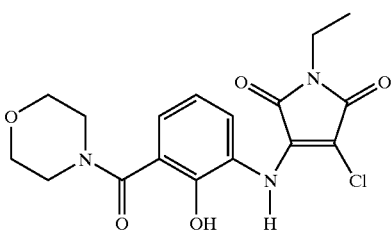 |

-continued
| Prep Ex. | Prep Ex of Amine | Prep Ex of Dichloro | Product |
|---|---|---|---|
| 93 | 7 | 44 | 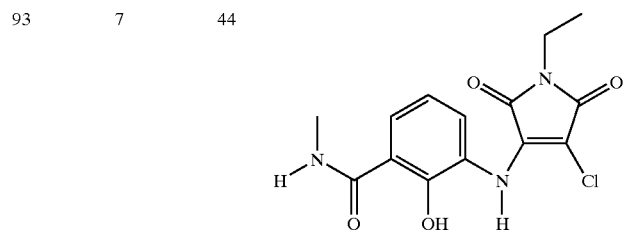 |
| 94 | 25 | 44 | 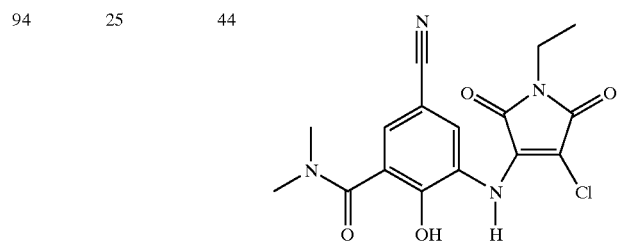 |
| 95 | 30 | 44 | 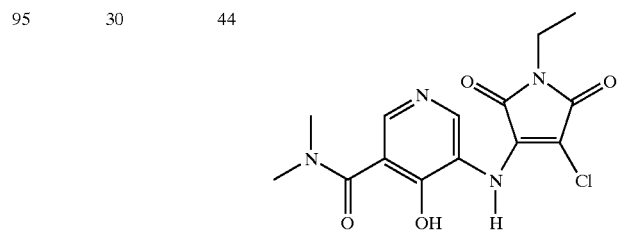 |
| 96 | 3 | 45 | 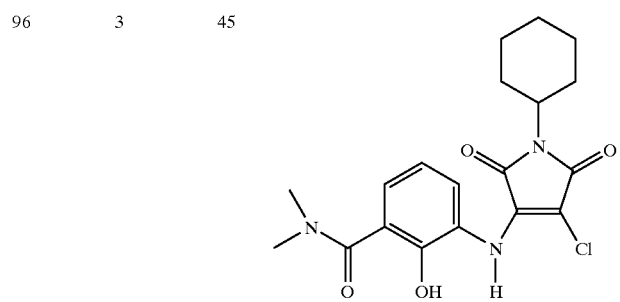 |
| 97 | 8 | 45 | 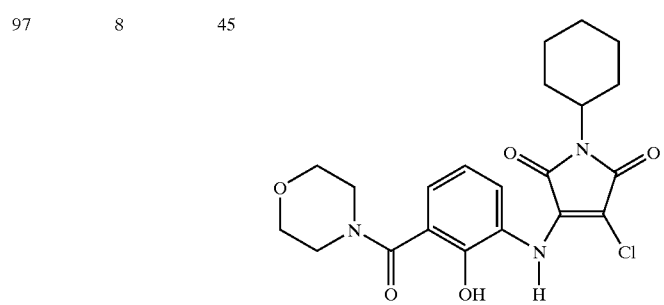 |

-continued
| Prep Ex. | Prep Ex of Amine | Prep Ex of Dichloro | Product |
|---|---|---|---|
| 98 | 7 | 45 | 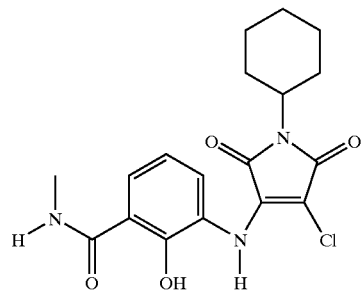 |
| 99 | 25 | 45 | 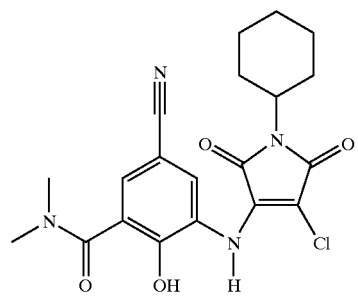 |
| 100 | 30 | 45 | 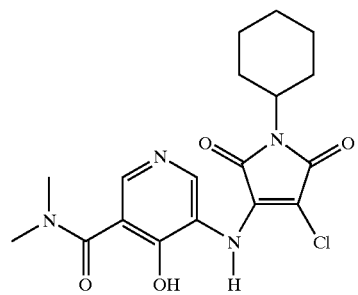 |
| 101 | 3 | 42 | 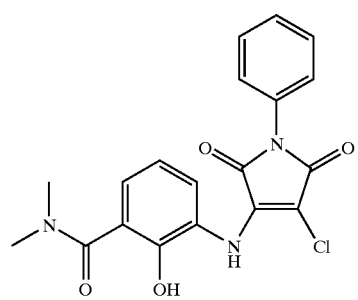 |
| 102 | 8 | 42 | 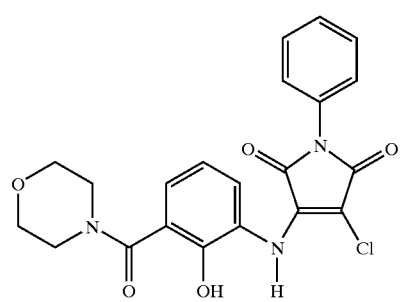 |

-continued
| Prep Ex. | Prep Ex of Amine | Prep Ex of Dichloro | Product |
|---|---|---|---|
| 103 | 7 | 42 | 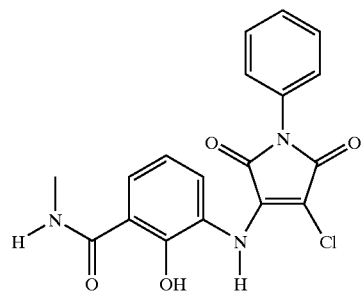 |
| 104 | 25 | 42 | 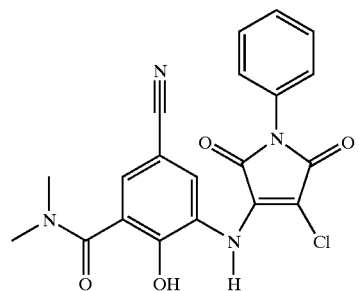 |
| 105 | 30 | 42 | 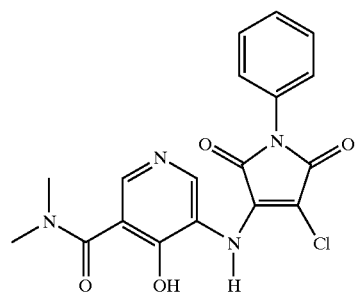 |
| 106 | 3 | 43 | 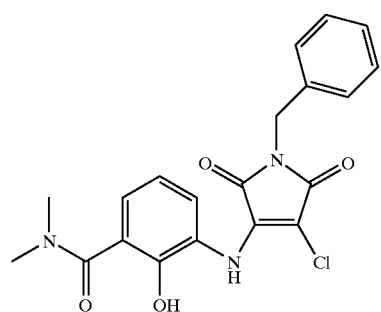 |
| 107 | 8 | 43 | 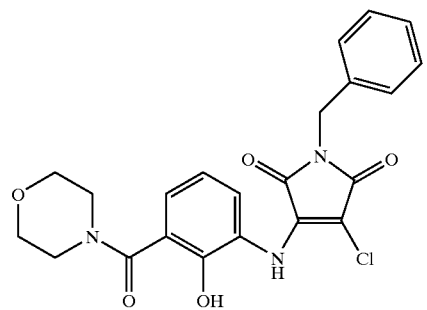 |

-continued
| Prep Ex. | Prep Ex of Amine | Prep Ex of Dichloro | Product |
|---|---|---|---|
| 108 | 7 | 43 | 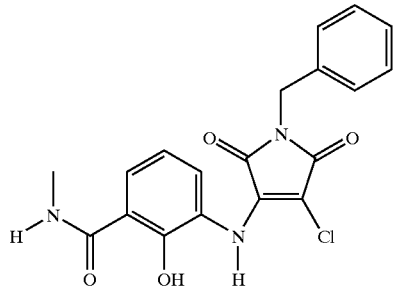 |
| 109 | 25 | 43 | 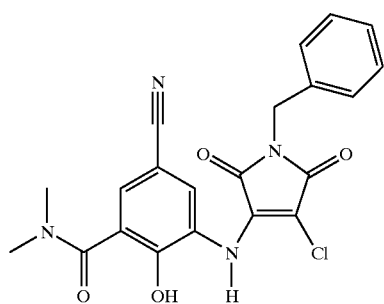 |
| 110 | 30 | 43 | 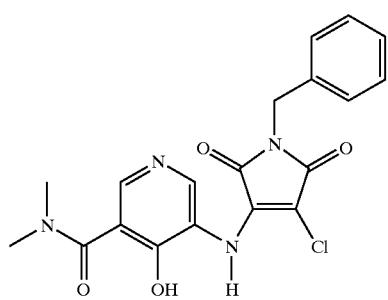 |
| 111 | From: Aldrich Chemical Co. | 41 | 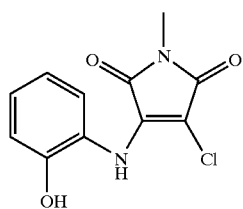 |
| 112 | 30 | 40 | 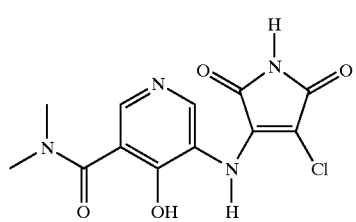 |

Preparative Example 120

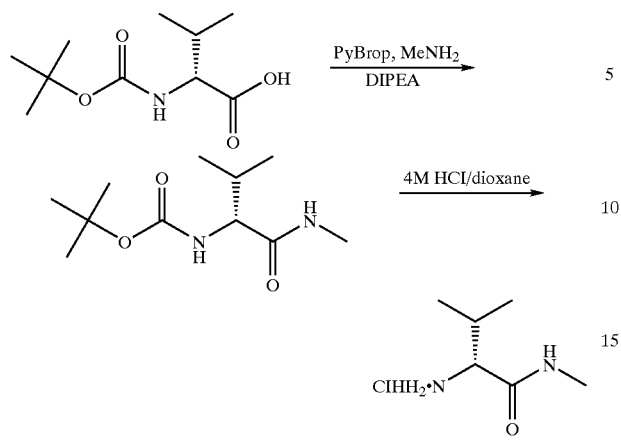

Step A

To a solution of N-protected amino acid (1.5 g, 6.9 mmol) in CH$_2$Cl$_2$ (25 mL) at room temperature was added DIPEA (3.6 mL, 20.7 mmol), and (PyBrop) (3.4 g, 6.9 mmol) followed by MeNH$_2$ (6.9 mL, 13.8 mmol, 2.0 M in CH$_2$Cl$_2$). The resulting solution was stirred for 18 h at room temperature (until TLC analysis deemed the reaction to be complete). The resulting mixture was washed sequentially with 10% citric acid (3×20 mL), sat. aq. NaHCO$_3$ (3×20 mL), and brine (3×20 mL). The organic layer was dried (Na$_2$SO$_4$), filtered, and concentrated under reduced pressure. The crude product was purified by flash chromatography eluting with CH$_2$Cl$_2$/MeOH (40:1) to afford 1.0 g (63% yield) of a white solid.

Step B

To a round bottom flask charged with the N-protected amide (1.0 g, 4.35 mmol) from Step A above, was added 4N HCl/dioxane (10 mL). The mixture was stirred at room temperature for 2 h. The mixture was diluted with Et$_2$O (20 mL) and concentrated under reduced pressure. The crude product was treated with Et$_2$O (2×20 mL) and concentrated under reduced pressure to afford 0.72 g (~100% yield) of crude product as the HCl salt. This material was used without further purification or characterization.

Preparative Examples 126–129

Following the procedure set forth in Preparative Example 100 but using the commercially available N-protected amino acids and amines indicated, the amine hydrochloride products in the Table below were obtained.

| Prep Ex. | Amino acid | Amine | Product | Yield (%) |
|---|---|---|---|---|
| 126 | Boc-Val-OH | (R)-α-methylbenzylamine | dipeptide product | 68% |
| 127 | Boc-Val-OH | (S)-α-methylbenzylamine | dipeptide product | 68% |
| 129 | Boc-Val-OH | α-ethylbenzylamine | dipeptide product | 97% |

Preparative Example 146

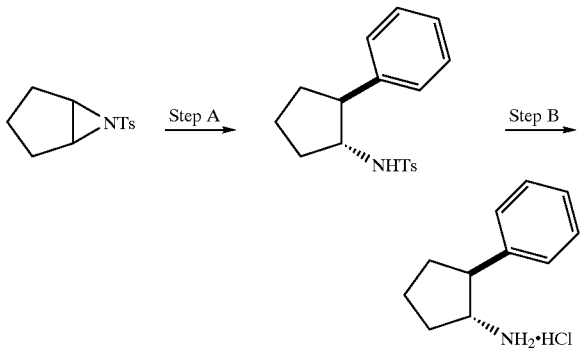

Step A

To a solution of tosylaziridine [*J. Am. Chem. Soc.* 1998, 120, 6844–6845] (0.5 g, 2.1 mmol) and Cu(acac)$_2$ (55 mg, 0.21 mmol) in THF (5 mL) at 0° C. was added PhMgBr (3.5 ml, 3.0 M in THF) diluted with THF (8 mL) dropwise over 20 min. The resulting solution was allowed to gradually warm to rt and was stirred for 12 h. Sat. aq. NH$_4$Cl (5 mL), was added and the mixture was extracted with Et$_2$O (3×15 mL). The organic layers were combined, washed with brine (1×10 mL), dried (MgSO$_4$) and concentrated under reduced pressure. The crude residue was purified by preparative TLC eluting with hexane/EtOAc (4:1) to afford 0.57 g (86% yield) of a white solid. The purified tosylamine was taken on directly to the next step.

Step B

To a solution of tosylamine (0.55 g, 1.75 mmol) in NH$_3$ (20 mL) at −78° C. was added sodium (0.40 g, 17.4 mmol). The resulting solution was stirred at −78° C. for 2 h whereupon the mixture was treated with solid NH$_4$Cl and allowed to warm to rt. Once the NH$_3$ had boiled off, the mixture was partitioned between water (10 mL) and CH$_2$Cl$_2$ (10 mL). The layers were separated and the aqueous layer was extracted with CH$_2$Cl$_2$ (2×10 mL). The organic layers were combined,), dried (NaSO$_4$), and concentrated under reduced pressure to a volume of ~20 mL. 4N HCl in dioxane (5 mL) was added and the mixture was stirred for 5 min. The mixture was concentrated under reduced pressure and the resultant crude residue was recrystallized from EtOH/Et$_2$O to afford 0.30 g (87% yield) of a white solid.

Preparative Examples 147–150

Following the procedure set forth in Preparative Example 146 but using the requisite tosylaziridines and Grignard reagents listed in the Table below, the following amine hydrochloride products were obtained.

| Prep Ex. | Tosyl aziridine | Grignard Reagent | Amine hydrochloride | 1. Yield (%) |
|---|---|---|---|---|
| 147 | ⟨aziridine-NTs⟩ | MeMgBr | ⟨cyclopentyl-Me, NH$_2$·HCl⟩ | 1. 19% |
| 148 | ⟨aziridine-NTs⟩ | EtMgBr | ⟨cyclopentyl-Et, NH$_2$·HCl⟩ | 1. 56% |
| 149 | ⟨aziridine-NTs⟩ | n-PrMgBr | ⟨cyclopentyl-nPr, NH$_2$·HCl⟩ | 1. 70% |

-continued

| Prep Ex. | Tosyl aziridine | Grignard Reagent | Amine hydrochloride | 1. Yield (%) |
|---|---|---|---|---|
| 150 | ⟨aziridine-NTs⟩ | i-PrMgCl | ⟨cyclopentyl-iPr, NH$_2$·HCl⟩ | 1. 41% |

Preparative Example 200

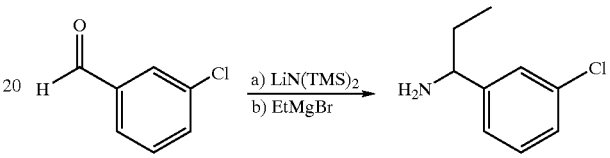

To a solution of 3-chlorobenzaldehyde (2.0 g, 14.2 mmol) in THF (5 mL) at 0° C. was added LiN(TMS)$_2$ (17.0 ml, 1.0 M in THF) dropwise and the resulting solution was stirred for 20 min. EtMgBr (6.0 mL, 3.0 M in Et$_2$O) was added dropwise and the mixture was refluxed for 24 h. The mixture was cooled to room temperature, poured into sat. aq. NH$_4$Cl (50 mL), and then extracted with CH$_2$Cl$_2$ (3×50 volumes). The organic layers were combined and concentrated under reduced pressure. The crude residue was stirred with 3 M HCl (25 mL) for 30 min, the aqueous layer was then extracted with CH$_2$Cl$_2$ (3×15 mL) and the organic layers were discarded. The aqueous layer was cooled to 0° C. and treated with solid NaOH pellets until pH=10 was obtained. The aqueous layer was extracted with CH$_2$Cl$_2$ (3×15 mL) and the organic layers were combined. The organic layer was washed with brine (1×25 mL), dried (Na$_2$SO$_4$), and concentrated under reduced pressure to afford 1.6 g (66% yield) of the crude amine as a yellow oil (MH$^+$170). This material was determined to be >90% pure and was used without further purification.

Preparative Examples 207–213

Following the procedure set forth in Preparative Example 200 but using the commercially available aldehydes and Grignard indicatied below, the amine products listed in the Table below were obtained.

| Prep Ex. | Aldehyde | Grignard Reagent | Amine Product | 1. Yield (%) 2. MH$^+$ |
|---|---|---|---|---|
| 207 | ⟨3-F-benzaldehyde⟩ | EtMgBr | ⟨1-(3-F-phenyl)propylamine⟩ | 1. 73% 2. 154 |

-continued

| Prep Ex. | Aldehyde | Grignard Reagent | Amine Product | 1. Yield (%) 2. MH+ |
|---|---|---|---|---|
| 209 | 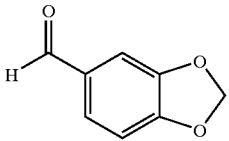 | EtMgBr | 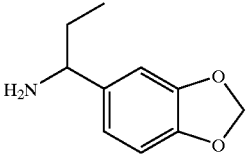 | 1. 55% 2. 180 |
| 211 | 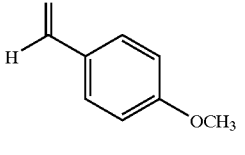 | EtMgBr | 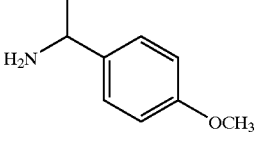 | 1. 80% 2. 166 |
| 213 | 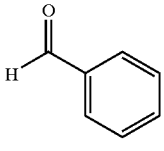 | i-PrMgBr | 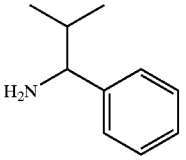 | 1. 20% 2. 150 |

Preparative Example 250

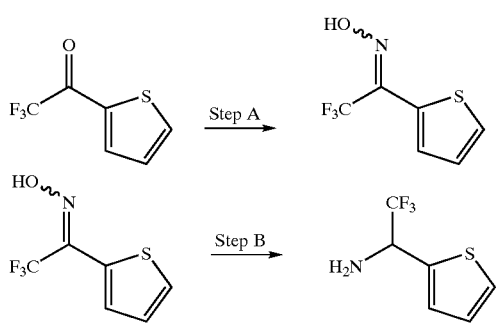

Step A

A mixture of 2-(trifluoroacetyl)thiophene (2 mL, 15.6 mmol), hydroxylamine hydrochloride (2.2 g, 2 eq), Diisopropylethylamine (5.5 mL, 2 eq) and MeOH (50 mL) was stirred at reflux for 48–72 hrs, then concentrated in vacuo. The residue was diluted with EtOAc, washed with 10% $KH_2PO_4$ and dried over $Na_2SO_4$ (anhydrous). Filtration and concentration afforded the desired oxime (2.9 g, 96%) which was used directly in Step B without further purification.

Step B

To a mixture of the product from Step A above in TFA (20 mL) was added Zn powder (3 g, 3 eq) portionwise over 30 min. The mixture was stirred at room temperature overnight. The solid was filtered and the mixture reduced under vacuo. Aqueous NaOH (2 M) was added and the mixture was extracted several times with $CH_2Cl_2$. The organic phase was dried over anhydrous $Na_2SO_4$, filtered and concentrated to afford the title compound (1.4 g, 50%).

Preparative Examples 255–259

Following the procedure set forth in Preparative Example 250 but using the commercially available ketones indicated below, the amine products listed in the table below were obtained.

| Prep Example | Ketone | Amine Product | 1. Yield (%) 2. MH+ |
|---|---|---|---|
| 255 | 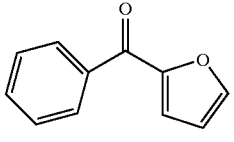 | 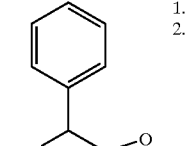 | 1. 47% 2. 174 |
| 256 | 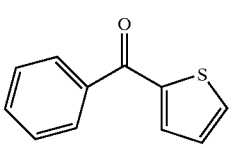 | 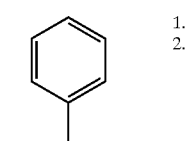 | 1. 71% 2. 190 |
| 257 | 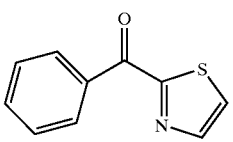 | 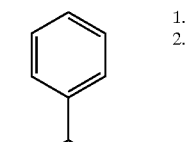 | 1. 78% 2. 191 |

-continued

| Prep Example | Ketone | Amine Product | 1. Yield (%) 2. MH+ |
|---|---|---|---|
| 258 | | | 1. 80% 2. 190 |
| 259 | | | 1. 9% 2. 156 |

Preparative Example 270

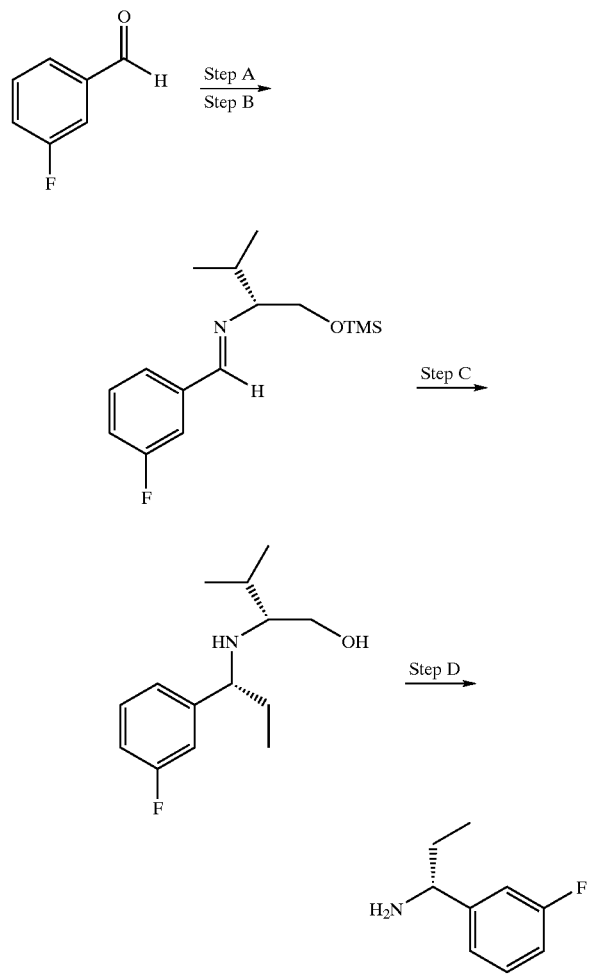

Step A

To a solution of (D)-valinol (4.16 g, 40.3 mmol) in CH$_2$Cl$_2$ (60 mL) at 0° C. was added MgSO$_4$ (20 g) followed by dropwise addition of 3-fluorobenzaldehyde (5.0 g, 40.3 mmol). The heterogenous solution was stirred at 0° C. for 2 h, was allowed to warm to room temperature and was stirred overnight (14 h). The mixture was filtered and the drying agent was washed with CH$_2$Cl$_2$ (2×10 mL). The filtrate was concentrated under reduced pressure to afford 8.4 g (100%) of a colorless oil which was taken onto the next step without further purification.

Step B

To a solution of the imine (8.4 g, 40.2 mmol) from Step A in CH$_2$Cl$_2$ (60 mL) at room temperature was added Et$_3$N (6.2 mL, 44.5 mmol) followed by dropwise addition of TMSCl (5.7 mL, 44.5 mmol). The mixture was stirred for 6 h at room temperature whereupon the precipitate that had formed was filtered off and washed with CH$_2$Cl$_2$ (2×10 mL). The combined filtrate was concentrated under reduced pressure and was taken up in Et$_2$O/hexane (1:1/150 mL). The precipitate was filtered off and the filtrate was concentrated under reduced pressure to afford 10.1 g (89%) of the protected imine as a red oil. This material was taken onto the next step without further purification.

Step C

To a solution of EtI (4.0 g, 25.6 mmol) in Et$_2$O (40 mL) at −78° C. was added t-BuLi (30.1 mL, 51.2 mmol, 1.7 M in pentane) and the mixture was stirred for 10 min. The mixture was warmed to room temperature, stirred for 1 h, and was recooled to −40° C. A solution of the imine (6.0 g, 21.4 mmol) from Step B in Et$_2$O (30 mL) was added dropwise via addition funnel to afford a bright orange mixture. The reaction mixture was stirred for 1.5 h at −40° C. whereupon 3M HCl (50 mL) was added and the mixture was allowed to warm to room temperature. Water (50 mL) was added and the layers were separated. The aqueous layer was extracted with Et$_2$O (2×30 mL) and the organic layers were combined and discarded. The aqueous layer was cooled to 0° C. and carefully treated with solid NaOH pellets until pH=12 was obtained. The aqueous layer was extracted with Et$_2$O (3×30 mL) and the combined layers were washed with brine (1×30 mL). The organic layer was dried (Na$_2$SO$_4$), filtered, and concentrated under reduced pressure to afford 4.8 g (94% yield) of the amine as a red oil. This material was taken on crude to the next step without further purification.

Step D

To a solution of amine (4.5 g, 18.8 mmol) from Step C in MeOH (80 mL) at room temperature was added MeNH$_2$ (25 mL, 40% in water) followed by the addition of a solution of H$_5$IO$_6$ (14.0 g, 61.4 mmol) in H$_2$O (25 mL). The heterogenous mixture was stirred for 1.5 h (until the reaction was complete by TLC) and the precipitate was filtered off. The resulting filtrate was diluted with water (50 mL) and the mixture was extracted with Et$_2$O (4×60 mL). The combined organic layers were concentrated to a volume of ~30 mL whereupon 3M HCl (75 mL) was added. The mixture was stirred overnight (12 h at room temperature) whereupon the mixture was concentrated to remove the volatiles. The aqueous layer was extracted with Et$_2$O (3×40 mL) and the organic layers were discarded. The aqueous layer was cooled to 0° C. and was carefully treated with solid NaOH pellets until pH ~12 was reached. The aqueous layer was extracted with Et$_2$O (3×60 mL) and the combined organic layers were dried (MgSO$_4$). The organic layer was concentrated under reduced pressure to afford 2.8 g (97% yield) of the desired amine as a yellow oil [MH+154]. This compound was proven to be >85% pure by $^1$H NMR and was used without further purification.

Preparative Examples 273–280

Following the procedure set forth in Preparative Example 270 but using the commercially available aldehydes, amino alcohols, and organolithium reagents indicated below, the optically pure amine products in the Table below were obtained.

| Prep Ex. | Aldehyde | Amino Alcohol | Organo lithium | Product | 1. Yield (%) 2. MH+ |
|---|---|---|---|---|---|
| 273 | 4-F-C6H4-CHO | (S)-tert-leucinol | cyclopropyl-Li | (R)-1-(4-fluorophenyl)-1-cyclopropylmethylamine | 1. 54% 2. 166 |
| 276 | 2-thiophene-CHO | (S)-tert-leucinol | EtLi | (R)-1-(2-thienyl)propylamine | 1. 42% 2. 142 |
| 278 | PhCHO | (S)-tert-leucinol | cyclopropyl-Li | (R)-1-phenyl-1-cyclopropylmethylamine | 1. 62% 2. 148 |
| 279 | 2-thiophene-CHO | (S)-tert-leucinol | t-BuLi | (R)-1-(2-thienyl)-2,2-dimethylpropylamine | 1. 27% 2. 256 |
| 280 | PhCHO | (S)-tert-leucinol | t-BuLi | (R)-1-phenyl-2,2-dimethylpropylamine | 1. 15% 2. 164 |
| 280.1 | 5-methyl-2-furyl-CHO | (S)-tert-leucinol | EtLi | (R)-1-(5-methyl-2-furyl)propylamine | 1. 29% 2. 126 |
| 280.2 | 5-methyl-2-furyl-CHO | (S)-tert-leucinol | EtLi | (R)-1-(5-methyl-2-furyl)propylamine | 1. 35% 2. 126 |

Preparative Example 282

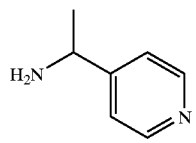

The title compound was prepared according to methods previously bed: J. Med. Chem. 1996, 39, 3319–3323.

Preparative Example 284

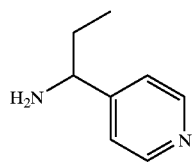

The title compound was prepared according to methods previously described: J. Med. Chem. 1996, 39, 3319–3323.

Preparative Example 286

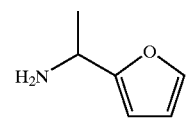

The title compound was prepared according to methods previously described: Chem. Pharm. Bull. 1991, 39, 181–183.

Preparative Example 288

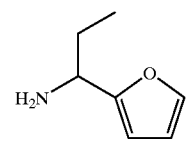

The title compound was prepared according to methods previously described: Chem. Pharm. Bull. 1991, 39, 181–183.

Preparative Example 290

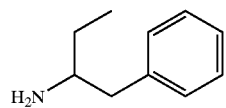

The title compound was prepared according to methods previously described: J. Med. Chem. 1988, 31, 2176–2186.

Preparative Example 292

The title compound was prepared according to methods previously described: J. Org. Chem. 1978, 43, 892–898.

Preparative Example 300

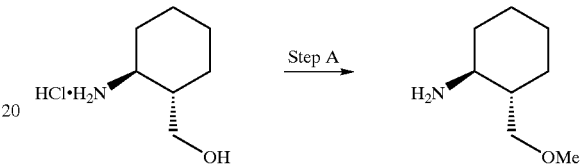

Step A

To a solution of KH (0.45 g, 11.3 mmol) in THF (15 mL) at room temperature was added amine hydrochloride (0.85 g, 5.1 mmol) portionwise to afford a heterogenous reaction mixture. The mixture was allowed to stand overnight (12 h) and then a solution of MeI (0.32 mL, 5.1 mmol) was added dropwise. The mixture was stirred for 6 h whereupon the mixture was carefully poured into cold brine (125 mL). The mixture was extracted with $Et_2O$ (3×25 mL) and the organic layers were combined. The organic layer was dried over $Na_2SO_4$, filtered, and concentrated under reduced pressure to afford the crude product as a yellow oil. This material was used without further purification or characterization.

Preparative Example 320

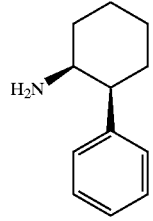

The title compound was prepared according to methods previously described: J. Org. Chem. 1987, 52, 4437–4444.

Preparative Example 325

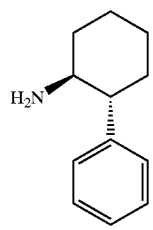

The title compound was prepared according to methods previously described: Bull. Chem. Soc. Jpn. 1962, 35, 11–16.

EXAMPLE 500

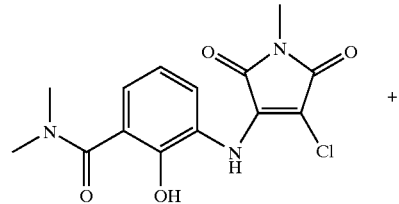

+

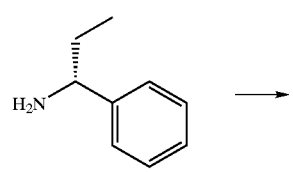 →

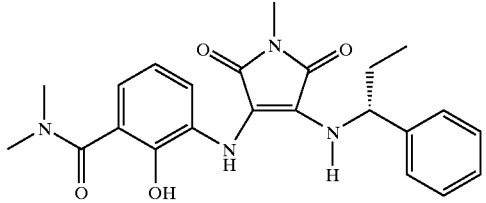

If one were to follow the procedure set forth in Pol. J. Chem. 1991, 65, 889–897 or the procedure set forth in J. Organomet. Chem. 1994, 482, 85–92 using the chloro intermediate from Preparative Examples 67 and the benzyl amine shown, then one would obtain the title compound.

EXAMPLES 501–697

If one were to follow the procedure set forth in Example 500 using the prepared (as indicated) or commercially available amines below and the chloro intermediates from the Preparative Examples indicated, the Product listed in the table below would be obtained.

| Ex. # | Amine (Prep Ex. #) | Cl Inter. (Prep Ex. #) | Product |
|---|---|---|---|
| 501 | 3) | 51 | ![product 501] |
| 502 | -thiophene) | 51 | ![product 502] |
| 503 | -furan) | 51 | ![product 503] |
| 504 | | 51 | ![product 504] |

-continued

| Ex. # | Amine (Prep Ex. #) | Cl Inter. (Prep Ex. #) | Product |
|---|---|---|---|
| 505 | cyclohexylamine | 51 | (structure) |
| 506 | cyclopentylamine | 51 | (structure) |
| 507 | 2,2,2-trifluoro-1-(thiophen-2-yl)ethanamine | 51 | (structure) |
| 508 | (S)-1-phenylpropan-1-amine | 55 | (structure) |
| 509 | (S)-1-phenylpropan-1-amine | 56 | (structure) |
| 510 | 1-(benzo[d][1,3]dioxol-5-yl)propan-1-amine | 51 | (structure) |
| 511 | (S)-1-phenylpropan-1-amine | 52 | (structure) |

-continued

| Ex. # | Amine (Prep Ex. #) | Cl Inter. (Prep Ex. #) | Product |
|---|---|---|---|
| 512 | | 53 | |
| 513 | | 51 | |
| 514 | | 61 | |
| 515 | | 51 | |
| 516 | | 51 | |
| 517 | | 61 | |
| 519 | | 51 | |

-continued
| Ex. # | Amine (Prep Ex. #) | Cl Inter. (Prep Ex. #) | Product |
|---|---|---|---|
| 520 | 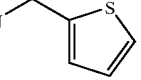 | 51 | 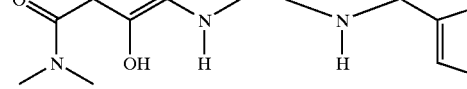 |
| 521 | 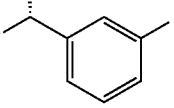 | 51 | 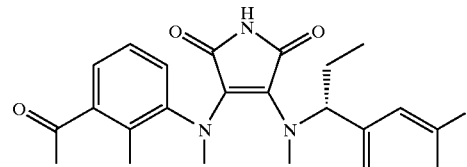 |
| 522 |  | 51 | 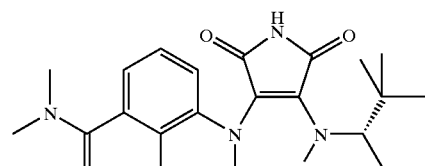 |
| 523 |  | 58 | 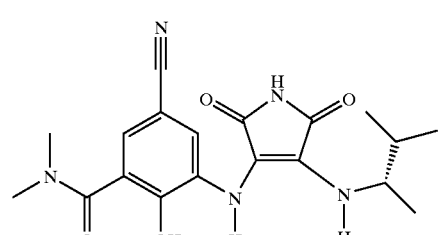 |
| 524 |  | 51 | 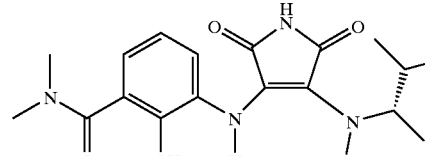 |
| 525 | 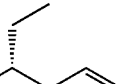 | 58 | 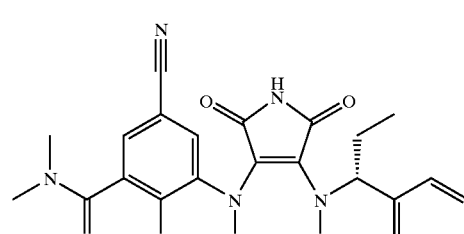 |
| 526 | 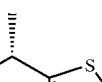 | 51 | 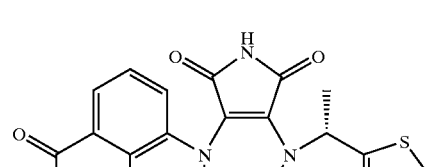 |

-continued
| Ex. # | Amine (Prep Ex. #) | Cl Inter. (Prep Ex. #) | Product |
|---|---|---|---|
| 527 | 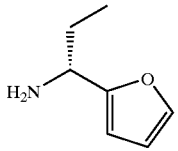 | 51 | 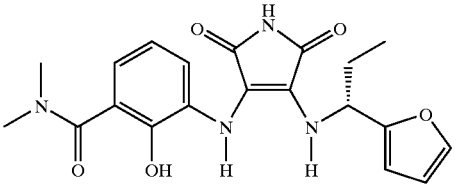 |
| 528 | 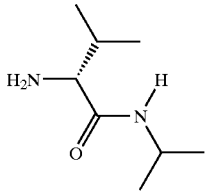 | 51 | 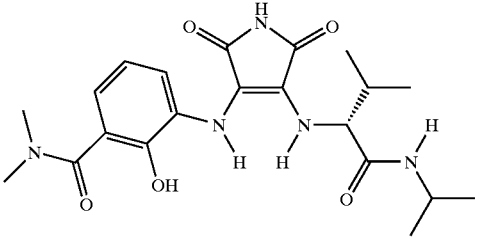 |
| 529 | 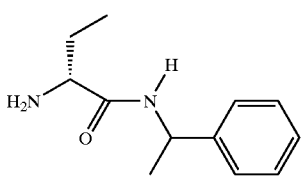 | 51 | 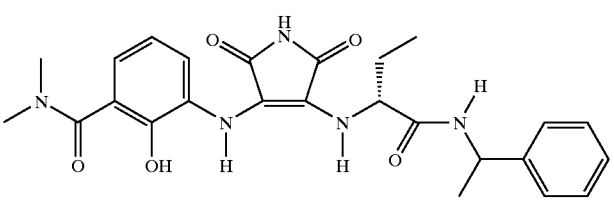 |
| 530 | 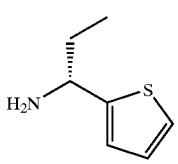 | 112 | 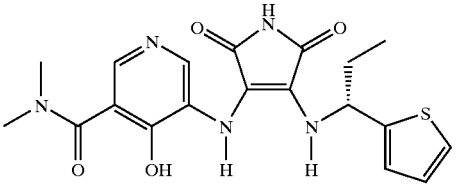 |
| 531 | 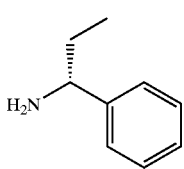 | 54 | 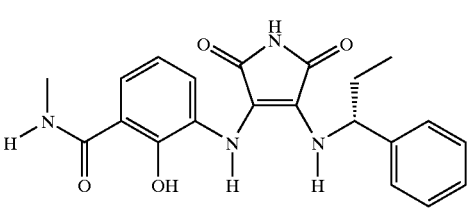 |
| 532 | 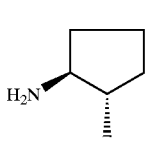 | 51 | 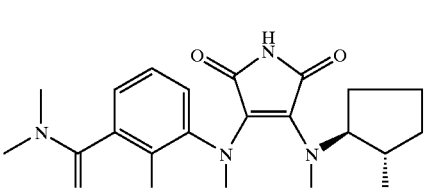 |
| 533 | 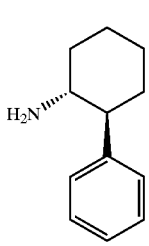 | 51 | 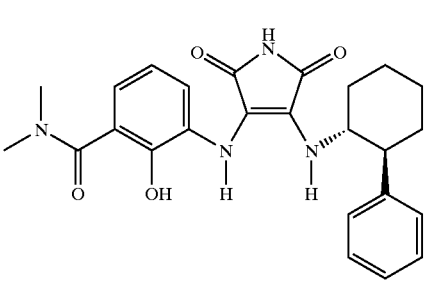 |

-continued

| Ex. # | Amine (Prep Ex. #) | Cl Inter. (Prep Ex. #) | Product |
|---|---|---|---|
| 534 | (S)-1-phenylpropylamine | 63 | |
| 535 | (S)-1-(5-methylfuran-2-yl)propylamine | 51 | |
| 535.1 | (R)-1-(5-methylfuran-2-yl)propylamine | 51 | |
| 536 | cycloheptylamine | 51 | |
| 537 | (S)-1-(thiophen-2-yl)propylamine | 59 | |
| 538 | (S)-1-phenylpropylamine | 57 | |
| 540 | (S)-2,2,2-trifluoro-1-(thiophen-2-yl)ethylamine | 51 | |

-continued
| Ex. # | Amine (Prep Ex. #) | Cl Inter. (Prep Ex. #) | Product |
|---|---|---|---|
| 541 | 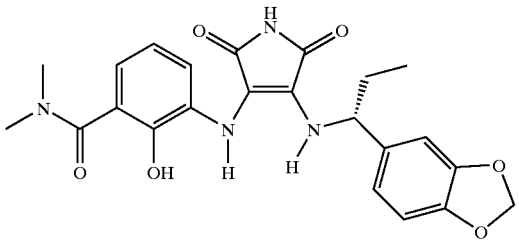 | 51 | 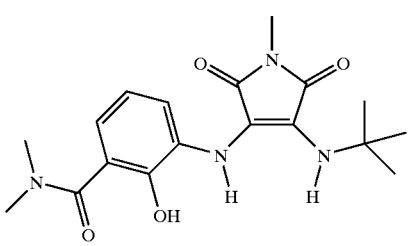 |
| 542 | 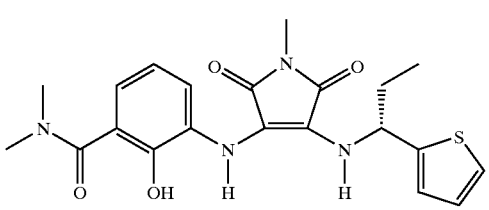 | 67 | |
| 543 | | 67 | |
| 544 | | 82 | |
| 545 | 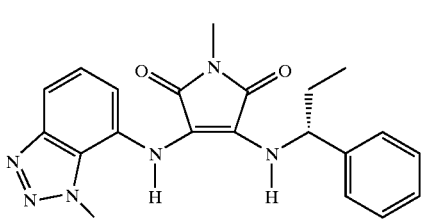 | 67 | 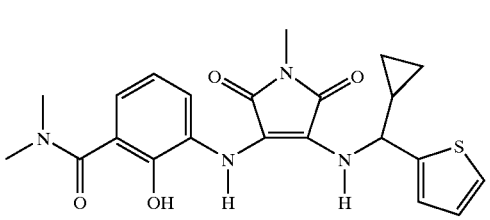 |
| 546 | | 67 | 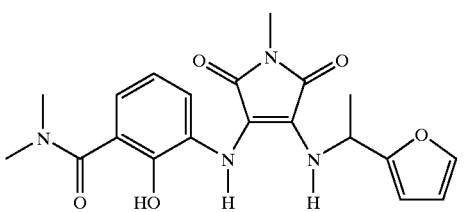 |

-continued
| Ex. # | Amine (Prep Ex. #) | Cl Inter. (Prep Ex. #) | Product |
|---|---|---|---|
| 547 | 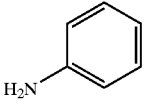 | 67 | 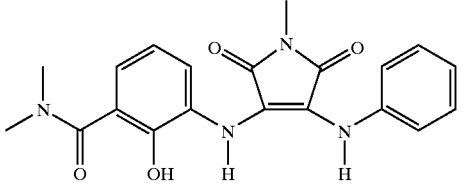 |
| 548 | 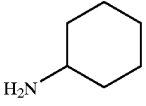 | 67 | 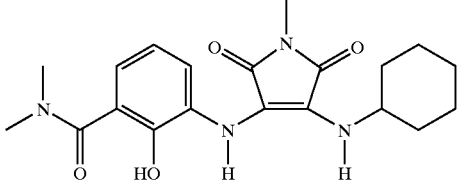 |
| 549 | 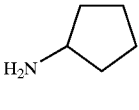 | 67 | 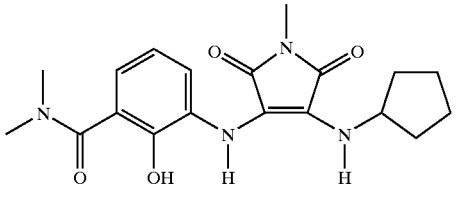 |
| 550 | 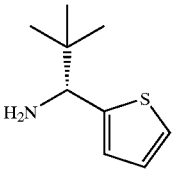 | 67 | 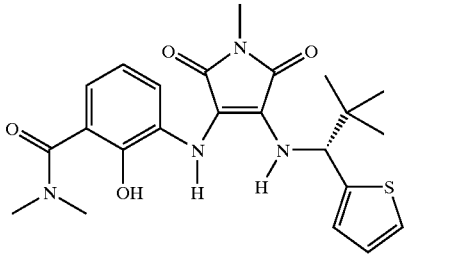 |
| 551 | 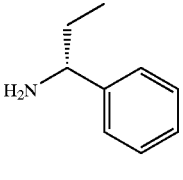 | 74 | 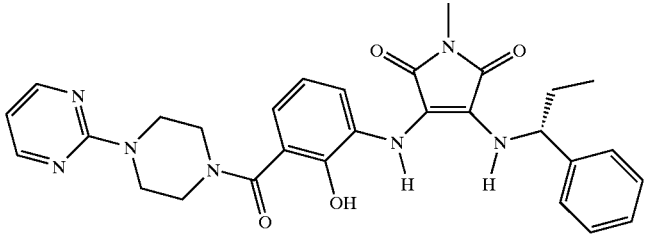 |
| 552 | 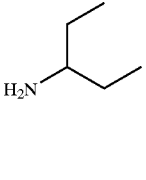 | 67 | 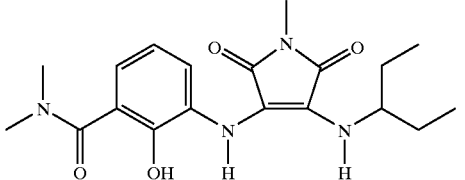 |
| 553 | 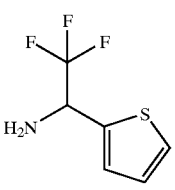 | 67 | 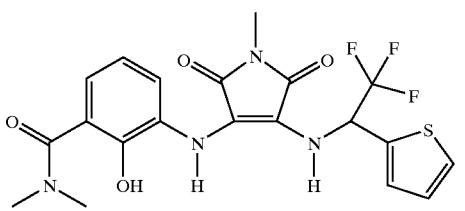 |

-continued

| Ex. # | Amine (Prep Ex. #) | Cl Inter. (Prep Ex. #) | Product |
|---|---|---|---|
| 554 | | 67 | |
| 555 | | 67 | |
| 556 | | 75 | |
| 557 | | 76 | |
| 558 | | 77 | |
| 559 | | 67 | |

-continued

| Ex. # | Amine (Prep Ex. #) | Cl Inter. (Prep Ex. #) | Product |
|---|---|---|---|
| 560 | | 68 | |
| 561 | | 69 | |
| 562 | | 67 | |
| 563 | | 70 | |
| 564 | | 67 | |
| 565 | | 71 | |

-continued
| Ex. # | Amine (Prep Ex. #) | Cl Inter. (Prep Ex. #) | Product |
|---|---|---|---|
| 566 | 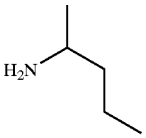 | 67 | 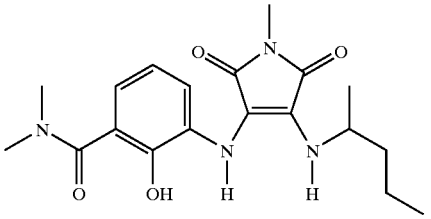 |
| 567 | 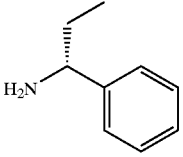 | 72 | 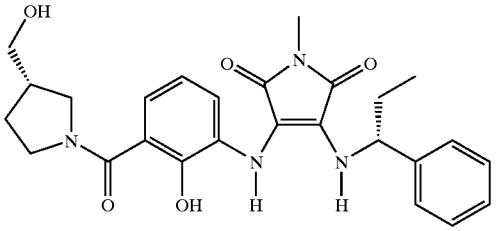 |
| 568 | 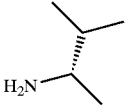 | 85 | 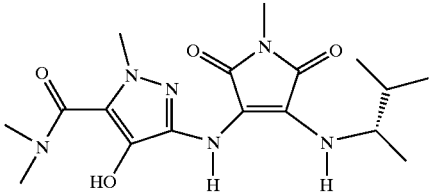 |
| 569 | 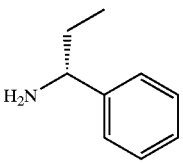 | 85 | 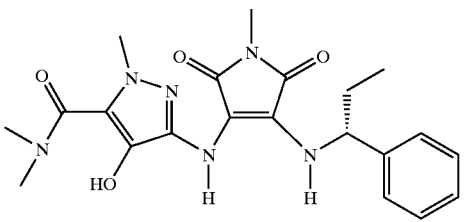 |
| 571 | 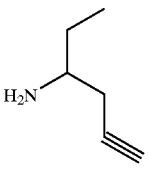 | 67 | 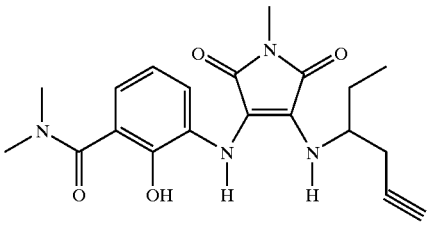 |
| 572 | 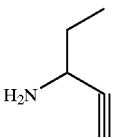 | 67 | 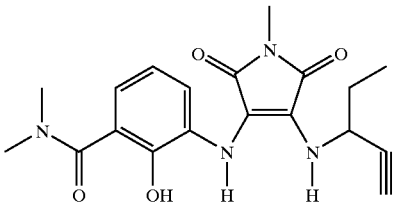 |

-continued

| Ex. # | Amine (Prep Ex. #) | Cl Inter. (Prep Ex. #) | Product |
|---|---|---|---|
| 574 | | 67 | |
| 575 | | 67 | |
| 576 | | 67 | |
| 577 | | 67 | |
| 578 | | 67 | |
| 579 | | 81 | |

-continued

| Ex. # | Amine (Prep Ex. #) | Cl Inter. (Prep Ex. #) | Product |
|---|---|---|---|
| 580 | | 81 | |
| 581 | | 67 | |
| 582 | | 67 | |
| 583 | | 67 | |
| 584 | | 67 | |
| 585 | | 80 | |

-continued

| Ex. # | Amine (Prep Ex. #) | Cl Inter. (Prep Ex. #) | Product |
|---|---|---|---|
| 586 | | 79 | |
| 587 | | 67 | |
| 588 | | 67 | |
| 589 | | 67 | |
| 590 | | 73 | |
| 591 | | 67 | |

-continued

| Ex. # | Amine (Prep Ex. #) | Cl Inter. (Prep Ex. #) | Product |
|---|---|---|---|
| 592 | | 67 | |
| 593 | | 67 | |
| 594 | | 87 | |
| 595 | | 67 | |
| 595.1 | | 67 | |
| 596 | | 67 | |

-continued

| Ex. # | Amine (Prep Ex. #) | Cl Inter. (Prep Ex. #) | Product |
|---|---|---|---|
| 597 | | 67 | |
| 598 | | 67 | |
| 599 | | 83 | |
| 600 | | 78 | |
| 602 | | 67 | |
| 603 | | 67 | |

-continued
| Ex. # | Amine (Prep Ex. #) | Cl Inter. (Prep Ex. #) | Product |
|---|---|---|---|
| 604 | 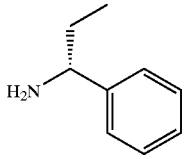 | 91 | 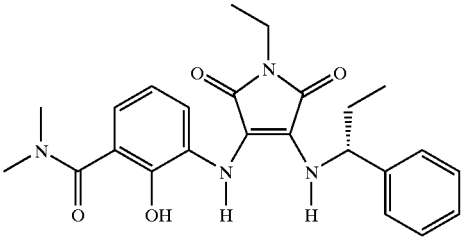 |
| 605 |  | 91 | 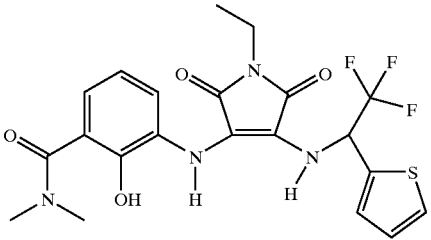 |
| 606 | 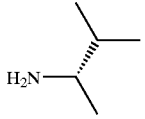 | 91 | 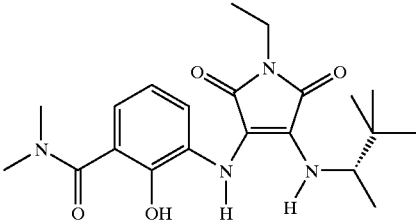 |
| 607 | 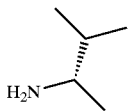 | 91 | 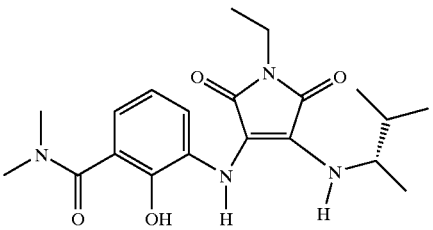 |
| 608 | 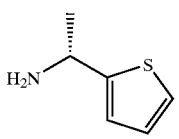 | 91 | 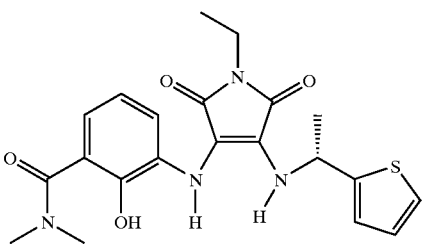 |
| 609 | 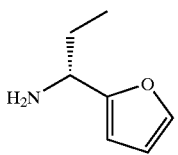 | 91 | 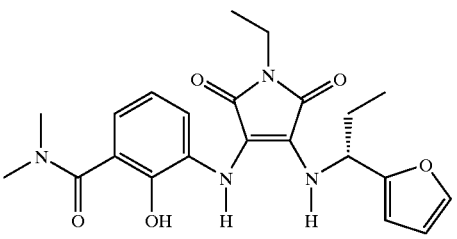 |

-continued
| Ex. # | Amine (Prep Ex. #) | Cl Inter. (Prep Ex. #) | Product |
|---|---|---|---|
| 610 | 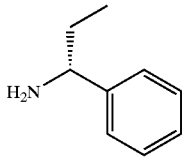 | 94 | 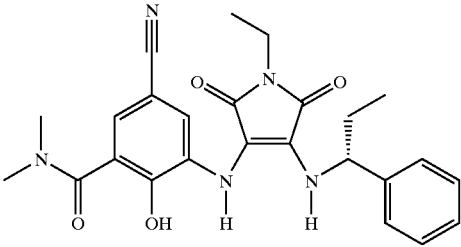 |
| 611 | 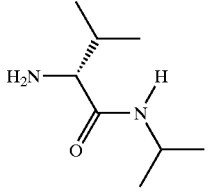 | 91 | 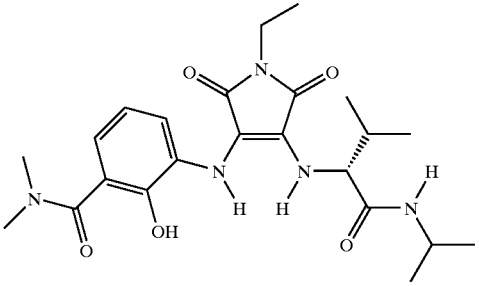 |
| 612 | 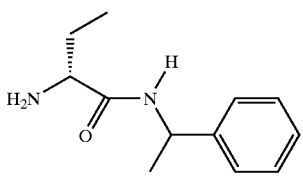 | 91 | 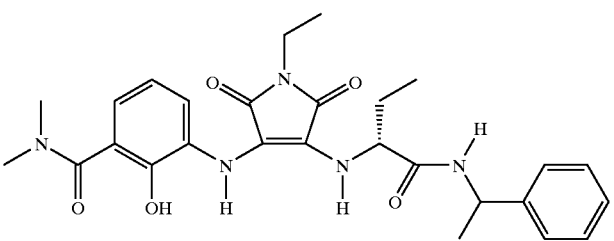 |
| 613 | 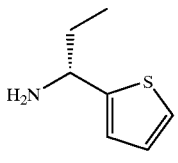 | 95 | 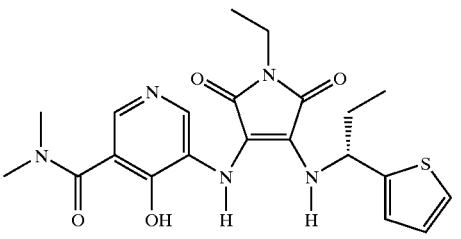 |
| 614 | 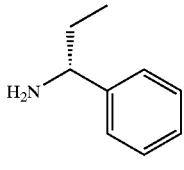 | 93 | 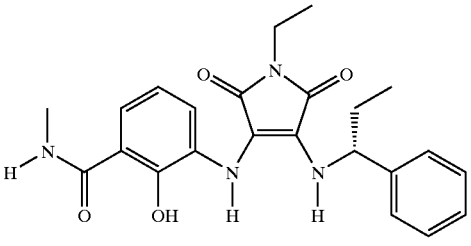 |
| 615 | 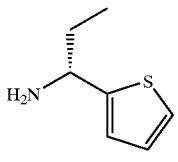 | 91 | 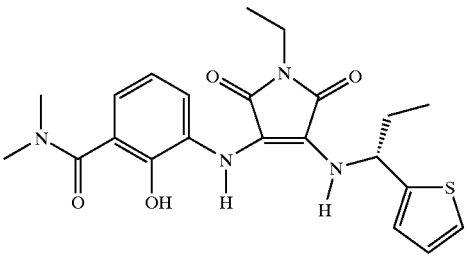 |

-continued

| Ex. # | Amine (Prep Ex. #) | Cl Inter. (Prep Ex. #) | Product |
|---|---|---|---|
| 616 | pentan-2-amine | 91 | 3-(1-ethyl-2,5-dioxo-4-(pentan-2-ylamino)-2,5-dihydro-1H-pyrrol-3-ylamino)-2-hydroxy-N,N-dimethylbenzamide |
| 617 | 1-(furan-2-yl)ethanamine | 91 | 3-(1-ethyl-4-(1-(furan-2-yl)ethylamino)-2,5-dioxo-2,5-dihydro-1H-pyrrol-3-ylamino)-2-hydroxy-N,N-dimethylbenzamide |
| 618 | (S)-1-phenylpropan-1-amine | 92 | morpholino-substituted analog |
| 619 | aniline | 91 | 3-(1-ethyl-2,5-dioxo-4-(phenylamino)-2,5-dihydro-1H-pyrrol-3-ylamino)-2-hydroxy-N,N-dimethylbenzamide |
| 620 | cyclohexanamine | 91 | 3-(4-(cyclohexylamino)-1-ethyl-2,5-dioxo-2,5-dihydro-1H-pyrrol-3-ylamino)-2-hydroxy-N,N-dimethylbenzamide |
| 621 | cyclopentanamine | 91 | 3-(4-(cyclopentylamino)-1-ethyl-2,5-dioxo-2,5-dihydro-1H-pyrrol-3-ylamino)-2-hydroxy-N,N-dimethylbenzamide |

| Ex. # | Amine (Prep Ex. #) | Cl Inter. (Prep Ex. #) | Product |
|---|---|---|---|
| 622 | (S)-2,2,2-trifluoro-1-(thiophen-2-yl)ethanamine | 91 | |
| 623 | (S)-1-(benzo[d][1,3]dioxol-5-yl)propan-1-amine | 91 | |
| 624 | (S)-1-phenylpropan-1-amine | 101 | |
| 625 | 2,2,2-trifluoro-1-(thiophen-2-yl)ethanamine | 101 | |
| 626 | (S)-3,3-dimethylbutan-2-amine | 101 | |

-continued
| Ex. # | Amine (Prep Ex. #) | Cl Inter. (Prep Ex. #) | Product |
|---|---|---|---|
| 627 | 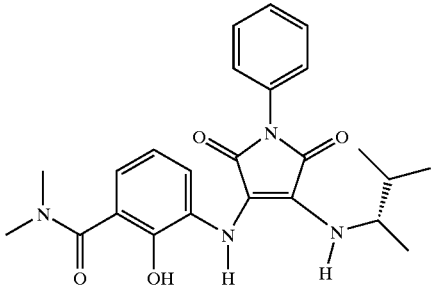 | 101 | |
| 628 | 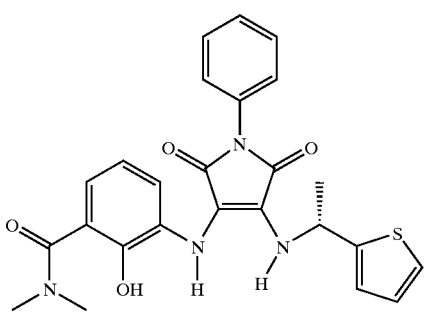 | 101 | |
| 629 | 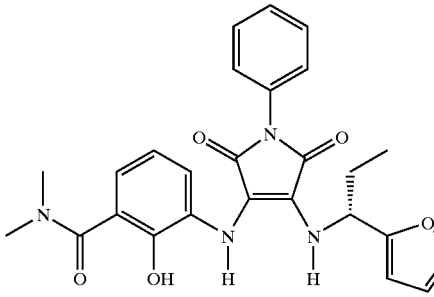 | 101 | |
| 630 | 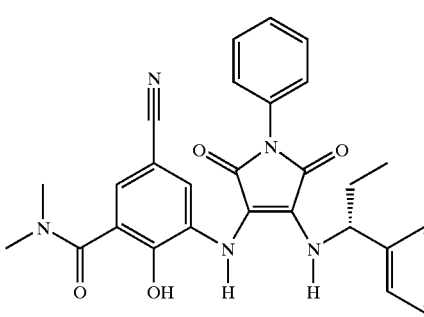 | 104 | |

-continued

| Ex. # | Amine (Prep Ex. #) | Cl Inter. (Prep Ex. #) | Product |
|---|---|---|---|
| 631 | | 101 | |
| 632 | | 101 | |
| 633 | | 105 | |
| 634 | | 103 | |
| 635 | | 101 | |

-continued

| Ex. # | Amine (Prep Ex. #) | Cl Inter. (Prep Ex. #) | Product |
|---|---|---|---|
| 636 | (sec-butylamine structure) H₂N-CH(CH₃)-CH₂-CH₂-CH₃ | 101 | (pyrrole-2,5-dione product with N-phenyl, dimethylcarbamoyl-hydroxyphenylamino, and sec-pentylamino substituents) |
| 637 | 1-(furan-2-yl)ethylamine | 101 | (pyrrole-2,5-dione product with N-phenyl, dimethylcarbamoyl-hydroxyphenylamino, and 1-(furan-2-yl)ethylamino substituents) |
| 638 | (S)-1-phenylpropylamine | 102 | (pyrrole-2,5-dione product with N-phenyl, morpholinocarbonyl-hydroxyphenylamino, and (S)-1-phenylpropylamino substituents) |
| 639 | aniline | 101 | (pyrrole-2,5-dione product with N-phenyl, dimethylcarbamoyl-hydroxyphenylamino, and phenylamino substituents) |
| 640 | cyclohexylamine | 101 | (pyrrole-2,5-dione product with N-phenyl, dimethylcarbamoyl-hydroxyphenylamino, and cyclohexylamino substituents) |

-continued

| Ex. # | Amine (Prep Ex. #) | Cl Inter. (Prep Ex. #) | Product |
|---|---|---|---|
| 641 | cyclopentylamine | 101 | |
| 642 | (S)-2,2,2-trifluoro-1-(thiophen-2-yl)ethan-1-amine | 101 | |
| 643 | (S)-1-(benzo[d][1,3]dioxol-5-yl)propan-1-amine | 101 | |
| 644 | (S)-1-phenylpropan-1-amine | 106 | |

-continued

| Ex. # | Amine (Prep Ex. #) | Cl Inter. (Prep Ex. #) | Product |
|---|---|---|---|
| 645 | (structure) | 106 | (structure) |
| 646 | (structure) | 106 | (structure) |
| 647 | (structure) | 106 | (structure) |
| 648 | (structure) | 106 | (structure) |
| 649 | (structure) | 106 | (structure) |

-continued
| Ex. # | Amine (Prep Ex. #) | Cl Inter. (Prep Ex. #) | Product |
|---|---|---|---|
| 650 | 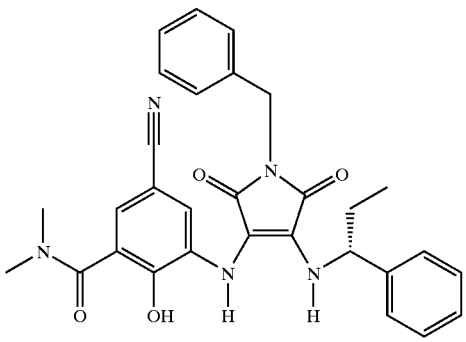 | 109 | |
| 651 | 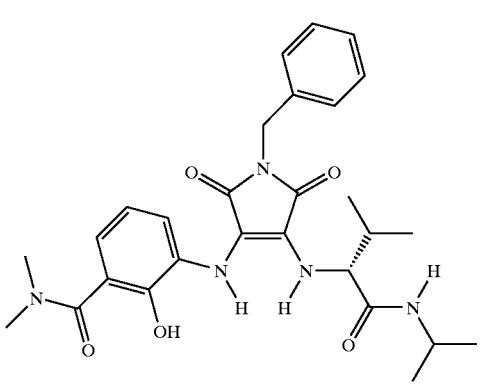 | 106 | |
| 652 | 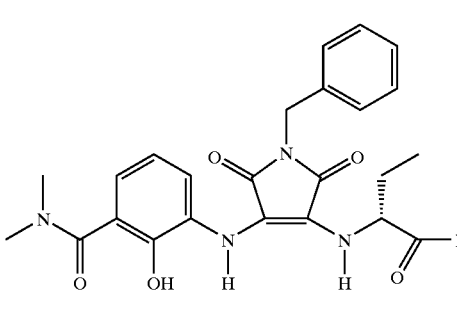 | 106 | |
| 653 | 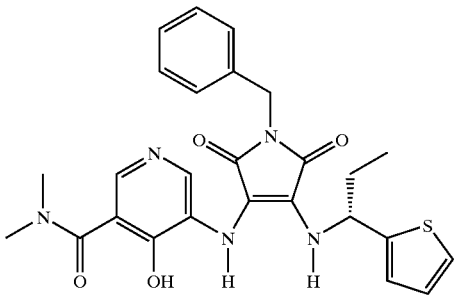 | 110 | |

-continued
| Ex. # | Amine (Prep Ex. #) | Cl Inter. (Prep Ex. #) | Product |
|---|---|---|---|
| 654 | 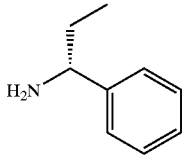 | 108 | 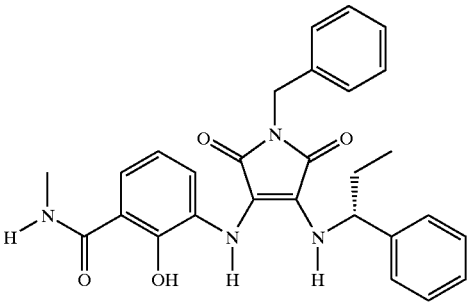 |
| 655 | 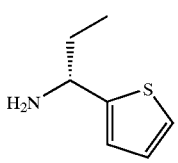 | 106 | 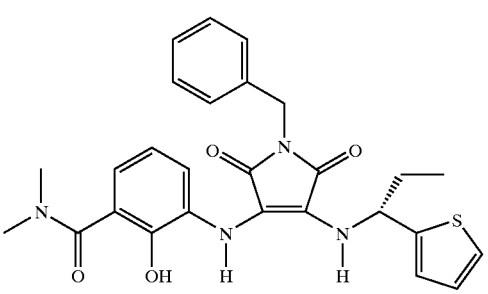 |
| 656 | 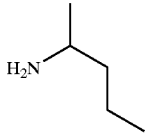 | 106 | 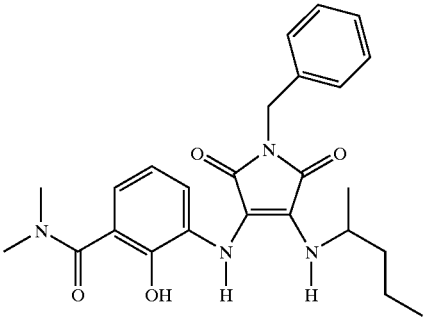 |
| 657 | 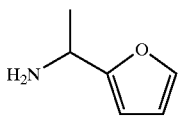 | 106 | 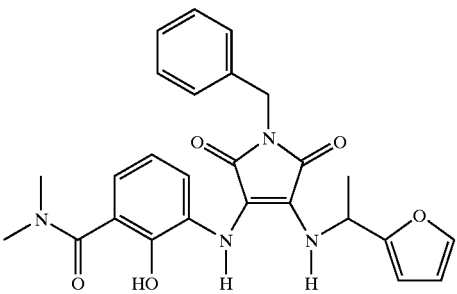 |
| 658 | 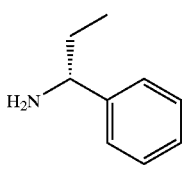 | 107 | 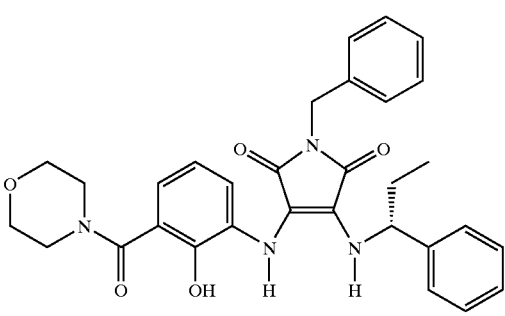 |

-continued

| Ex. # | Amine (Prep Ex. #) | Cl Inter. (Prep Ex. #) | Product |
|---|---|---|---|
| 659 | aniline | 106 | |
| 660 | cyclohexylamine | 106 | |
| 661 | cyclopentylamine | 106 | |
| 662 | (S)-2,2,2-trifluoro-1-(thiophen-2-yl)ethanamine | 106 | |

-continued
| Ex. # | Amine (Prep Ex. #) | Cl Inter. (Prep Ex. #) | Product |
|---|---|---|---|
| 663 | 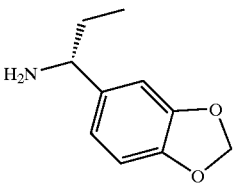 | 106 | 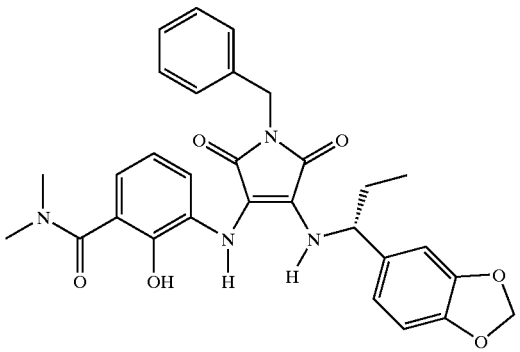 |
| 664 | 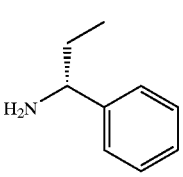 | 96 | 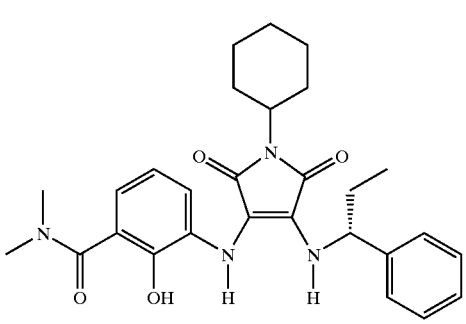 |
| 665 | 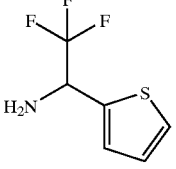 | 96 | 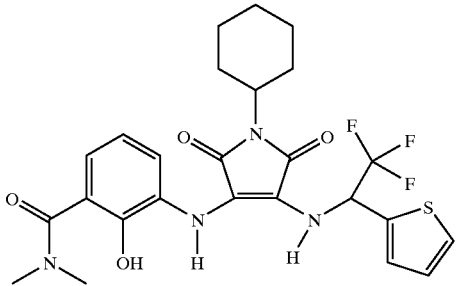 |
| 667 | 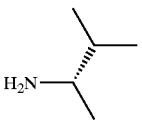 | 96 | 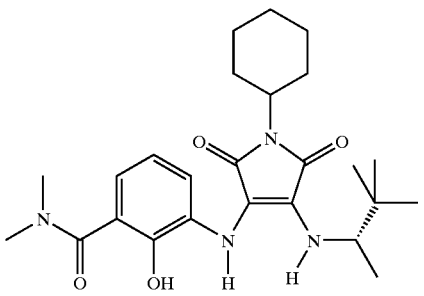 |
| 668 | 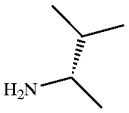 | 96 | 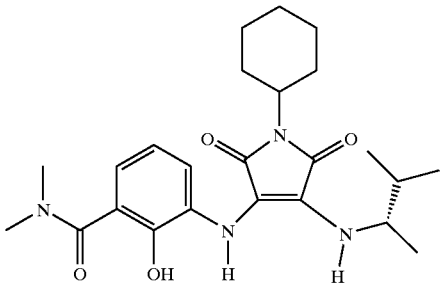 |

-continued

| Ex. # | Amine (Prep Ex. #) | Cl Inter. (Prep Ex. #) | Product |
|---|---|---|---|
| 669 | (S)-1-(thiophen-2-yl)ethylamine | 96 | |
| 670 | (S)-1-(furan-2-yl)propylamine | 96 | |
| 671 | (S)-1-phenylpropylamine | 99 | |
| 672 | (S)-2-amino-N-isopropyl-3-methylbutanamide | 96 | |

| Ex. # | Amine (Prep Ex. #) | Cl Inter. (Prep Ex. #) | Product |
|---|---|---|---|
| 673 | 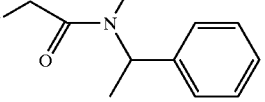 | 96 | 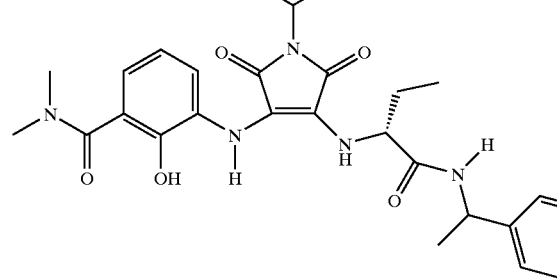 |
| 674 | 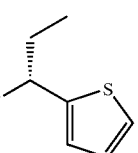 | 100 | 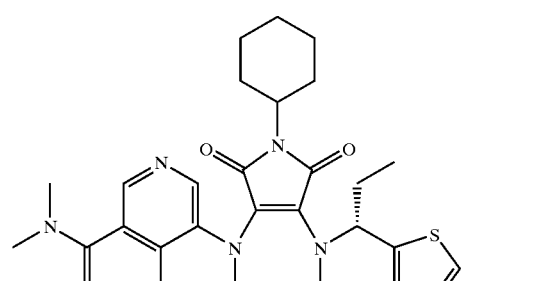 |
| 675 | 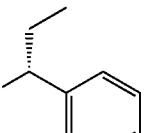 | 98 | 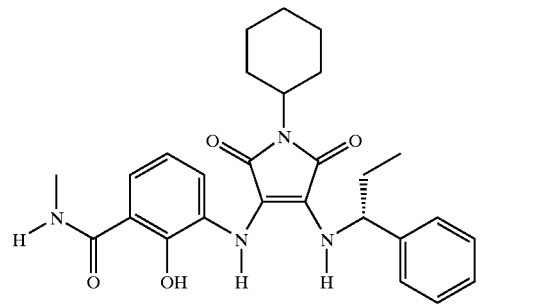 |
| 676 | 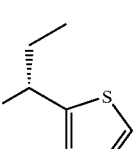 | 96 | 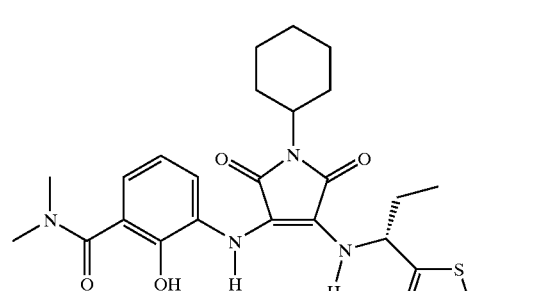 |

-continued

| Ex. # | Amine (Prep Ex. #) | Cl Inter. (Prep Ex. #) | Product |
|---|---|---|---|
| 677 | (sec-pentylamine) | 96 | |
| 678 | 1-(furan-2-yl)ethylamine | 96 | |
| 679 | (S)-1-phenylpropylamine | 97 | |
| 680 | aniline | 96 | |
| 681 | cyclohexylamine | 96 | |

-continued
| Ex. # | Amine (Prep Ex. #) | Cl Inter. (Prep Ex. #) | Product |
|---|---|---|---|
| 682 | 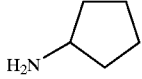 | 96 | 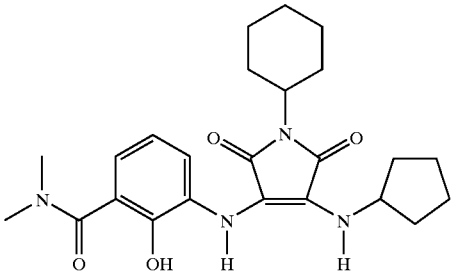 |
| 683 | 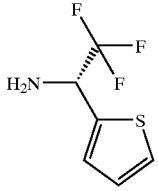 | 96 | 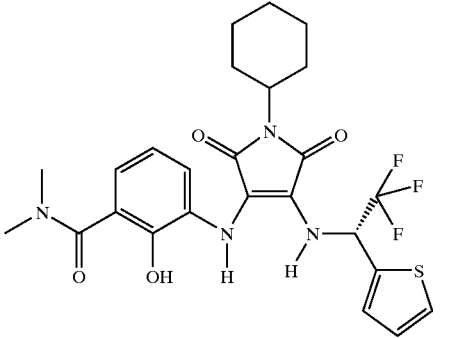 |
| 684 | 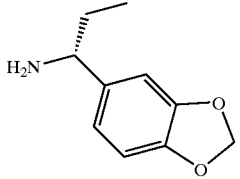 | 96 | 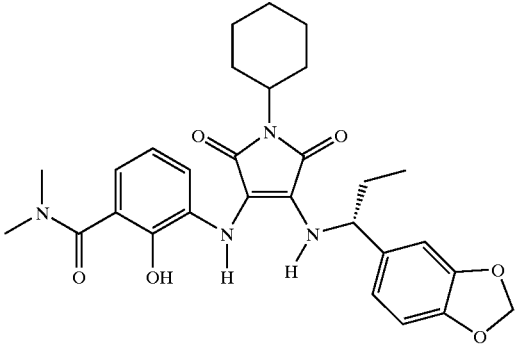 |
| 685 | 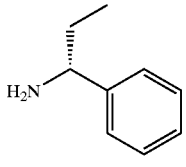 | 64 | 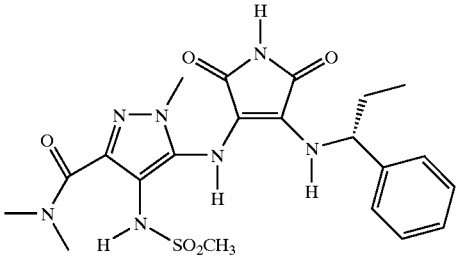 |
| 687 | 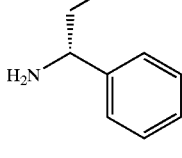 | 65 | 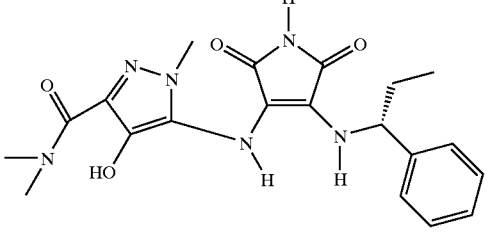 |

| Ex. # | Amine (Prep Ex. #) | Cl Inter. (Prep Ex. #) | Product |
|---|---|---|---|
| 688 | 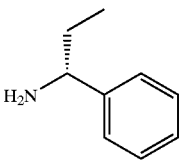 | 66 | 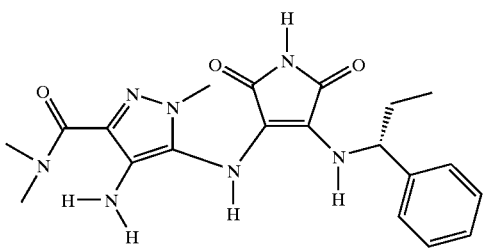 |
| 689 | 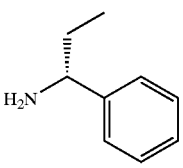 | 88 | 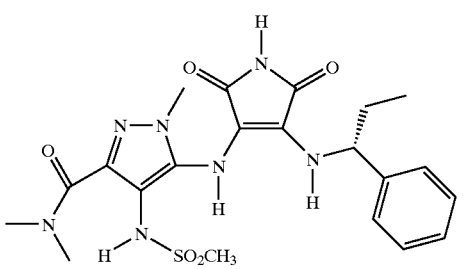 |
| 690 | 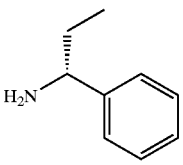 | 89 | 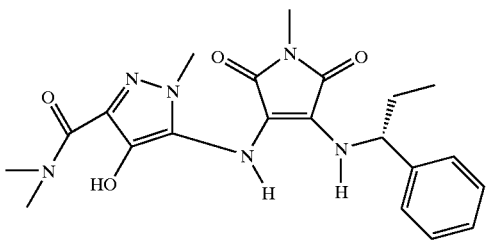 |
| 691 | 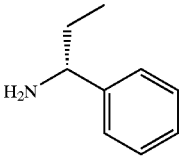 | 90 | 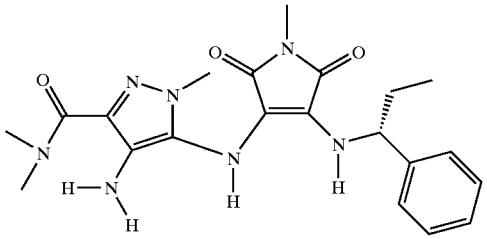 |
| 692 | 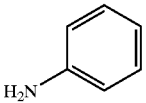 | 111 | 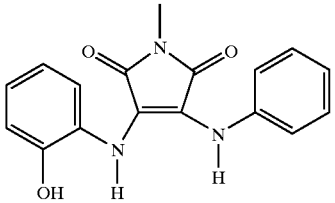 |
| 693 | 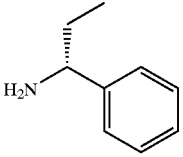 | 111 | 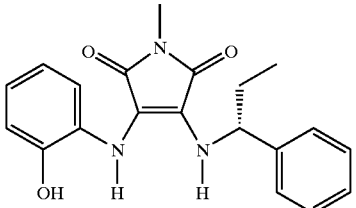 |

| Ex. # | Amine (Prep Ex. #) | Cl Inter. (Prep Ex. #) | Product |
|---|---|---|---|
| 694 | | 111 | |
| 695 | | 111 | |
| 696 | | 111 | |
| 697 | | 111 | |

Preparative Example 400

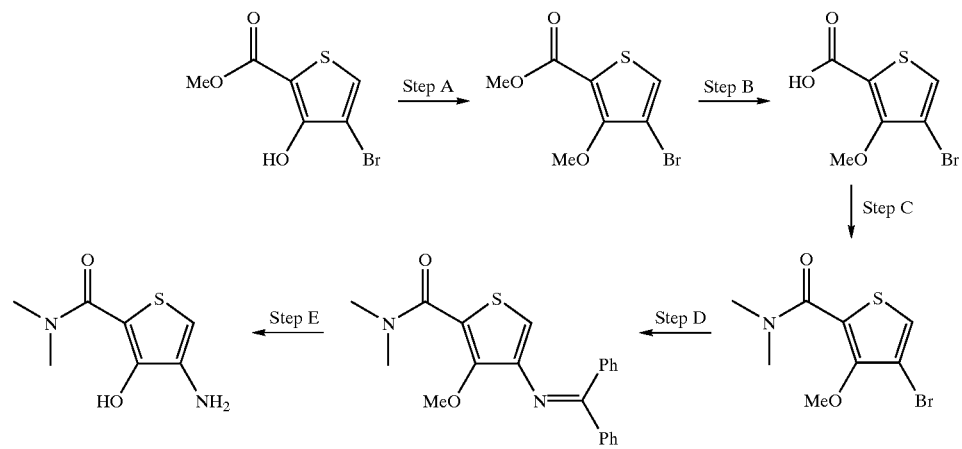

Step A

Methyl-3-hydroxy-4-bromo-2-thiophenecarboxylate (10.0 g, 42.2 mmol) was dissolved in 250 mL of acetone. Potassium carbonate (30.0 g, 217.4 mmol) was added followed by a solution of iodomethane (14.5 mL, 233.0 mmol). The mixture was heated to reflux and continued for 6 h. After cooled to room temperature, the mixture was filtered, the solid material was rinsed with acetone (~200 mL). The filtrate and rinsing were concentrated under reduced pressure to a solid, further dried on high vacuum, yielding 13.7 g (100%) of methyl-3-methoxy-4-bromo-2-thiophenecarboxylate (MH$^+$=251.0).

Step B

Methyl-3-methoxy-4-bromo-2-thiophenecarboxylate (13.7 g), available from step A, was dissolved in 75 mL of THF, and added with a 1.0 M sodium hydroxide aqueous solution (65 mL, 65.0 mmol). The mixture was stirred at room temperature for 24 h. A 1.0 M hydrogen chloride aqueous solution was added dropwise to the mixture until pH was approximately 2. The acidic mixture was extracted with CH$_2$Cl$_2$ (100 mL×2, 50 mL). The combined organic extracts were washed with brine (40 mL), dried with Na$_2$SO$_4$, and concentrated under reduced pressure to a solid, 10.0 g (100%, over two steps) of 3-methoxy-4-bromo-2-thiophenecarboxylic acid (MH$^+$=237.0).

Step C

To a stirred solution of 3-methoxy-4-bromo-2-thiophenecarboxylic acid (6.5 g, 27.4 mmol) in 140 mL of CH$_2$Cl$_2$, obtained from step B, was added bromo-tripyrrolidinophosphonium hexafluorophosphate (PyBrop, 12.8 g, 27.5 mmol), a 2.0 M solution of dimethyl amine in THF (34.5 mL, 69.0 mmol), and diisopropylethyl amine (12.0 mL, 68.7 mmol). After 3 d, the mixture was diluted with 100 mL of CH$_2$Cl$_2$, and washed with a 1.0 M sodium hydroxide aqueous solution (30 mL×3) and brine (30 mL). The organic solution was dried with Na$_2$SO$_4$, filtered, and concentrated to an oil. This crude oil product was purified by flash column chromatography, eluting with CH$_2$Cl$_2$-hexanes (1:1, v/v). Removal of solvents afforded a solid, further dried on high vacuum, yielding 6.76 g (93%) of N, N'-dimethyl-3-methoxy-4-bromo-2-thiophenecarboxamide (MH$^+$=265.0, M+2=266.1).

Step D

An oven dried three-neck round bottom flask was equipped with a refluxing condenser, charged sequentially with palladium acetate (95 mg, 0.42 mmol), (R)-BINAP (353 mg, 0.57 mmol), cesium carbonate (9.2 g, 28.33 mmol), and N, N'-dimethyl-3-methoxy-4-bromo-2-thiophenecarboxamide (3.74 g, 14.2 mmol, from Step C). The solid mixture was flushed with nitrogen. Toluene (95 mL) was added to the solid mixture followed by benzophenone imine (3.6 mL, 21.5 mmol). The mixture was heated to reflux and continued for 10 h. A second batch of palladium acetate (95 mg, 0.42 mmol) and (R)-BINAP (353 mg, 0.57 mmol) in 5 mL of toluene was added. Refluxing was continued for 14 h. The third batch of palladium acetate (30 mg, 0.13 mmol) and (R)-BINAP (88 mg, 0.14 mmol) was added, and reaction continued at 110° C. for 24 h. The mixture was cooled to room temperature, diluted with ether (50 mL), filtered through a layer of Celite, rinsing with ether. The filtrate and rinsing were concentrated under reduced pressure to an oil, which was purified twice by flash column chromatography using CH$_2$Cl$_2$ and CH$_2$Cl$_2$-MeOH (200:1) as eluents. Removal of solvents afforded 4.1 g (79%) of the amido-thiophene diphenylimine product as a solid (MH$^+$=365.1).

Step E

To a stirred solution of thiophene imine (5.09 g, 13.97 mmol), obtained from step D, in 140 mL of CH$_2$Cl$_2$ at −78° C. was added dropwise a 1.0 M solution of boron tribromide in CH$_2$Cl$_2$. The mixture was stirred for 3 h while the temperature of the cooling bath was increased slowly from −78° C. to −15° C. 100 mL of H$_2$O was added, the mixture was stirred at room temperature for 30 min, then the two layers were separated. The organic layer (as A) was extracted with H$_2$O (30 mL×2). The aqueous layer and aqueous extracts were combined, washed with CH$_2$Cl$_2$ (30 mL), and adjusted to pH ~8 using a saturated NaHCO$_3$ aqueous solution. The neutralized aqueous solution was extracted with CH$_2$Cl$_2$ (100 mL×3), the extracts were washed with brine, dried with Na$_2$SO$_4$, and concentrated under reduced pressure to a light yellow solid, 1.49 g of N, N'-dimethyl-3-hydroxy-4-amino-2-thiophenecarboxamide (first crop). The previous separated organic layer A and organic washing were combined, stirred with 30 mL of a 1.0 M HCl aqueous solution for 1 h. The two layers were separated, the aqueous layer was washed with CH$_2$Cl$_2$ (30 mL) and adjusted to pH ~8 using a saturated NaHCO$_3$ aqueous solution, and the separated organic layer and organic washing were combined as organic layer B. The neutralized aqueous solution was extracted with CH$_2$Cl$_2$ (30 mL×4), the extracts were washed with brine, dried by Na$_2$SO$_4$, and concentrated under reduced pressure to give 0.48 g of a solid as the second crop of the titled product. Organic layer B from above was washed with brine, and concentrated to an oil, which was separated by preparative TLC (CH$_2$Cl$_2$-MeOH=50:1) to afford 0.45 g of a solid as the third crop of the titled product. The overall yield of the product, N, N'-dimethyl-3-hydroxy-4-amino-2-thiophenecarboxamide, is 2.32 g (89%) (MH$^+$=187.0).

Preparative Example 401

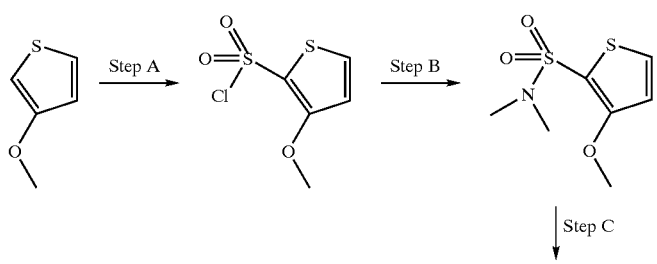

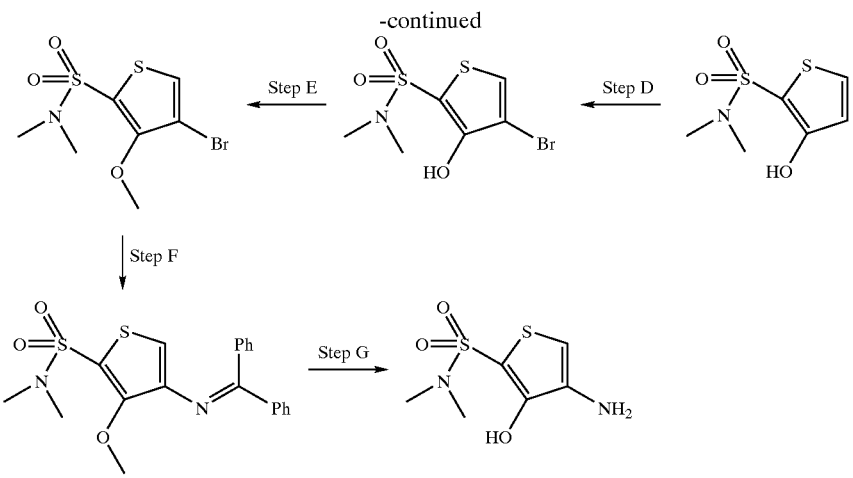

Step A

To a solution of 3-methoxythiophene (3 g) in dichloromethane (175 mL) at −78° C. was added chlorosulfonic acid (8.5 mL) dropwise. The mixture was stirred for 15 min at −78° C. and 1.5 h at room temp. Afterwards, the mixture was poured carefully into crushed ice, and extracted with dichloromethane. The extracts were washed with brine, dried over magnesium sulfate, filtered through a 1-in silica gel pad. The filtrate was concentrated in vacuo to give the desired compound (4.2 g).

Step B

The product from Step A above (4.5 g) was dissolved in dichloromethane (140 mL) and added with triethylamine (8.8 mL) followed by diethyl amine in THF (2M, 21 mL). The resulting mixture was stirred at room temperature overnight. The 15 mixture was washed with brine and saturated bicarbonate (aq) and brine again, dried over sodium sulfate, filtered through a 1-in silica gel pad. The filtrate was concentrated in vacuo to give the desired compound (4.4 g).

Step C

The product from Step B above (4.3 g) was dissolved in dichloromethane (125 mL) and cooled in a −78° C. bath. A solution of boron tribromide (1.0 M in dichloromethane, 24.3 mL) was added. The mixture was stirred for 4 h while the temperature was increased slowly from −78° C. to 10° C. $H_2O$ was added, the two layers were separated, and the aqueous layer was extracted with dichloro-methane. The combined organic layer and extracts were washed with brine, dried over magnesium sulfate, filtered, and concentrated in vacuo to give 3.96 g of the desired hydroxy-compound.

Step D

The product from step C above (3.96 g) was dissolved in 125 mL of dichloromethane, and added with potassium carbonate (6.6 g) followed by bromine (2 mL). The mixture was stirred for 5 h at room temperature, quenched with 100 mL of $H_2O$. The aqueous mixture was addjusted to pH ~5 using a 0.5N hydrogen chloride aqueous solution, and extracted with dichloromethane. The extracts were washed with a 10% $Na_2S_2O_3$ aqueous solution and brine, dried over sodium sulfate, and filtered through a celite pad. The filtrate was concentrated in vacuo to afford 4.2 g of the desired bromo-compound.

Step E

The product from Step D (4.2 g) was dissolved in 100 mL of acetone and added with potassium carbonate (10 g) followed by iodomethane (9 mL). The mixture was heated to reflux and continued for 3.5 h. After cooled to room temperature, the mixture was filtered through a Celite pad. The filtrate was concentrated in vacuo to a dark brown residue, which was purified by flash column chromatography eluting with dichloromethane-hexanes (1:1, v/v) to give 2.7 g of the desired product.

Step F

The product from step E (2.7 g) was converted to the desired imine compound (3 g), following the similar procedure to that of Preparative Example 400 step D.

Step G

The imine product from step F (3 g) was dissolved in 80 mL of dichloromethane and cooled in a −78° C. bath. A solution of boron tribromide (1.0 M in dichloromethane, 9.2 mL) was added dropwise. The mixture was stirred for 4.25 h from −78° C. to 5° C. $H_2O$ (50 mL) was added, and the layers were separated. The aqueous layer was extracted with dichloromethane. The organic layer and extracts were combined, washed with brine, and concentrated to an oily residue. The residue was dissolved in 80 mL of methanol, stirred with sodium acetate (1.5 g) and hydroxyamine hydrochloride (0.95 g) at room temperature for 2 h. The mixture was poured into an aqueous mixture of sodium hydroxide (1.0 M aq, 50 mL) and ether (100 mL). The two layers were separated. The aqueous layer was washed with ether three times. The combined ether washings were re-extracted with $H_2O$ once. The aqueous layers were combined, washed once with dichloromethane, adjusted to pH ~6 using 3.0 M and 0.5 M hydrogen chloride aqueous solutions, and extracted with dichloromethane. The organic extracts were combined, washed with brine, dried over sodium sulfate, and concentrated in vacuo to give 1.2 g of desired amine compound.

Preparative Examples 402–405

Following the procedures set forth in Example 401, but using commercially available amines, hydroxy-aminothiophene products in the Table below were obtained.

| Prep Ex. | Amine | Product | Yield | MH+ |
|---|---|---|---|---|
| 402 | (Bn)₂NH | | 10% | 375.1 |
| 403 | Me(Bn)NH | | 14% | 299.0 |
| 404 | Et(Bn)NH | | 22% | |
| 405 | (Et)₂NH | | 25% | |

Preparative Example 406

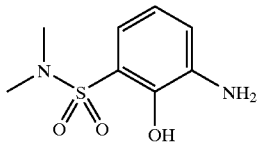

The amine was prepared following the procedure disclosed in WO 01/68570.

Preparative Example 407

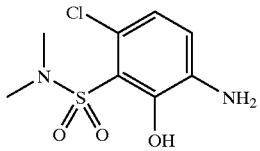

The amine was prepared following the procedure disclosed in WO 01/68570.

Preparative Example 408

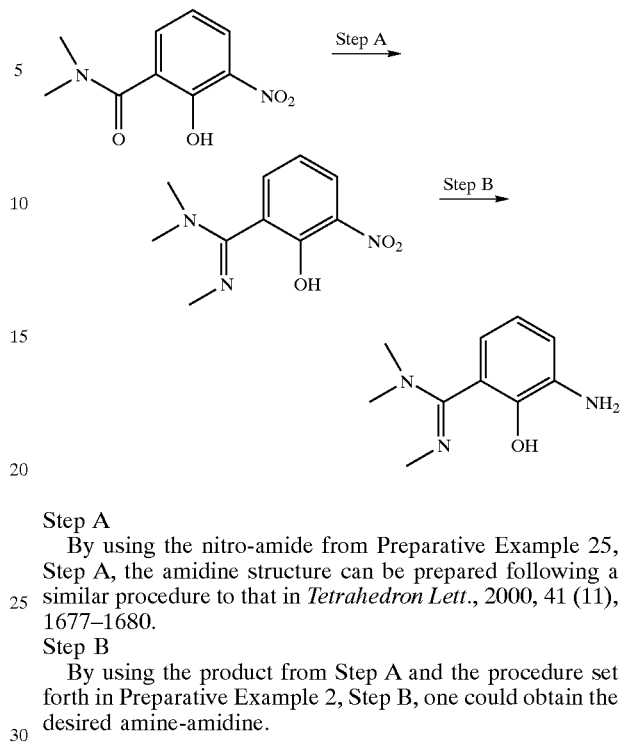

Step A
By using the nitro-amide from Preparative Example 25, Step A, the amidine structure can be prepared following a similar procedure to that in *Tetrahedron Lett.*, 2000, 41 (11), 1677–1680.

Step B
By using the product from Step A and the procedure set forth in Preparative Example 2, Step B, one could obtain the desired amine-amidine.

Alternate Preparative Example 409

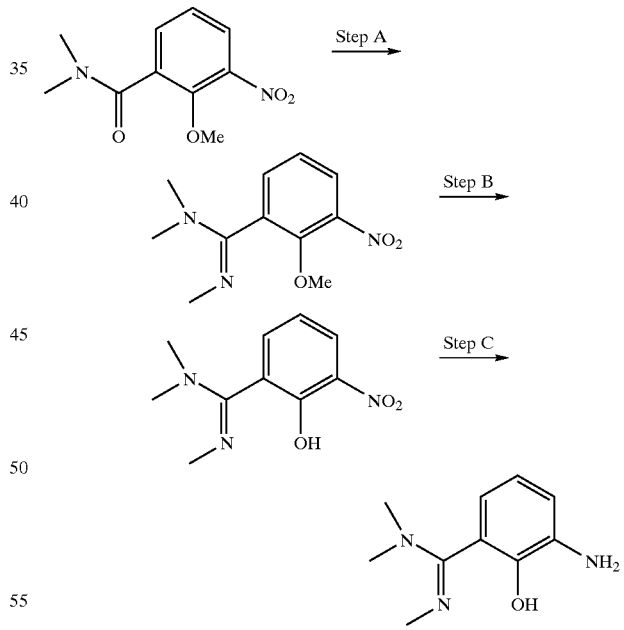

Step A
By treating the nitro-amide from Preparative Example 25, Step A with NaH and MeI in refluxing THF, and subsequently, following removal of THF by distillation, with POCl₃ followed by MeNH₂, according to procedures known in the art, one would obtain the desired compound.

Step B
By treating the product from Step A with BBr₃ in dichloromethane, according to a similar procedure set forth in the literature, one could obtain the desired compound.

Step C

By using the product from Step B and the procedure set forth in Preparative Example 2 Step B, one would obtain the desired compound.

Preparative Example 410

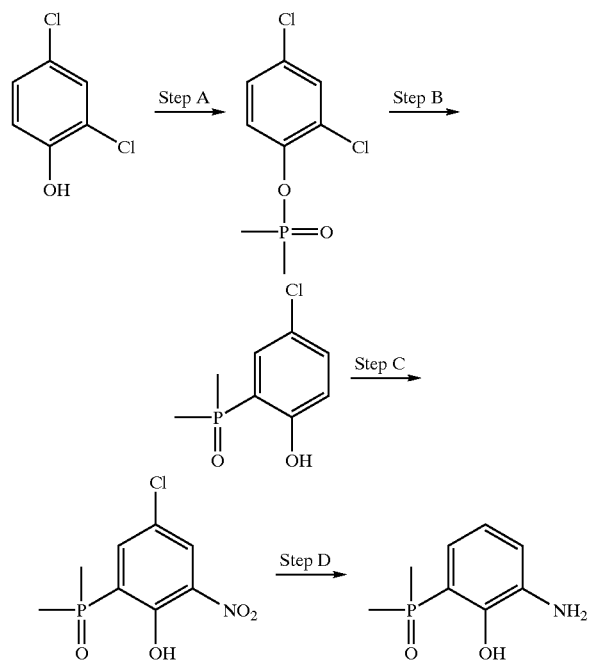

Step A

By following a similar procedure as that described in *Zh. Obshch. Khim.*, 27, 1957, 754, 757., but instead using 2,4-dichlorophenol and dimethylphosphinic chloride, one would obtain the desired compound.

Step B

By following a similar procedure as that described in *J. Organomet. Chem.*; 317, 1986, 11–22, one would obtain the desired compound.

Step C

By following a similar procedure as that described in *J. Amer. Chem. Soc.*, 77, 1955, 6221, one would obtain the desired compound.

Step D

By following a similar procedure as that described in *J. Med. Chem.*, 27, 1984, 654–659, one would obtain the desired compound.

Alternate Preparative Example 411

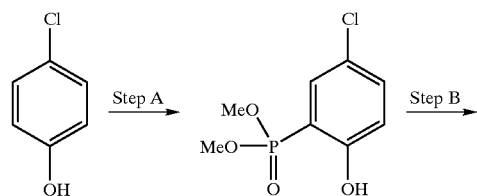

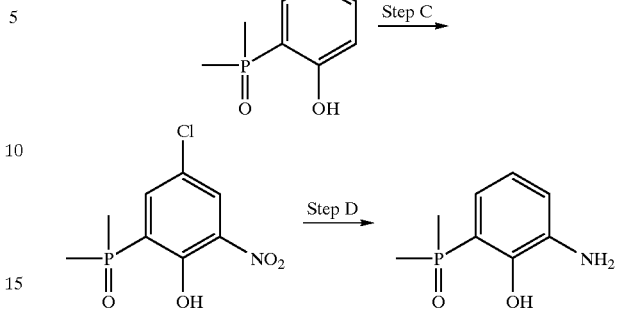

Step A

By following a similar procedure as that described in *Phosphorous, Sulfur Silicon Relat. Elem.*; EN; 61, 12, 1991, 119–129, but instead using 4-chlorophenol, one would obtain the desired compound.

Step B

By using a similar procedure as that in *Phosphorous, Sulfur Silicon Relat. Elem.*; EN; 61, 12, 1991, 119–129, but instead using MeMgBr, the desired compound could be prepared.

Step C

By following a similar procedure as that described in *J. Amer. Chem. Soc.*, 77,1955, 6221, one would obtain the desired compound.

Step D

By following a similar procedure as that described in *J. Med. Chem.*, 27, 1984, 654–659, one would obtain the desired compound.

Preparative Examples 412

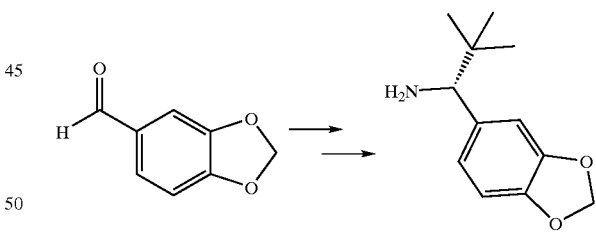

Following a similar procedure set forth in Preparative Example 270 but using the commercially available aldehyde shown above in Step A and only tert-butyllithium in Step C, the optically pure amine product was obtained (65%).

EXAMPLES 702–741

If one were to follow the procedure set forth in Preparative Example 50 using the Amine (B—NH2) and the Dichloride from the Preparative Example indicated, and subsequently treat with the Amine (A-NH2) according to the procedure used in Example 500, one would obtain the Product indicated in the Table below.

| Ex. | Amine (1) (B—NH₂) (2) (A—NH₂) | Prep Ex of Dichloride | Product |
|---|---|---|---|
| 702 | (1) 3-amino-2-hydroxy-N,N-dimethylbenzamide (2) (S)-1-(benzo[d][1,3]dioxol-5-yl)-2,2-dimethylpropan-1-amine | 40 | corresponding pyrrole-2,5-dione product |
| 703 | (1) 3-amino-2-hydroxy-N,N-dimethylbenzamide (2) (S)-1-(benzo[d][1,3]dioxol-5-yl)-2,2-dimethylpropan-1-amine | 41 | corresponding N-methyl pyrrole-2,5-dione product |
| 704 | (1) 3-amino-2-hydroxy-N,N-dimethylbenzamide (2) (S)-1-(benzo[d][1,3]dioxol-5-yl)-2,2-dimethylpropan-1-amine | 43 | corresponding N-benzyl pyrrole-2,5-dione product |

-continued

| Ex. | Amine<br>(1) (B—NH₂)<br>(2) (A—NH₂) | Prep Ex of Dichloride | Product |
|---|---|---|---|
| 705 | (1) [structure: 3-amino-2-hydroxy-N,N-dimethylbenzamide]<br>(2) [structure: (S)-1-(benzo[d][1,3]dioxol-5-yl)-2,2-dimethylpropan-1-amine] | 42 | [product structure] |
| 706 | (1) [structure: 3-amino-2-hydroxy-N,N-dimethylbenzenesulfonamide]<br>(2) [structure: (S)-1-(benzo[d][1,3]dioxol-5-yl)-2,2-dimethylpropan-1-amine] | 43 | [product structure] |
| 707 | (1) [structure: 3-amino-2-hydroxy-N,N-dimethylbenzenesulfonamide]<br>(2) [structure: (S)-1-(benzo[d][1,3]dioxol-5-yl)-2,2-dimethylpropan-1-amine] | 41 | [product structure] |

-continued
| Ex. | Amine<br>(1) (B—NH₂)<br>(2) (A—NH₂) | Prep Ex of Dichloride | Product |
|---|---|---|---|
| 708 | (1) 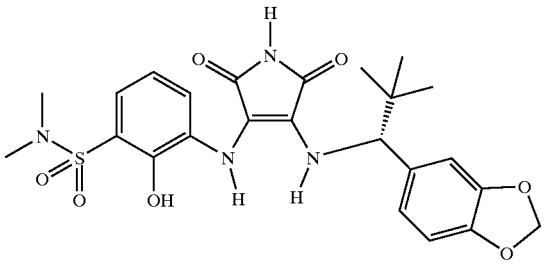 (2) 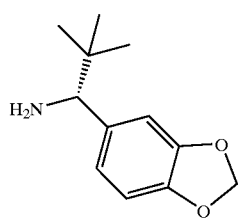 | 40 | 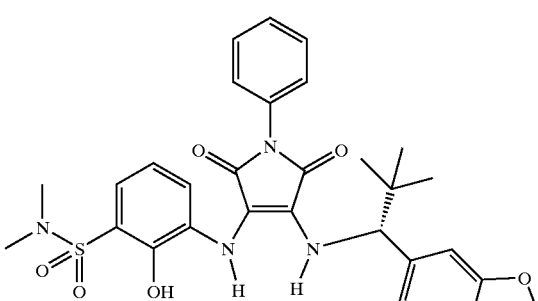 |
| 709 | (1) 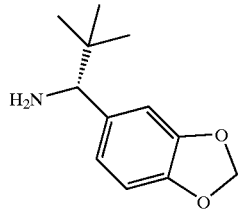 (2) 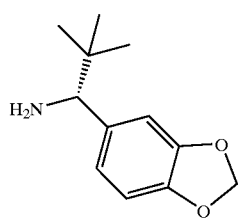 | 42 | 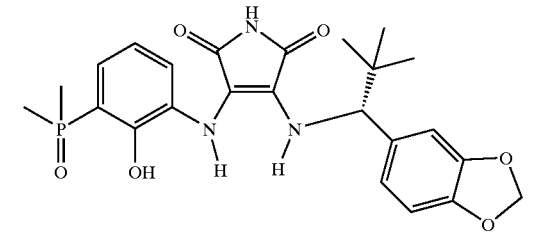 |
| 710 | (1) (2) 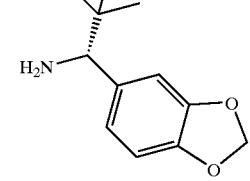 | 40 | |

-continued

| Ex. | Amine<br>(1) (B—NH₂)<br>(2) (A—NH₂) | Prep Ex<br>of<br>Dichloride | Product |
|---|---|---|---|
| 711 | (1) (2) | 41 | |
| 712 | (1) (2) | 43 | |
| 713 | (1) (2) | 42 | |

-continued

| Ex. | Amine<br>(1) (B—NH₂)<br>(2) (A—NH₂) | Prep Ex<br>of<br>Dichloride | Product |
|---|---|---|---|
| 714 | (1) ![structure] (2) ![structure] | 40 | ![structure] |
| 715 | (1) ![structure] (2) ![structure] | 41 | ![structure] |
| 716 | (1) ![structure] (2) ![structure] | 43 | ![structure] |

-continued

| Ex. | Amine<br>(1) (B—NH₂)<br>(2) (A—NH₂) | Prep Ex of Dichloride | Product |
|---|---|---|---|
| 717 | (1), (2) | 42 | |
| 718 | (1), (2) | 40 | |
| 719 | (1), (2) | 41 | |

-continued

| Ex. | Amine (1) (B—NH₂) (2) (A—NH₂) | Prep Ex of Dichloride | Product |
|---|---|---|---|
| 720 | (1) ![structure] (2) ![structure] | 42 | ![structure] |
| 721 | (1) ![structure] (2) ![structure] | 43 | ![structure] |
| 722 | (1) ![structure] (2) ![structure] | 40 | ![structure] |
| 723 | (1) ![structure] (2) ![structure] | 41 | ![structure] |

| Ex. | Amine (1) (B—NH₂) (2) (A—NH₂) | Prep Ex of Dichloride | Product |
|---|---|---|---|
| 724 | (1) 3-amino-2-hydroxy-N,N-dimethylbenzamide (2) (S)-1-(5-methylfuran-2-yl)propan-1-amine | 43 | |
| 725 | (1) 3-amino-2-hydroxy-N,N-dimethylbenzamide (2) (S)-1-(5-methylfuran-2-yl)propan-1-amine | 42 | |
| 726 | (1) 3-amino-2-hydroxy-N,N-dimethylbenzenesulfonamide (2) (S)-1-(5-methylfuran-2-yl)propan-1-amine | 43 | |
| 727 | (1) 3-amino-2-hydroxy-N,N-dimethylbenzenesulfonamide (2) (S)-1-(5-methylfuran-2-yl)propan-1-amine | 41 | |

-continued
| Ex. | Amine<br>(1) (B—NH$_2$)<br>(2) (A—NH$_2$) | Prep Ex of Dichloride | Product |
|---|---|---|---|
| 728 | (1) 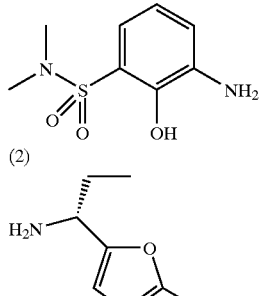 (2) 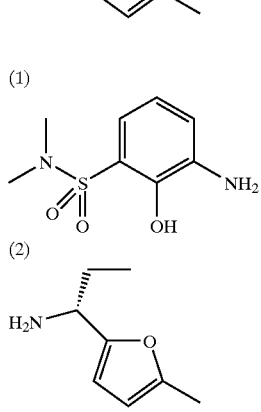 | 40 | 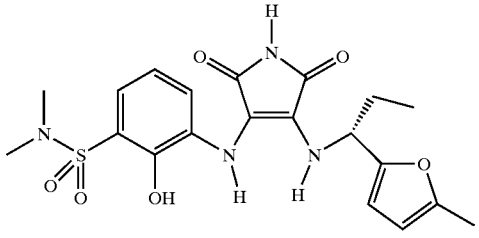 |
| 729 | (1) 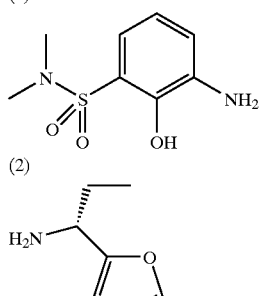 (2)  | 42 | 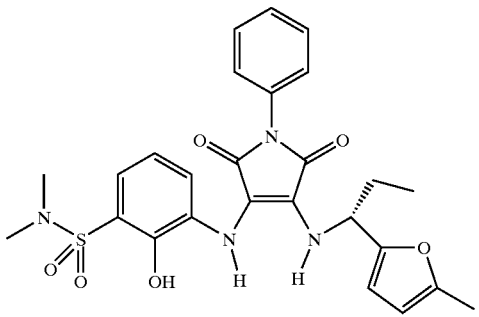 |
| 730 | (1) 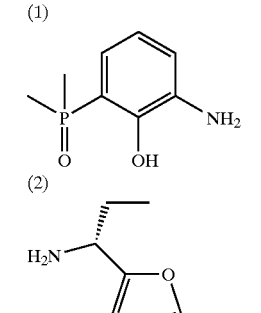 (2)  | 40 | 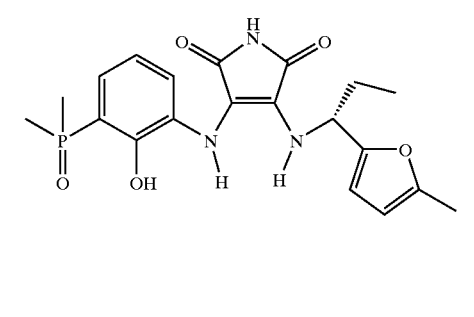 |
| 731 | (1) 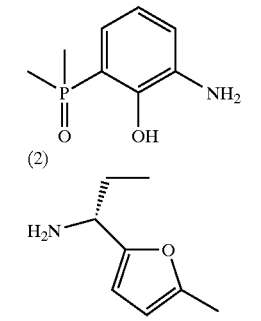 (2)  | 41 | 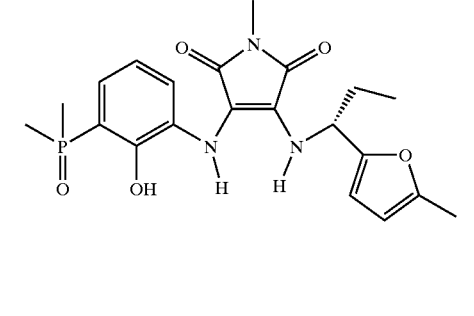 |

-continued

| Ex. | Amine<br>(1) (B—NH$_2$)<br>(2) (A—NH$_2$) | Prep Ex<br>of<br>Dichloride | Product |
|---|---|---|---|
| 732 | (1) 3-amino-2-hydroxyphenyl methylphosphine oxide<br>(2) (S)-1-(5-methylfuran-2-yl)propylamine | 43 | N-benzyl maleimide derivative |
| 733 | (1) 3-amino-2-hydroxyphenyl methylphosphine oxide<br>(2) (S)-1-(5-methylfuran-2-yl)propylamine | 42 | N-phenyl maleimide derivative |
| 734 | (1) 3-amino-2-hydroxy-N,N,N'-trimethylbenzamidine<br>(2) (S)-1-(5-methylfuran-2-yl)propylamine | 40 | NH maleimide derivative |
| 735 | (1) 3-amino-2-hydroxy-N,N,N'-trimethylbenzamidine<br>(2) (S)-1-(5-methylfuran-2-yl)propylamine | 41 | N-methyl maleimide derivative |

US 6,903,131 B2
215 216
-continued
| Ex. | Amine<br>(1) (B—NH$_2$)<br>(2) (A—NH$_2$) | Prep Ex<br>of<br>Dichloride | Product |
|---|---|---|---|
| 736 | (1) 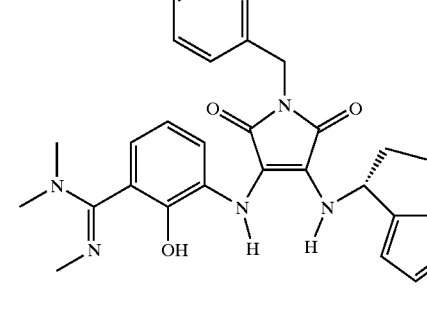<br>(2) 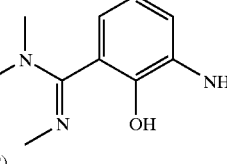 | 43 | 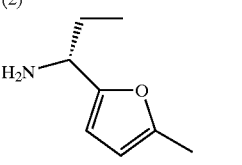 |
| 737 | (1) 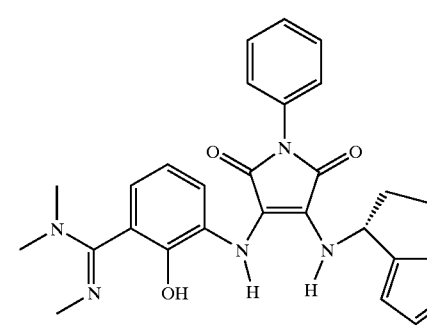<br>(2) 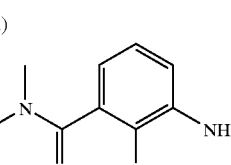 | 42 | 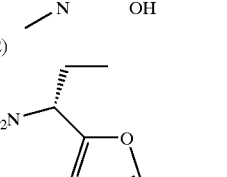 |
| 738 | (1) 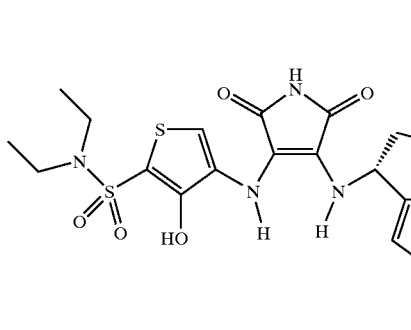<br>(2) 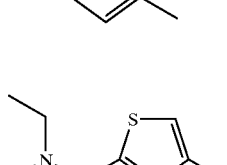 | 40 | 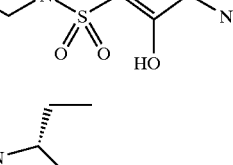 |
| 739 | (1) 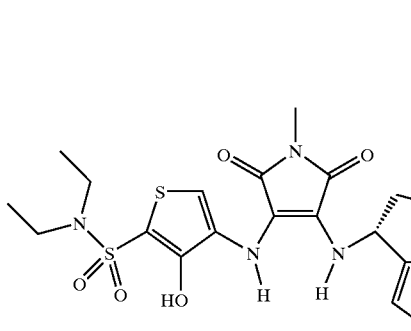<br>(2) 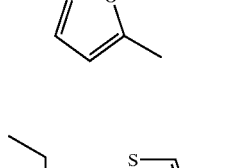 | 41 | 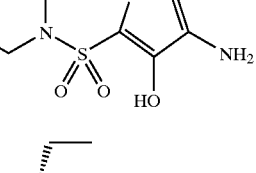 |

-continued

| Ex. | Amine (1) (B—NH$_2$) (2) (A—NH$_2$) | Prep Ex of Dichloride | Product |
|---|---|---|---|
| 740 | (1) ... (2) ... | 42 | ... |
| 741 | (1) ... (2) ... | 43 | ... |

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula (I);

(I)

or a pharmaceutically acceptable salt or solvate thereof, wherein:

$R^1$ is selected from the group consisting of: H, aryl, alkyl, arylalkyl, cycloalkyl, and cycloalkylalkyl; optionally substituted with one or more substituents selected from the group consisting of:
a) H,
b) Halogen,
c) CF$_3$,
d) COR$^{13}$,
e) OH,
f) NR$^{13}$R$^{14}$,
g) NO$_2$,
h) Cyano,
i) —Si(alkyl),
j) —Si(aryl),
k) SO$_2$OR$^{13}$,
l) CO$_2$R$^{13}$,
m) CONR$^{13}$R$^{14}$,
n) SO$_2$NR$^{13}$R$^{14}$,
o) SO$_2$R$^{13}$,
p) —OR$^{13}$,
r) —NR$^{13}$R$^{14}$,
s) —O(C═O)R$^{13}$,
t) —O(C═O)NR$^{13}$R$^{14}$,
u) —NR$^{13}$COR$^{14}$ and
v) —NR$^{13}$CO$_2$R$^{14}$;

A is selected from the group consisting of:

(1)

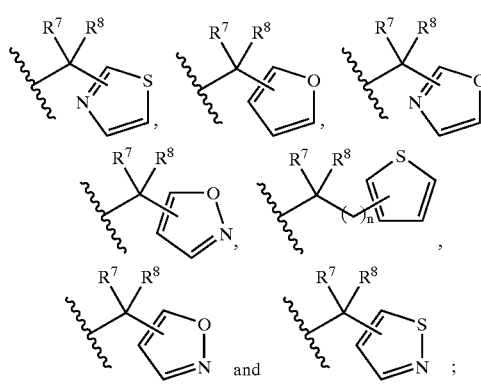

219
-continued (2)

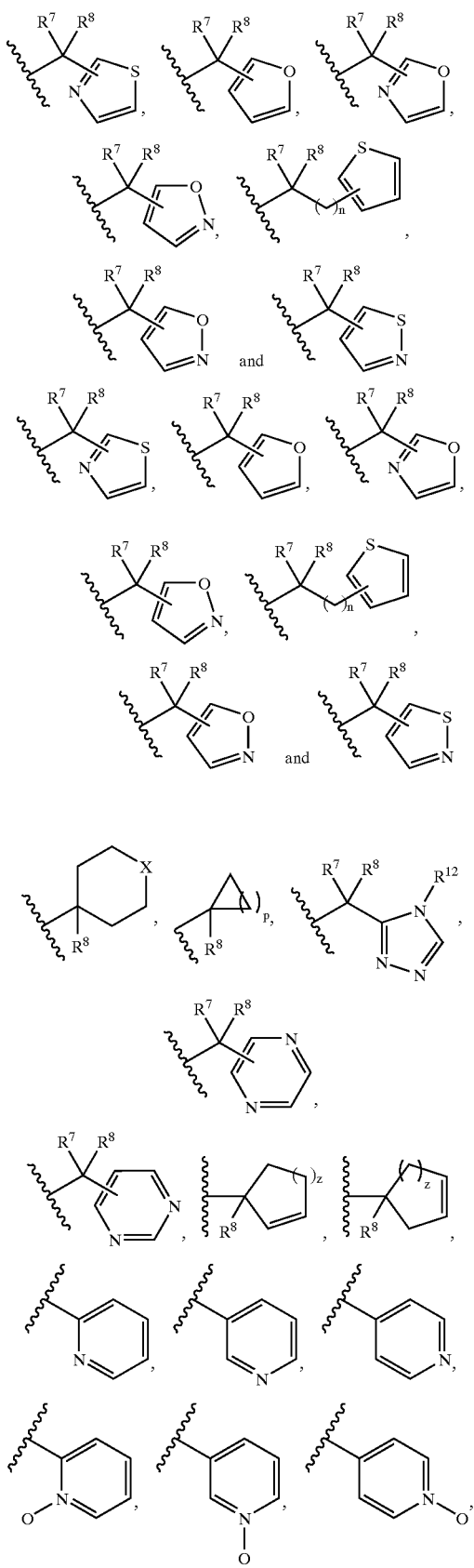

220
-continued

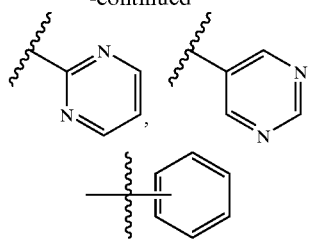

wherein the above rings of said A groups are substituted with 1 to 6 substituents each independently selected from the group consisting of: $R^9$ groups; and (3)

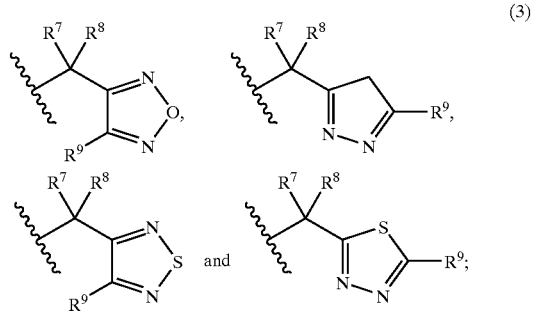

B is

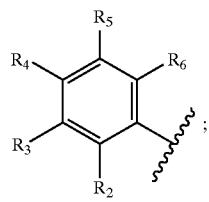

n is 0 to 6;

$R^2$ is selected from the group consisting of: hydrogen, OH, —C(O)OH, —SH, —SO$_2$NR$^{13}$R$^{14}$, —NHC(O)R$^{13}$, —NHSO$_2$NR$^{13}$R$^{14}$, —NHSO$_2$R$^{13}$, —NR$^{13}$R$^{14}$, —C(O)NR$^{13}$R$^{14}$, —C(O)NHOR$^{13}$, —C(O)NR$^{13}$OH, —S(O$_2$)OH, and —OC(O)R$^{13}$;

each $R^3$ and $R^4$ is independently selected from the group consisting of: hydrogen, cyano, halogen, alkyl, alkoxy, —OH, —CF$_3$, —OCF$_3$, —NO$_2$, —C(O)R$^{13}$, —C(O)OR$^{13}$, —C(O)NHR$^{17}$, —C(O)NR$^{13}$R$^{14}$, —SO$_{(t)}$NR$^{13}$R$^{14}$, —SO$_{(t)}$R$^{13}$, —C(O)NR$^{13}$OR$^{14}$, unsubstituted or substituted aryl,

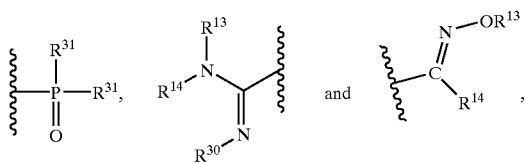

wherein there are 1 to 6 substituents on said substituted aryl group and each substituent is selected from the group consisting of: $R^9$ groups;

each $R^5$ and $R^6$ are the same or different and are independently selected from the group consisting of hydrogen, halogen, alkyl, alkoxy, —CF$_3$, —OCF$_3$, —NO$_2$, —C(O)R$^{13}$, —C(O)OR$^{13}$, —C(O)NR$^{13}$R$^{14}$, —SO$_{(t)}$NR$^{13}$R$^{14}$, —C(O)NR$^{13}$OR$^{14}$, cyano, and unsubstituted or substituted aryl; wherein there are 1 to 6 substituents on said substituted aryl group and each substituent is independently selected from the group consisting of: R$^9$ groups;

each R$^7$ and R$^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —CO$_2$R$^{13}$, —CONR$^{13}$R$^{14}$, alkynyl, alkenyl, and cycloalkenyl; and wherein there are one or more substituents on said substituted R$^7$ and R$^8$ groups, wherein each substituent is independently selected from the group consisting of:

a) halogen,
b) —CF$_3$,
c) —COR$^{13}$,
d) —OR$^{13}$,
e) —NR$^{13}$R$^{14}$,
f) —NO$_2$,
g) —CN,
h) —SO$_2$OR$^{13}$,
i) —Si(alkyl)$_3$, wherein each alkyl is independently selected,
j) —Si(aryl)$_3$, wherein each alkyl is independently selected,
k) —(R$^{13}$)$_2$R$^{14}$Si, wherein each R$^{13}$ is independently selected,
l) —CO$_2$R$^{13}$,
m) —C(O)NR$^{13}$R$^{14}$,
n) —SO$_2$NR$^{13}$R$^{14}$,
o) —SO$_2$R$^{13}$,
p) —OC(O)R$^{13}$,
q) —OC(O)NR$^{13}$R$^{14}$,
r) —NR$^{13}$C(O)R$^{14}$, and
s) —NR$^{13}$CO$_2$R$^{14}$;

each R$^9$ is independently selected from the group consisting of:
a) —R$^{13}$,
b) halogen,
c) —CF$_3$,
d) —COR$^{13}$,
e) —OR$^{13}$,
f) —NR$^{13}$R$^{14}$,
g) —NO$_2$,
h) —CN,
i) —SO$_2$R$^{13}$,
j) —SO$_2$NR$^{13}$R$^{14}$,
k) —NR$^{13}$COR$^{14}$,
l) —CONR$^{13}$R$^{14}$,
m) —NR$^{13}$CO$_2$R$^{14}$,
n) —CO$_2$R$^{13}$, o) 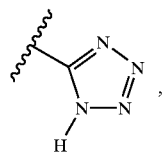, p) alkyl substituted with one or more —OH groups,
q) alkyl substituted with one or more —NR$^{13}$R$^{14}$ group, and
r) —N(R$^{13}$)SO$_2$R$^{14}$;

each R$^{13}$ and R$^{14}$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, unsubstituted or substituted heterocyclic, unsubstituted or substituted fluoroalkyl, and unsubstituted or substituted heterocycloalkylalkyl (wherein "heterocyloalkyl" means heterocyclic); wherein there are 1 to 6 substituents on said substituted R$^{13}$ and R$^{14}$ groups and each substituent is independently selected from the group consisting of: alkyl, —CF$_3$, —OH, alkoxy, aryl, arylalkyl, fluroalkyl, cycloalkyl, cycloalkylalkyl, heteroaryl, heteroarylalkyl, —N(R$^{40}$)$_2$, —C(O)OR$^{15}$, —C(O)NR$^{15}$R$^{16}$, —S(O)$_t$NR$^{15}$R$^{16}$, —C(O)R$^{15}$, —SO$_2$R$^{15}$ provided that R$^{15}$ is not H, halogen, and —NHC(O)NR$^{15}$R$^{16}$; or R$^{13}$ and R$^{14}$ taken together with the nitrogen they are attached to in the groups —C(O)NR$^{13}$R$^{14}$ and —SO$_2$NR$^{13}$R$^{14}$ form an unsubstituted or substituted saturated heterocyclic ring, said ring optionally containing one additional heteroatom selected from the group consisting of: O, S and NR$^{18}$; wherein there are 1 to 3 substituents on the substituted cyclized R$^{13}$ and R$^{14}$ groups and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_t$NR$^{15}$R$^{16}$, —C(O)R$^{15}$, —SO$_2$R$^{15}$ provided that R$^{15}$ is not H, —NHC(O)NR$^{15}$R$^{16}$, —NHC(O)OR$^{15}$, halogen, and a heterocycloalkenyl group;

each R$^{15}$ and R$^{16}$ is independently selected from the group consisting of: H, alkyl, aryl, arylalkyl, cycloalkyl and heteroaryl;

R$^{17}$ is selected from the group consisting of: —SO$_2$alkyl, —SO$_2$aryl, —SO$_2$cycloalkyl, and —SO$_2$heteroaryl;

R$^{18}$ is selected from the group consisting of: H, alkyl, aryl, heteroaryl, —C(O)R$^{19}$, —SO$_2$R$^{19}$ and —C(O)NR$^{19}$R$^{20}$;

each R$^{19}$ and R$^{20}$ is independently selected from the group consisting of: alkyl, aryl and heteroaryl;

R$^{30}$ is selected from the group consisting of: alkyl, cycloalkyl, —CN, —NO$_2$, or —SO$_2$R$^{15}$ provided that R$^{15}$ not H;

each R$^{31}$ is independently selected from the group consisting of: unsubstituted alkyl, unsubstituted or substituted aryl, unsubstituted or substituted heteroaryl and unsubstituted or substituted cycloalkyl; wherein there are 1 to 6 substituents on said substituted R$^{31}$ groups and each substituent is independently selected from the group consisting of: alkyl, halogen and —CF$_3$;

each $R^{40}$ is independently selected from the group consisting of; H, alkyl and cycloalkyl; and
t is 0, 1 or 2.
2. The compound of claim 1 wherein A is selected from the group consisting of:
unsubstituted or substituted:
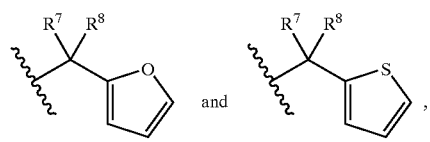
and
3. The compound of claim 1 wherein A is selected from the group consisting of:
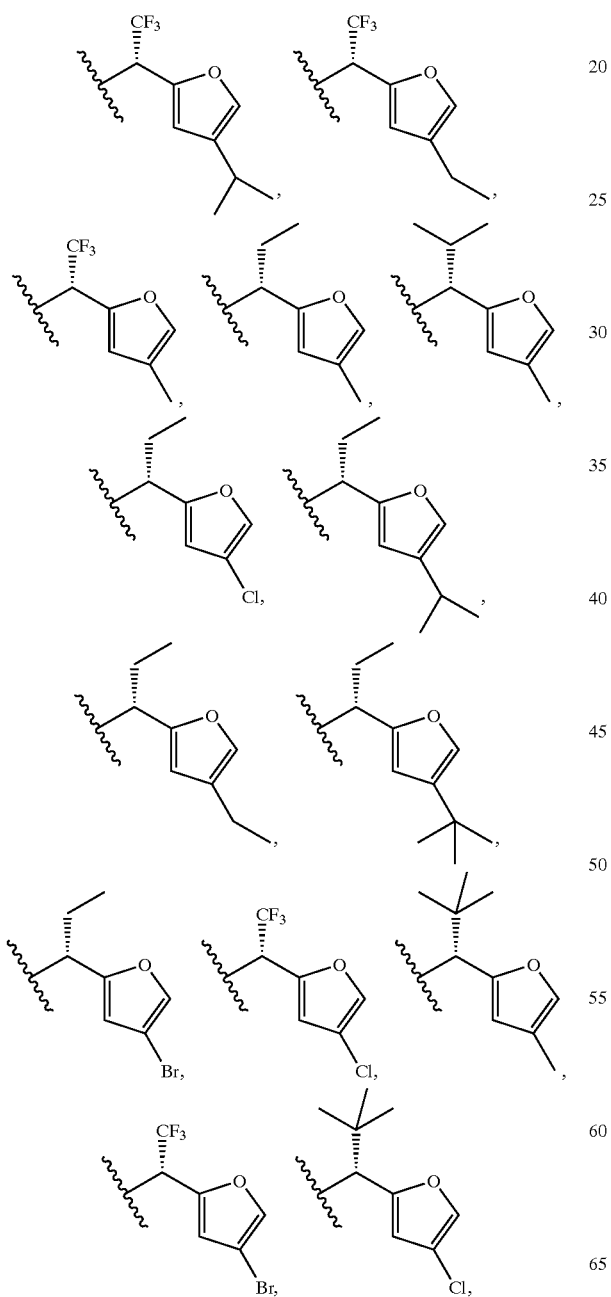
-continued
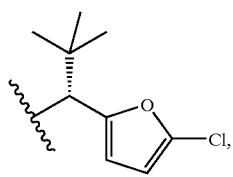
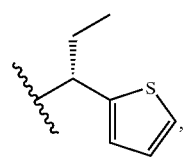
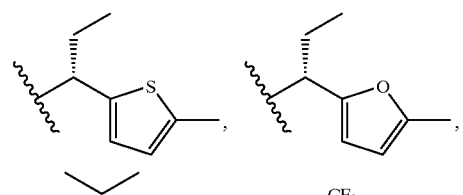
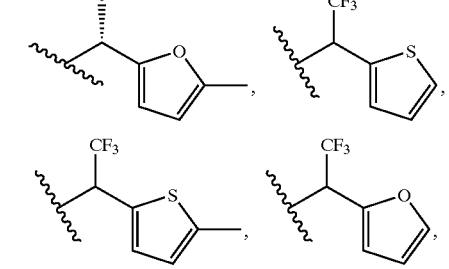
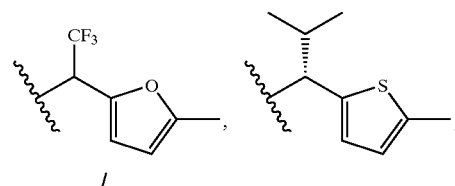
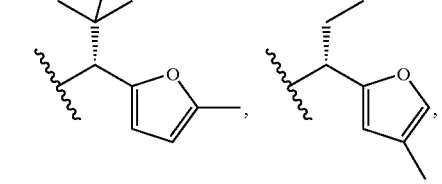
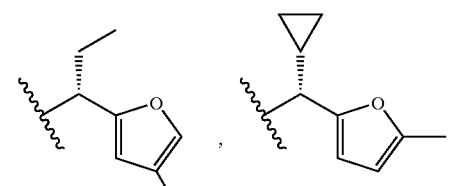
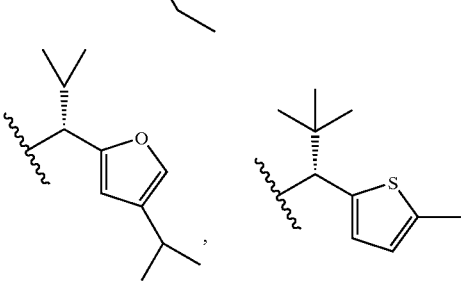

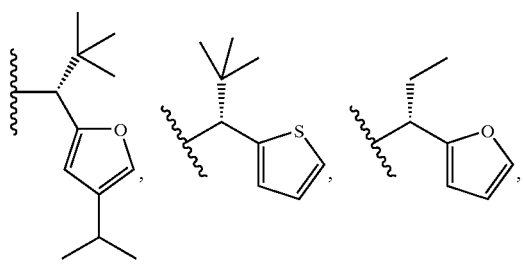
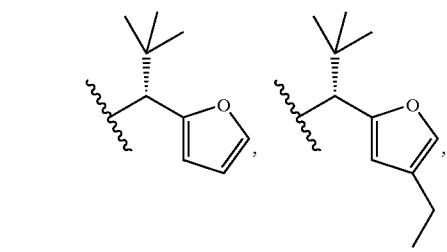
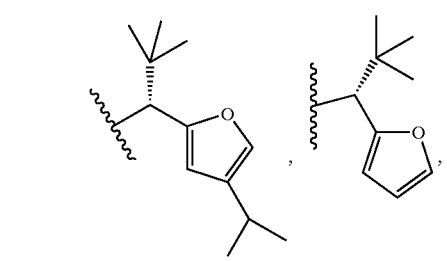
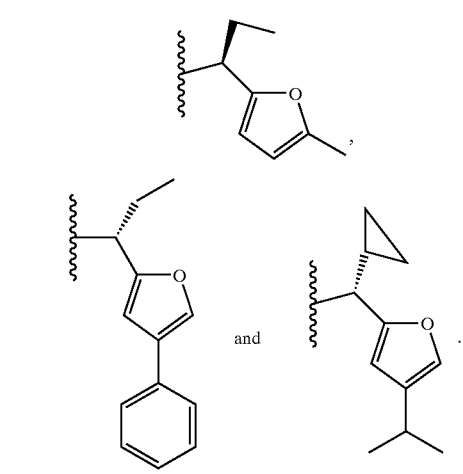
4. The compound of claim 1 wherein A is selected from the group consisting of:
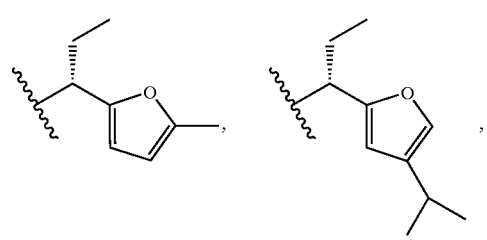
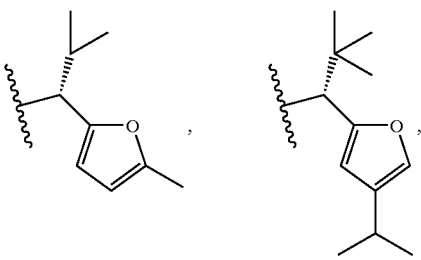
5. The compound of claim 1 wherein B is:
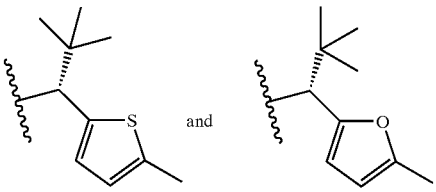
6. The compound of claim 1 wherein B is selected from the group consisting of:
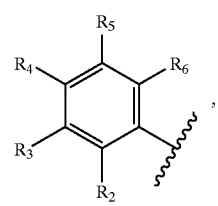
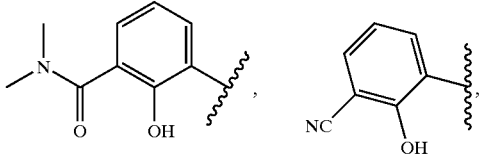
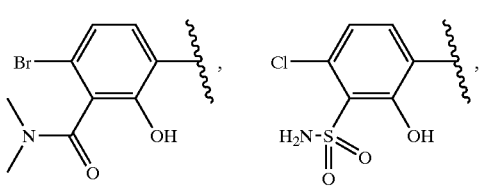
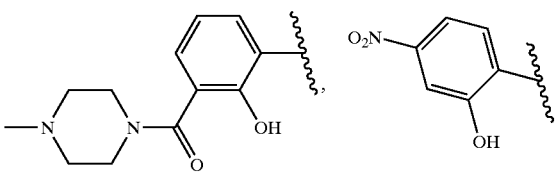
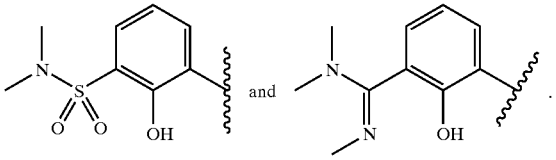

7. The compound of claim 1 wherein B is

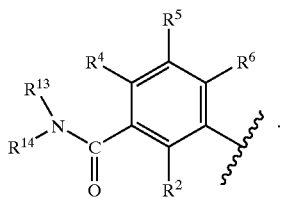

8. The compound of claim 1 wherein B is:

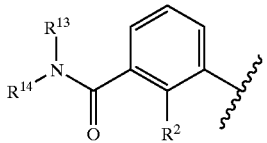

wherein R is —OH, and $R^{13}$ and $R^{14}$ are independently selected from the group consisting of H and alkyl.

9. The compound of claim 1 wherein $R^1$ is selected from the group consisting of: H, alkyl, aryl and cycloalkyl.

10. The compound of claim 1 wherein: $R^1$ is selected from H, methyl, phenyl and cyclohexyl.

11. The compound of claim 1 wherein
(1) substituent A in formula I is selected from the group consisting of:

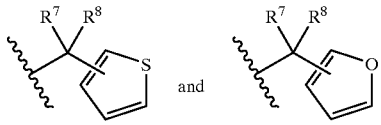

and wherein the above rings are unsubstituted, or the above rings are substituted with 1 to 3 substituents independently selected from the group consisting of: H, F, Cl, Br, alkyl, cycloalkyl, and —$CF_3$; $R^7$ is selected from the group consisting of: H, —$CF_3$, —$CF_2CH_3$, methyl, ethyl, isopropyl, cyclopropyl and t-butyl; and $R^8$ is H; and (2) substituent B in formula I is:

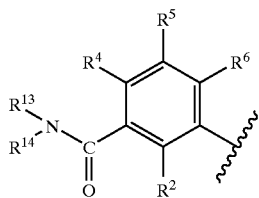

wherein:
$R^2$ is selected from the group consisting of: H, OH, —NHC(O)$R^{13}$ and —NHSO$_2R^{13}$;
$R^4$ is selected from the group consisting of: H, —$NO_2$, cyano, —$CH_3$ or —$CF_3$;
$R^5$ is selected from the group consisting of: H, —$CF_3$, —$NO_2$, halogen and cyano;
$R^6$ is selected from the group consisting of: H, alkyl and —$CF_3$; and
each $R^{13}$ and $R^{14}$ is independently selected from the group coifisisting of: H, methyl, ethyl and isopropyl; or $R^{13}$ and $R^{14}$ when taken together with the nitrogen they are attached to in the groups —NR$^{13}$R$^{14}$, —C(O)NR$^{13}$R$^{14}$, —SO$_2$NR$^{13}$R$^{14}$, —OC(O)NR$^{13}$R$^{14}$, —CONR$^{13}$R$^{14}$, —NR$^{13}$C(O)NR$^{13}$R$^{14}$, —SO$_r$NR$^{13}$R$^{14}$, —NHSO$_2$NR$^{13}$R$^{14}$ form an unsubstituted or substituted saturated heterocyclic ring optionally having one additional heteroatom selected from O, S or NR$^{18}$ wherein R$^{18}$ is selected from H, alkyl, aryl, heteroaryl, —C(O)R$^{19}$, —SO$_2$R$^{19}$ and —C(O)NR$^{19}$R$^{20}$, wherein each R$^{19}$ and R$^{20}$ is independently selected from alkyl, aryl and heteroaryl, wherein there are 1 to 3 substituents on the substituted cyclized R$^{13}$ and R$^{14}$ groups and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}$R$^{16}$, —SO$_r$NR$^{15}$R$^{16}$, —C(O)R$^{15}$, —SO$_2$R$^{15}$ provided that R$^{15}$ is not H, —NHC(O)NR$^{15}$R$^{16}$ and halogen; and wherein each R$^{15}$ and R$^{16}$ is independently selected from the group consisting of: H, alkyl, aryl, arylalkyl, cycloalkyl and heteroaryl.

12. The compound of claim 1 wherein:
(1) substituent A in formula I is selected from the group consisting of:

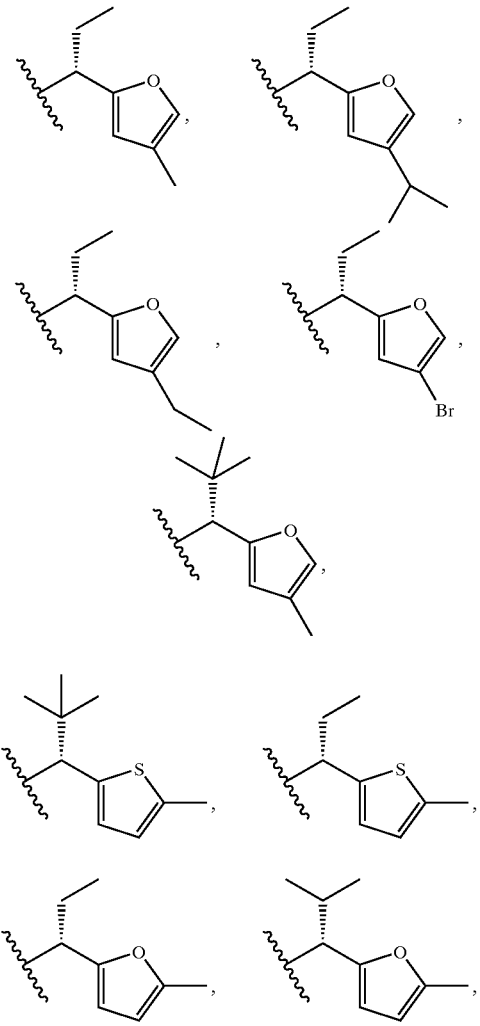

-continued

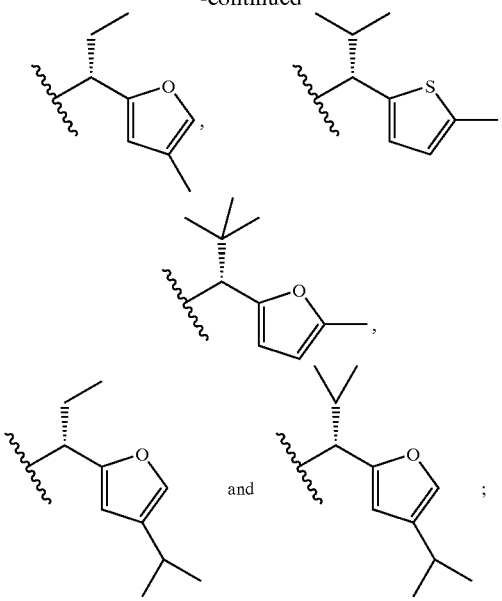

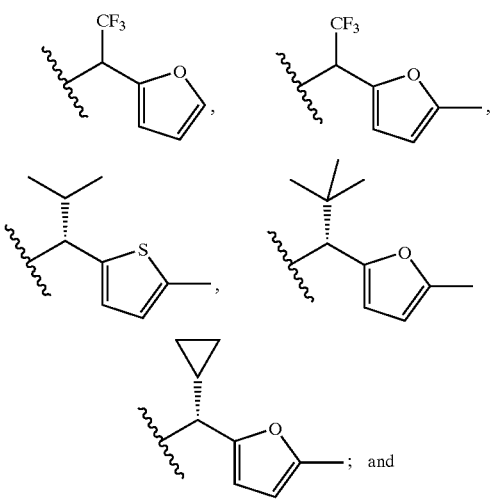

(2) substituent B in formula I is:

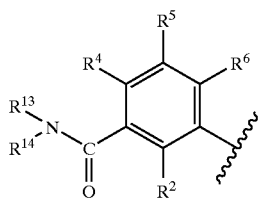

wherein:

R² is —OH;

R⁴ is selected form the group consisting of: H, —CH₃ and —CF₃;

R⁵ is selected from the group consisting of: H and cyano;

R⁶ is selected from the group consisting of: H, —CH₃ and —CF₃; and

R¹³ and R¹⁴ are independently selected from the group consisting of H and methyl.

13. The compound of claim 1 wherein:

A is selected from:

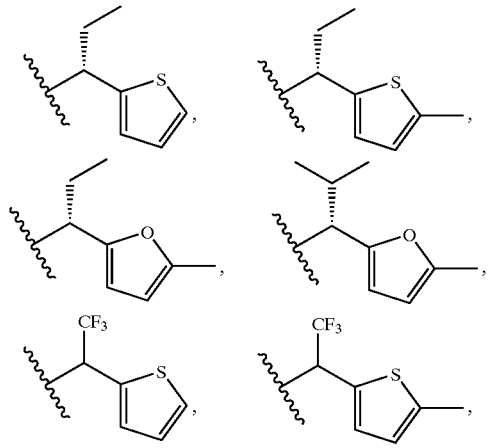

B is

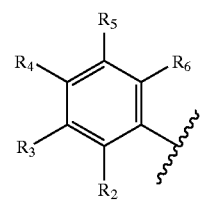

wherein,

R² is —OH;

R³ is CONR¹³R¹⁴;

R⁴ is selected from the group consisting of H, CF₃ and CH₃;

R⁵ is H and cyano;

R⁶ is selected from the group consisting of H, CH₃ and CE₃;

R¹³ and R¹⁴ are methyl.

14. The compound of claim 1 selected from the group consisting of:

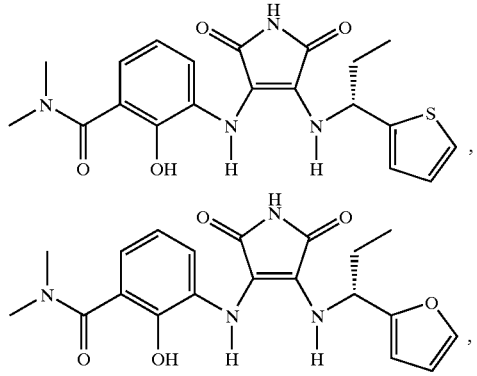

231
-continued
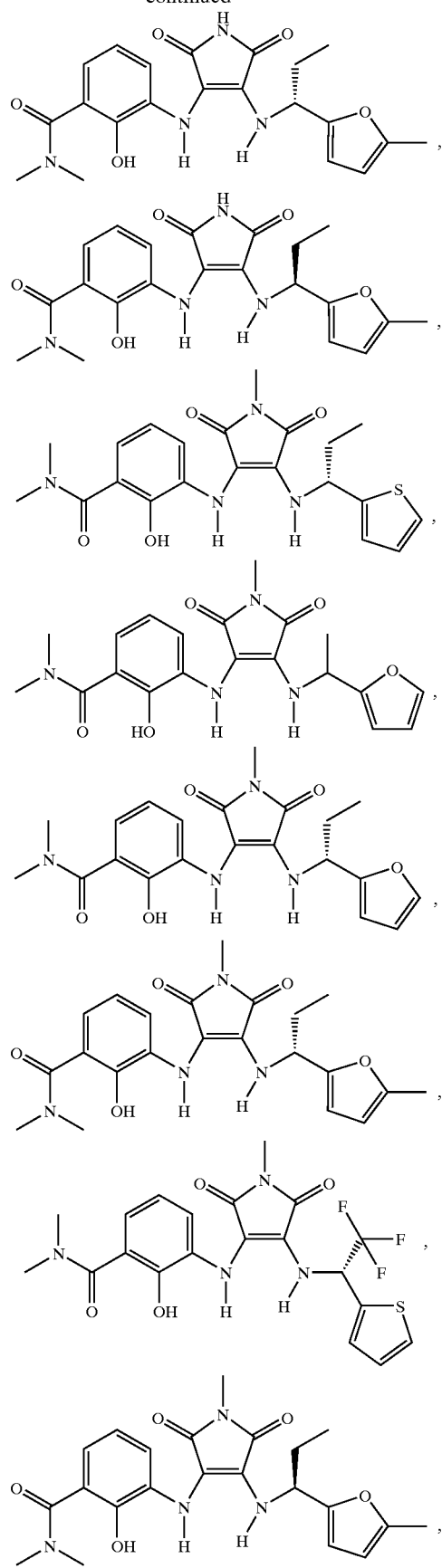
232
-continued
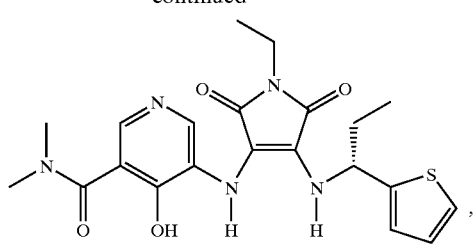
15. The compound of claim 1 selected from the group consisting of:
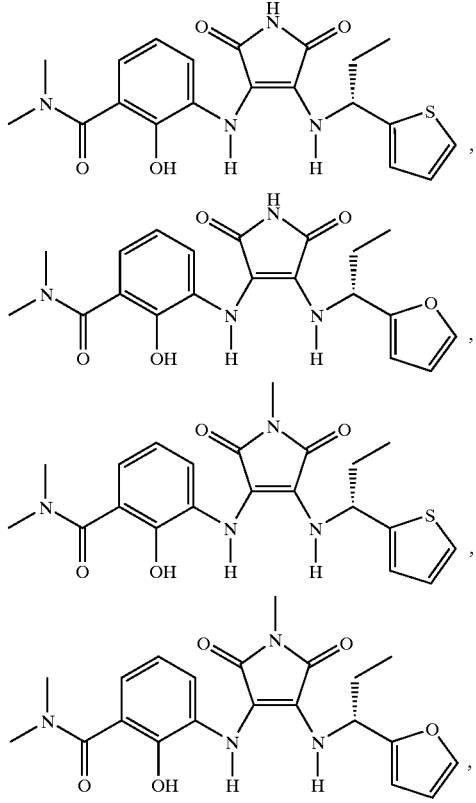

-continued
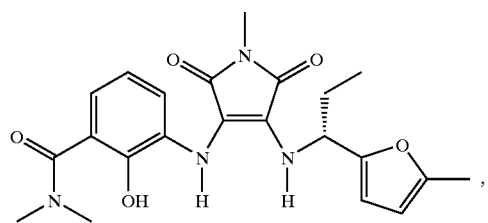
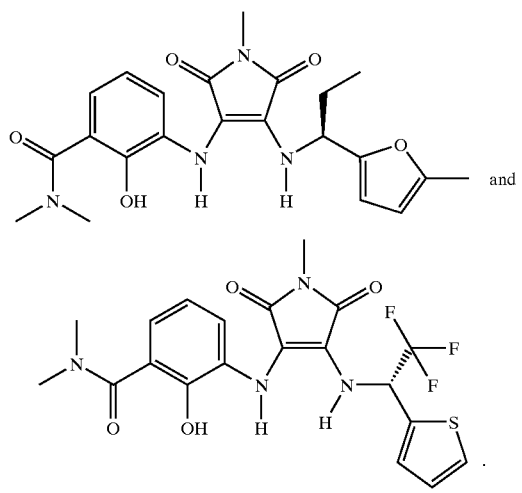
16. The compound of claim 1 having the formula:
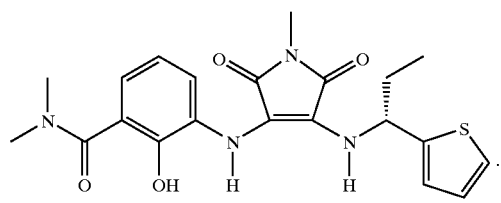
17. The compound of claim 1 having the formula
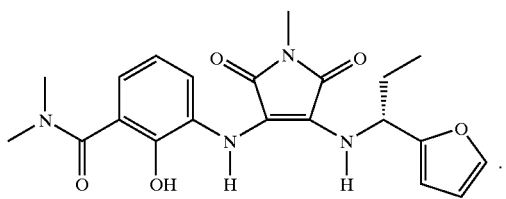
18. The compound of claim 1 having the formula
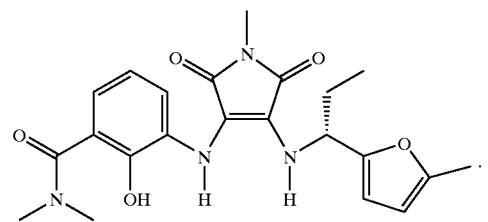
19. The compound of claim 1 having the formula
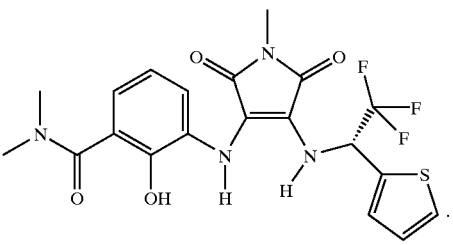
20. The compound of claim 1 selected from the group consisting of:
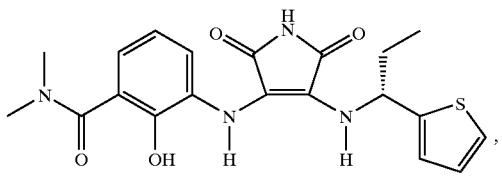
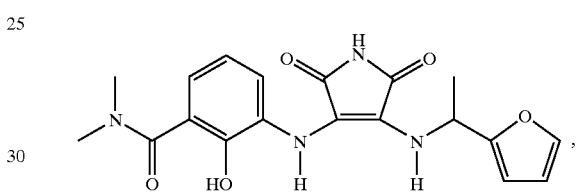
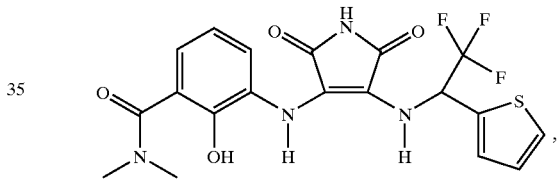
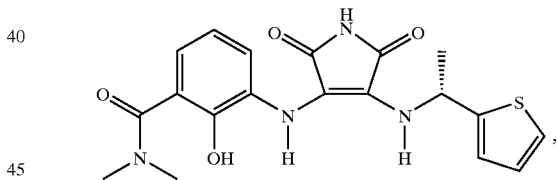
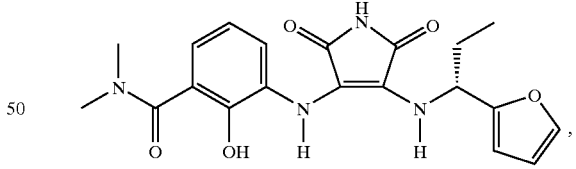
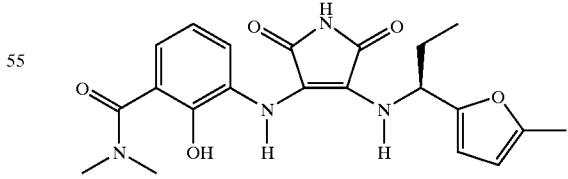
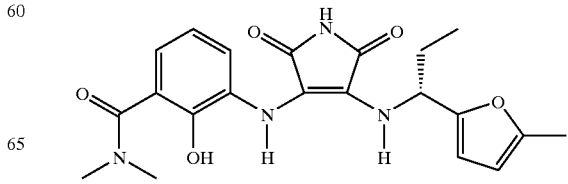

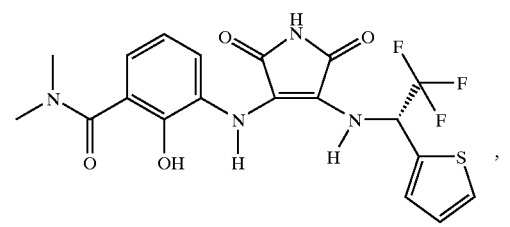
,
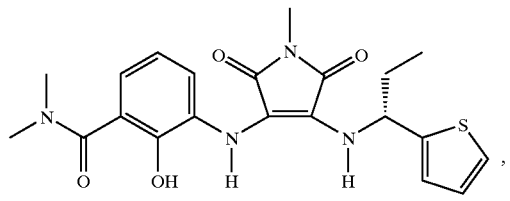
,
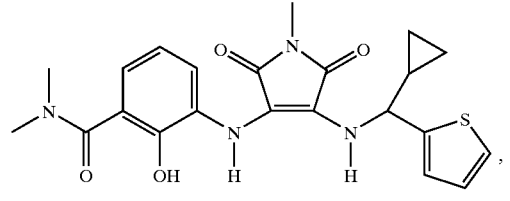
,
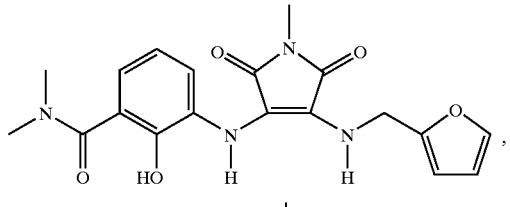
,
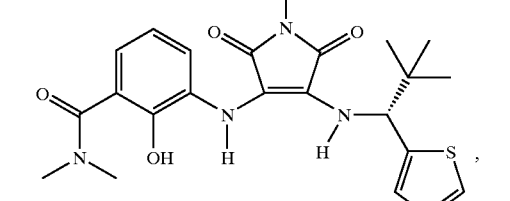
,
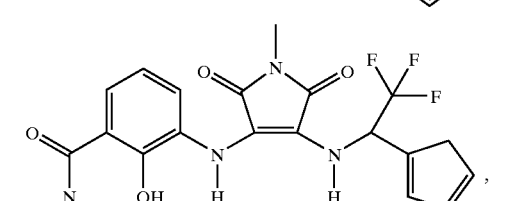
,
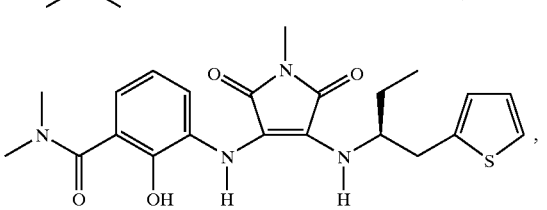
,
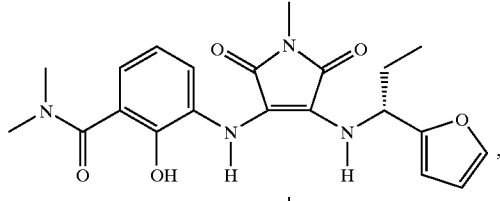
,
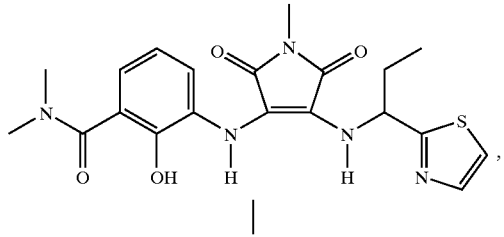
,
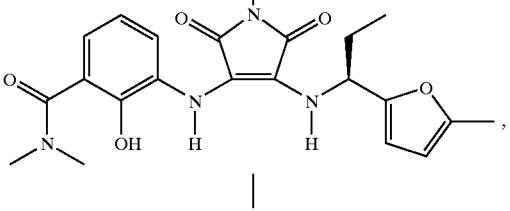
,
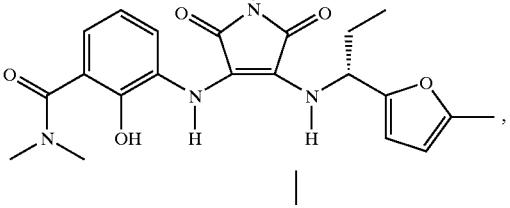
,
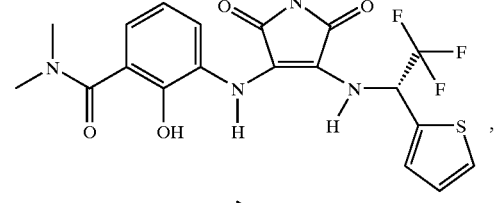
,
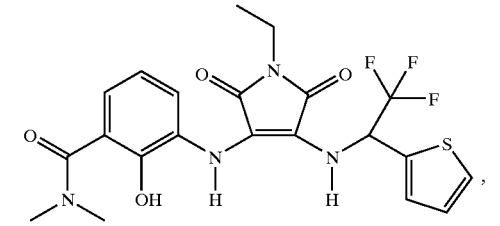
,
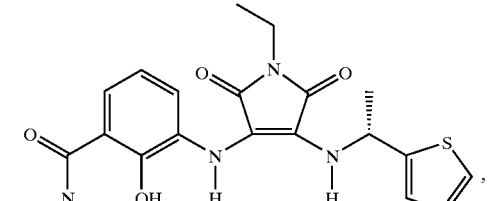
, 237
-continued
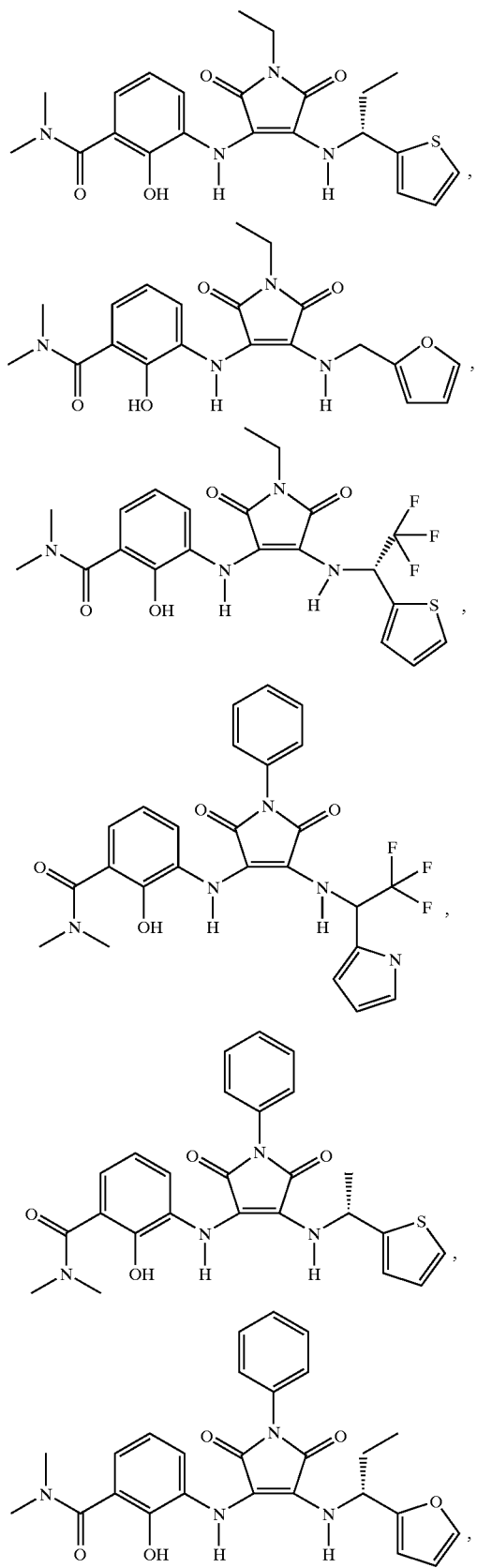
238
-continued
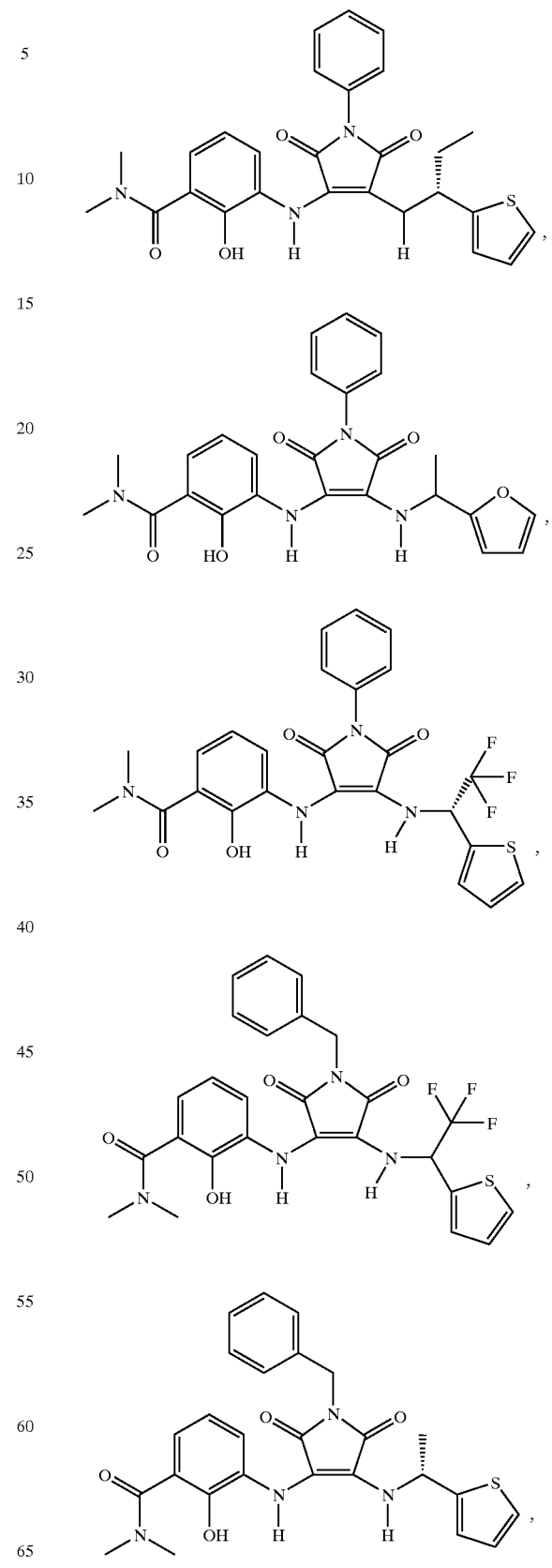

-continued
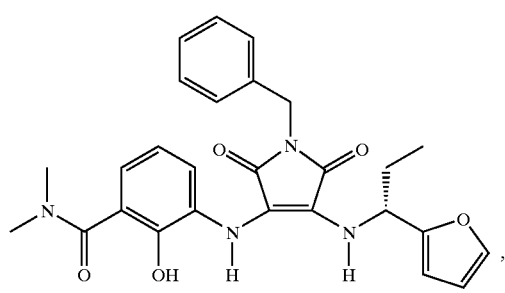
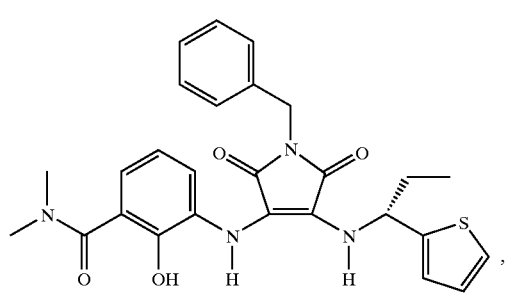
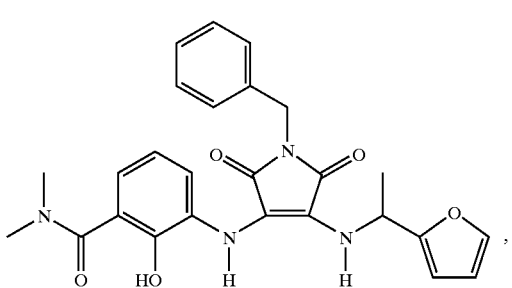
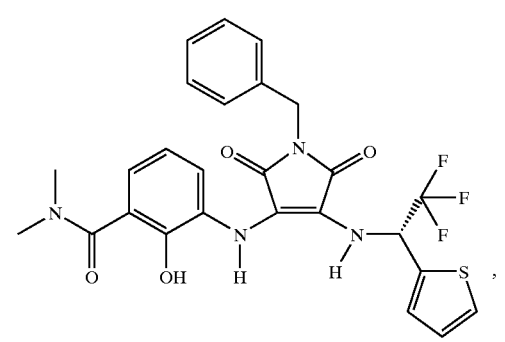
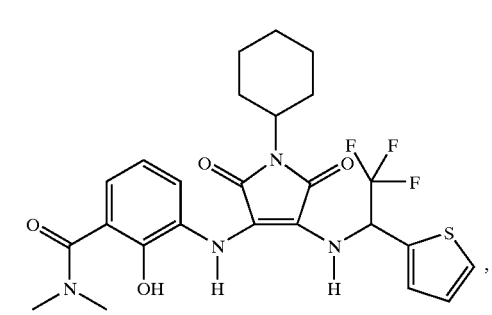
-continued
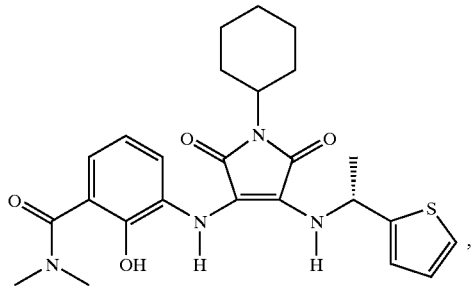
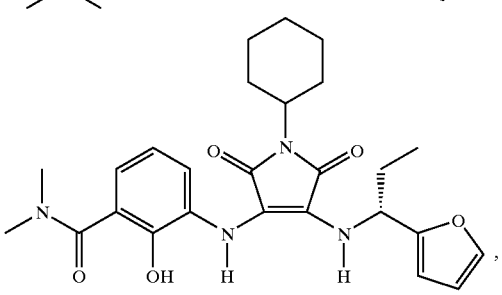
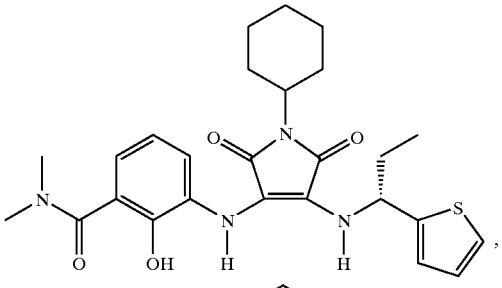
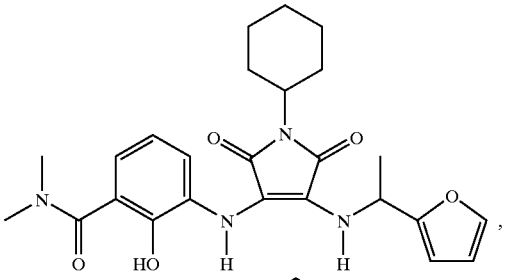
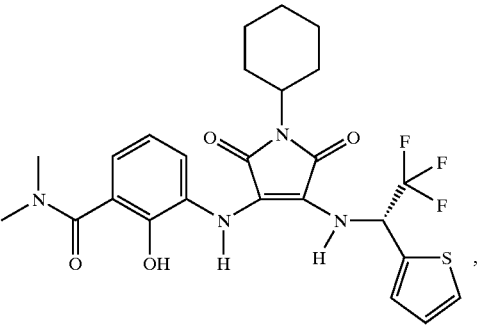
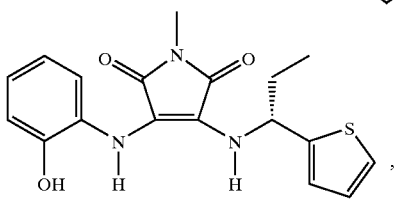

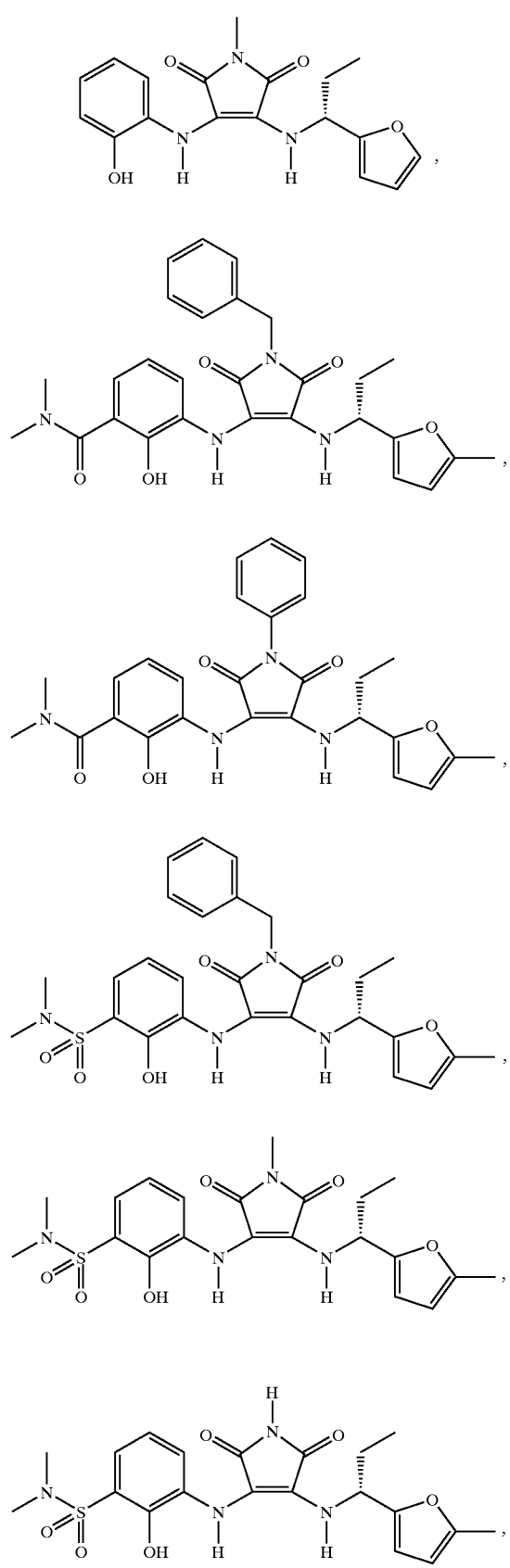
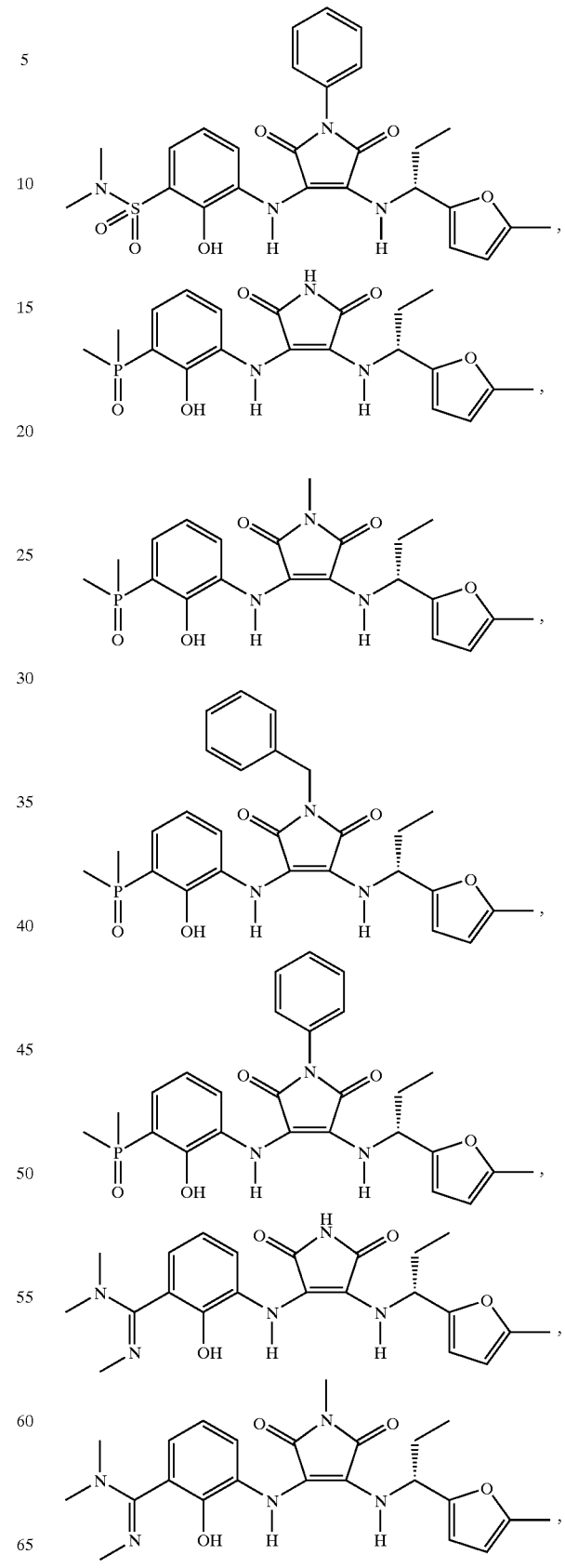

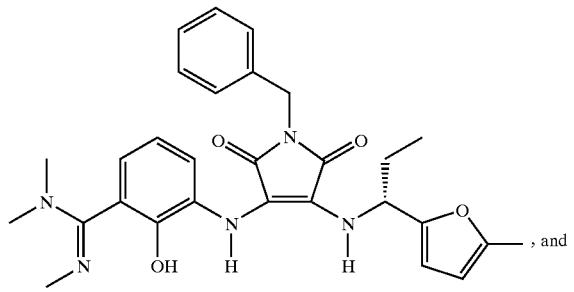
, and
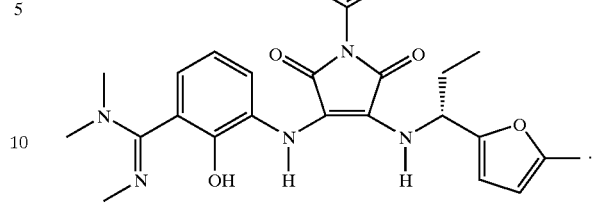
21. A pharmaceutical composition comprising a compound of claim 1, and a pharmaceutically acceptable carrier therefor.
* * * * *